United States Patent
Van Maris et al.

(10) Patent No.: US 12,398,398 B2
(45) Date of Patent: *Aug. 26, 2025

(54) RECOMBINANT YEAST EXPRESSING RUBISCO AND PHOSPHORIBULOKINASE

(71) Applicant: DANISCO US INC., Palo Alto, CA (US)

(72) Inventors: Antonius Jeroen Adriaan Van Maris, Delft (NL); Jacobus Thomas Pronk, Delft (NL); Victor Gabriel Guadalupe Medina, Delft (NL); Hendrik Wouter Wisselink, Delft (NL)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/108,027

(22) Filed: Dec. 1, 2020

(65) Prior Publication Data

US 2021/0147859 A1    May 20, 2021

Related U.S. Application Data

(63) Continuation of application No. 15/980,413, filed on May 15, 2018, now abandoned, which is a continuation of application No. 14/767,661, filed as application No. PCT/NL2014/050106 on Feb. 21, 2014, now Pat. No. 10,093,937.

(30) Foreign Application Priority Data

Feb. 22, 2013  (EP) .................................... 13156448

(51) Int. Cl.
| | | |
|---|---|---|
| C12N 1/19 | (2006.01) | |
| C07K 14/245 | (2006.01) | |
| C12N 1/16 | (2006.01) | |
| C12N 9/08 | (2006.01) | |
| C12N 9/12 | (2006.01) | |
| C12N 9/88 | (2006.01) | |
| C12N 15/81 | (2006.01) | |
| C12P 7/06 | (2006.01) | |
| C12P 7/62 | (2022.01) | |
| C12P 13/04 | (2006.01) | |

(52) U.S. Cl.
CPC ............ *C12N 15/81* (2013.01); *C07K 14/245* (2013.01); *C12N 1/16* (2013.01); *C12N 9/1205* (2013.01); *C12N 9/88* (2013.01); *C12P 7/06* (2013.01); *C12P 7/62* (2013.01); *C12P 13/04* (2013.01); *C12Y 207/01019* (2013.01); *C12Y 401/01039* (2013.01); *Y02E 50/10* (2013.01)

(58) Field of Classification Search
CPC ...... C12N 9/88; C12N 9/1205; C12N 9/0006; C12Y 401/01039; C12Y 207/01019; C12Y 101/01; C12P 7/06

See application file for complete search history.

(56) References Cited

U.S. PATENT DOCUMENTS

| | | | |
|---|---|---|---|
| 4,241,184 A * | 12/1980 | Hou ......................... | C12P 7/04 |
| | | | 435/150 |
| 10,093,937 B2 | 10/2018 | Van Maris et al. | |
| 10,689,670 B2 | 6/2020 | Papapetridis et al. | |
| 10,982,195 B2 * | 4/2021 | De Waal .................. | C12P 7/06 |
| 11,186,850 B2 * | 11/2021 | Papapetridis ............. | C12P 7/06 |
| 11,203,741 B2 * | 12/2021 | De Waal ........ | C12Y 101/01072 |
| 11,274,310 B2 * | 3/2022 | De Bruijn ................ | C12P 7/06 |
| 11,384,368 B2 * | 7/2022 | De Waal ........ | C12Y 401/01039 |
| 11,624,057 B2 * | 4/2023 | De Waal ........ | C12Y 207/01028 |
| | | | 435/162 |
| 11,667,886 B2 * | 6/2023 | Papapetridis ........ | C12N 9/0006 |
| | | | 435/255.2 |
| 2008/0085341 A1 | 4/2008 | Dai et al. | |
| 2011/0269180 A1 | 11/2011 | Brat et al. | |
| 2012/0064622 A1 | 3/2012 | Fischer | |
| 2018/0251773 A1 | 9/2018 | Van Maris et al. | |

FOREIGN PATENT DOCUMENTS

| | | |
|---|---|---|
| EP | 2958986 | 12/2015 |
| EP | 3318624 A2 | 5/2018 |
| WO | 2008028019 A1 | 3/2008 |
| WO | 2009013159 A2 | 1/2009 |
| WO | 2009/036095 A1 | 3/2009 |
| WO | 2009062190 A2 | 5/2009 |
| WO | 2010057022 A1 | 5/2010 |
| WO | 2011/006126 A2 | 1/2011 |
| WO | 2011010923 A1 | 1/2011 |
| WO | 2014/129898 A2 | 8/2014 |

OTHER PUBLICATIONS

Brenda Information on xylitol dehydrogenase, obtained from https://www.brenda-enzymes.org/enzyme.php?ecno=1.1.1.B19, Mar. 9, 2022, 3 pages (Year: 2022).*
McKinlay et al., PNAS 107:116699-11675, 2010 (Year: 2010).*
GenBank Database Accession No. AAA99178, Oct. 2011, 2 pages.
UniProt Database Accession No. Q3SFL5, 3 pages (Year: 2013).
UniProt Database Accession No. POA6F7, 2 pages (Year: 2013).
UniProt Database Accession No. POA6G1, 2 pages (Year: 2013).
Milanez et al., Gene 66:55-63, (Year: 1988).
UniProt Database Accession No. P09559, 2 p. (Year: 2013).
Chang et al., J. Biol. Chem. 279:13778-13785, (Year: 2004).
Nissen et al., Met. Engineer. 2:69-77, (Year: 2000).
Letain et al. "Development of a Genetic System for the Chemolithoautotrophic Bacterium Thiobacillus denitrificans", Appl.

(Continued)

*Primary Examiner* — David Steadman

(57) ABSTRACT

The invention relates to a recombinant yeast cell, in particular a transgenic yeast cell, functionally expressing one or more recombinant, in particular heterologous, nucleic acid sequences encoding ribulose-1,5-biphosphate carboxylase oxygenase (Rubisco) and phosphoribulokinase (PRK). The invention further relates to the use of carbon dioxide as an electron acceptor in a recombinant chemotrophic micro-organism, in particular a eukaryotic micro-organism.

28 Claims, 1 Drawing Sheet

Specification includes a Sequence Listing.

(56) References Cited

OTHER PUBLICATIONS

Environ. Microbiol. 73:3265-3271, 2007.
Goloubinoff et al., Nature 337:44-47, 1989.
Chang, H., "Mechanisms of De Novo Multi-domain Protein Folding in Bacteria and Eukaryotes", Dissertation, Ludwig Maximilian University of Munich, 2007.
Mueller-Cajar et al., BioEssays 29:722-724, 2007.
Brandes et al., J. Biol. Chem. 271:6490-6496, 1996.
English et al., FEMS Microbiol. Lett. 94:111-120, 1992.
D3 Excerpt from GenomeQuest filed on Oct. 21, 2019 in EP Patent Application No. 14708109.
Third Party Observation filed Oct. 31, 2017 in EP Patent Application No. 14708109.
Wikipedia.org entry (Atomosphere of Earth) [downloaded on Jan. 17, 2020].
Kerner, Michael J. et al., "Proteome-wide Analysis of Chaperonin-Dependent Protein Folding in *Escherichia coli*", Cell, Jul. 29, 2005, pp. 209-220, vol. 122.
Guo et al., Comp. Struct. Biotechnol. J. 15:161-167, 2017 (Year: 2017).
Zheng Ping et al., "*Escherichia coli* GroE System and GmE-assisted Rubisco Assembly," Progress in Biotechnology, (2000), vol. 20, No. 3: 18-22.
Torben L. Nissen, et al., "Anaerobic and aerobic batch cultivations of Saccharomyces cerevisiae," Yeast, (2000), No. 16: 463-474.
Chinese Office Action relating to Chinese Patent Application No. 201480010133.5 dated May 17, 2017.
Goloubinoff, P., et al., Reconstitution of Active Dimeric Ribulose Bisphospate . . . , Nature, vol. 342, No. 6252, pp. 884-889, 1989.
Tabita, F. R., et al., Function, Structure, and Evolution of the Rubisco-Like . . . , Microbiology and Molecular Biology Reviews 200712 US, vol. 71, No. 4, 2007.

* cited by examiner

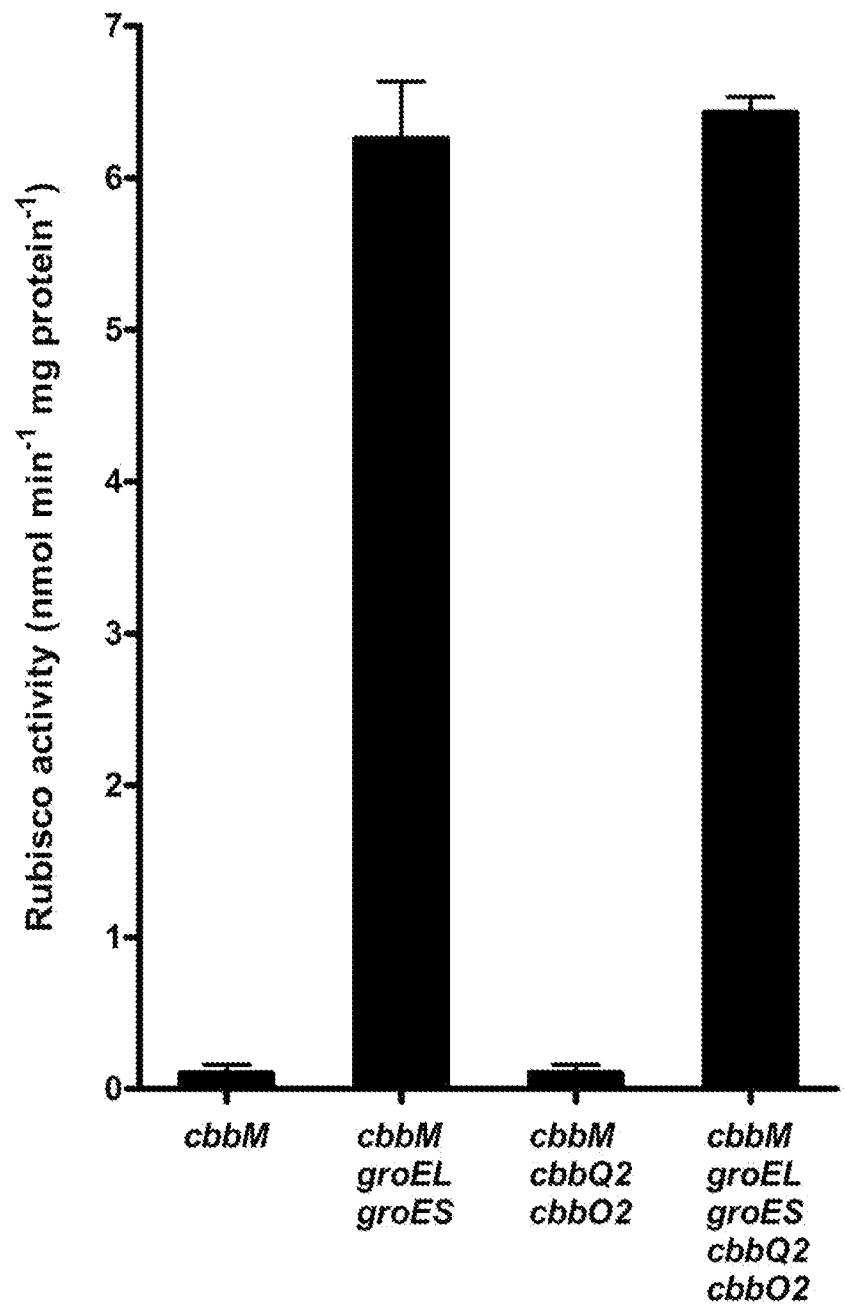

SEQUENCE LISTING

<160> NUMBER OF SEQ ID NOS: 45

<210> SEQ ID NO 1
<211> LENGTH: 1380
<212> TYPE: DNA

<213> ORGANISM: Artificial Sequence
<220> FEATURE:
<223> OTHER INFORMATION: synthetic; based on cbbM gene from Thiobacillus
      denitrificans - pBTWW002, codon optimized
<220> FEATURE:
<221> NAME/KEY: CDS
<222> LOCATION: (1)..(1380)

<400> SEQUENCE: 1

```
atg gat caa tct gca aga tat gct gac ttg tct tta aag gaa gaa gat        48
Met Asp Gln Ser Ala Arg Tyr Ala Asp Leu Ser Leu Lys Glu Glu Asp
1               5                   10                  15 ttg att aaa ggt ggt aga cat att ttg gtt gct tac aaa atg aaa cca        96
Leu Ile Lys Gly Gly Arg His Ile Leu Val Ala Tyr Lys Met Lys Pro
            20                  25                  30 aaa tct ggt tat ggt tat ttg gaa gct gct gct cat ttt gct gct gaa       144
Lys Ser Gly Tyr Gly Tyr Leu Glu Ala Ala Ala His Phe Ala Ala Glu
        35                  40                  45 tct tct aca ggt aca aat gtt gaa gtt tct act aca gat gat ttt aca       192
Ser Ser Thr Gly Thr Asn Val Glu Val Ser Thr Thr Asp Asp Phe Thr
    50                  55                  60 aaa ggt gtt gat gct tta gtt tac tac atc gat gaa gct tca gaa gat       240
Lys Gly Val Asp Ala Leu Val Tyr Tyr Ile Asp Glu Ala Ser Glu Asp
65                  70                  75                  80 atg aga att gct tat cca ttg gaa tta ttc gac aga aat gtt act gac       288
Met Arg Ile Ala Tyr Pro Leu Glu Leu Phe Asp Arg Asn Val Thr Asp
                85                  90                  95 gga aga ttc atg tta gtt tct ttt ttg act ttg gct att ggt aac aat       336
Gly Arg Phe Met Leu Val Ser Phe Leu Thr Leu Ala Ile Gly Asn Asn
            100                 105                 110 caa gga atg gga gat ata gaa cat gca aaa atg ata gat ttt tac gtt       384
Gln Gly Met Gly Asp Ile Glu His Ala Lys Met Ile Asp Phe Tyr Val
        115                 120                 125 cca gaa aga tgt att caa atg ttt gat ggt cca gct aca gat att tct       432
Pro Glu Arg Cys Ile Gln Met Phe Asp Gly Pro Ala Thr Asp Ile Ser
    130                 135                 140 aat ttg tgg aga att ttg ggt aga cca gta gtt aat ggt ggt tat att       480
Asn Leu Trp Arg Ile Leu Gly Arg Pro Val Val Asn Gly Gly Tyr Ile
145                 150                 155                 160 gct ggt act att att aag cca aaa ttg ggt tta aga cca gaa cca ttt       528
Ala Gly Thr Ile Ile Lys Pro Lys Leu Gly Leu Arg Pro Glu Pro Phe
                165                 170                 175 gct aaa gct gct tat caa ttt tgg ttg ggt gga gat ttt atc aag aat       576
Ala Lys Ala Ala Tyr Gln Phe Trp Leu Gly Gly Asp Phe Ile Lys Asn
            180                 185                 190 gac gaa cca caa ggt aat caa gtt ttt tgt cca ttg aaa aaa gtt ttg       624
Asp Glu Pro Gln Gly Asn Gln Val Phe Cys Pro Leu Lys Lys Val Leu
        195                 200                 205 cca ttg gtt tac gat gct atg aaa aga gca caa gat gat act ggt caa       672
Pro Leu Val Tyr Asp Ala Met Lys Arg Ala Gln Asp Asp Thr Gly Gln
    210                 215                 220 gca aaa ttg ttt tct atg aat att act gca gac gat cat tat gaa atg       720
Ala Lys Leu Phe Ser Met Asn Ile Thr Ala Asp Asp His Tyr Glu Met
225                 230                 235                 240 tgt gca aga gct gat tat gct ttg gaa gtt ttc ggt cca gat gca gat       768
Cys Ala Arg Ala Asp Tyr Ala Leu Glu Val Phe Gly Pro Asp Ala Asp
                245                 250                 255 aaa ttg gct ttt ttg gta gat ggt tac gtt gga ggt cca gga atg gtt       816
Lys Leu Ala Phe Leu Val Asp Gly Tyr Val Gly Gly Pro Gly Met Val
            260                 265                 270 act act gct aga agg caa tat cct ggt caa tat ttg cat tat cat aga       864
```

```
Thr Thr Ala Arg Arg Gln Tyr Pro Gly Gln Tyr Leu His Tyr His Arg
        275                 280                 285 gca ggt cac ggt gct gtt act tct cca tct gct aaa aga ggt tat act       912
Ala Gly His Gly Ala Val Thr Ser Pro Ser Ala Lys Arg Gly Tyr Thr
        290                 295                 300 gct ttt gtt ttg gct aaa atg tct aga ttg caa ggc gct tca ggt att       960
Ala Phe Val Leu Ala Lys Met Ser Arg Leu Gln Gly Ala Ser Gly Ile
305                 310                 315                 320 cat gtt ggt act atg ggt tat gga aaa atg gaa gga gaa ggc gac gat      1008
His Val Gly Thr Met Gly Tyr Gly Lys Met Glu Gly Glu Gly Asp Asp
                325                 330                 335 aag att att gct tat atg ata gaa agg gac gaa tgt caa ggt cca gtt      1056
Lys Ile Ile Ala Tyr Met Ile Glu Arg Asp Glu Cys Gln Gly Pro Val
        340                 345                 350 tat ttt caa aaa tgg tac ggt atg aaa cca act act cca att atc tcc      1104
Tyr Phe Gln Lys Trp Tyr Gly Met Lys Pro Thr Thr Pro Ile Ile Ser
        355                 360                 365 gga gga atg aat gct ttg aga ttg cct ggt ttt ttc gaa aat ttg ggt      1152
Gly Gly Met Asn Ala Leu Arg Leu Pro Gly Phe Phe Glu Asn Leu Gly
370                 375                 380 cat ggt aac gtt att aat act gca ggt ggt ggt tct tac ggt cat att      1200
His Gly Asn Val Ile Asn Thr Ala Gly Gly Gly Ser Tyr Gly His Ile
385                 390                 395                 400 gat tct cct gct gct ggt gct att tct ttg aga caa tct tac gaa tgt      1248
Asp Ser Pro Ala Ala Gly Ala Ile Ser Leu Arg Gln Ser Tyr Glu Cys
                405                 410                 415 tgg aaa caa ggt gca gat cca att gaa ttt gct aag gaa cat aag gaa      1296
Trp Lys Gln Gly Ala Asp Pro Ile Glu Phe Ala Lys Glu His Lys Glu
            420                 425                 430 ttt gca aga gct ttt gaa tct ttt cca aaa gat gct gat aag tta ttt      1344
Phe Ala Arg Ala Phe Glu Ser Phe Pro Lys Asp Ala Asp Lys Leu Phe
        435                 440                 445 cca gga tgg aga gaa aaa ttg gga gtt cat tct taa                      1380
Pro Gly Trp Arg Glu Lys Leu Gly Val His Ser
        450                 455

<210> SEQ ID NO 2
<211> LENGTH: 459
<212> TYPE: PRT
<213> ORGANISM: Artificial Sequence
<220> FEATURE:
<223> OTHER INFORMATION: Synthetic Construct

<400> SEQUENCE: 2

Met Asp Gln Ser Ala Arg Tyr Ala Asp Leu Ser Leu Lys Glu Glu Asp
1               5                   10                  15

Leu Ile Lys Gly Gly Arg His Ile Leu Val Ala Tyr Lys Met Lys Pro
            20                  25                  30

Lys Ser Gly Tyr Gly Tyr Leu Glu Ala Ala His Phe Ala Ala Glu
        35                  40                  45

Ser Ser Thr Gly Thr Asn Val Glu Val Ser Thr Thr Asp Asp Phe Thr
    50                  55                  60

Lys Gly Val Asp Ala Leu Val Tyr Tyr Ile Asp Glu Ala Ser Glu Asp
65                  70                  75                  80

Met Arg Ile Ala Tyr Pro Leu Glu Leu Phe Asp Arg Asn Val Thr Asp
                85                  90                  95

Gly Arg Phe Met Leu Val Ser Phe Leu Thr Leu Ala Ile Gly Asn Asn
            100                 105                 110

Gln Gly Met Gly Asp Ile Glu His Ala Lys Met Ile Asp Phe Tyr Val
```

```
                        115                 120                 125
Pro Glu Arg Cys Ile Gln Met Phe Asp Gly Pro Ala Thr Asp Ile Ser
    130                 135                 140

Asn Leu Trp Arg Ile Leu Gly Arg Pro Val Val Asn Gly Gly Tyr Ile
145                 150                 155                 160

Ala Gly Thr Ile Ile Lys Pro Lys Leu Gly Leu Arg Pro Glu Pro Phe
                165                 170                 175

Ala Lys Ala Ala Tyr Gln Phe Trp Leu Gly Gly Asp Phe Ile Lys Asn
            180                 185                 190

Asp Glu Pro Gln Gly Asn Gln Val Phe Cys Pro Leu Lys Lys Val Leu
        195                 200                 205

Pro Leu Val Tyr Asp Ala Met Lys Arg Ala Gln Asp Thr Gly Gln
    210                 215                 220

Ala Lys Leu Phe Ser Met Asn Ile Thr Ala Asp Asp His Tyr Glu Met
225                 230                 235                 240

Cys Ala Arg Ala Asp Tyr Ala Leu Glu Val Phe Gly Pro Asp Ala Asp
                245                 250                 255

Lys Leu Ala Phe Leu Val Asp Gly Tyr Val Gly Gly Pro Gly Met Val
            260                 265                 270

Thr Thr Ala Arg Arg Gln Tyr Pro Gly Gln Tyr Leu His Tyr His Arg
        275                 280                 285

Ala Gly His Gly Ala Val Thr Ser Pro Ser Ala Lys Arg Gly Tyr Thr
    290                 295                 300

Ala Phe Val Leu Ala Lys Met Ser Arg Leu Gln Gly Ala Ser Gly Ile
305                 310                 315                 320

His Val Gly Thr Met Gly Tyr Gly Lys Met Glu Gly Glu Gly Asp Asp
                325                 330                 335

Lys Ile Ile Ala Tyr Met Ile Glu Arg Asp Glu Cys Gln Gly Pro Val
            340                 345                 350

Tyr Phe Gln Lys Trp Tyr Gly Met Lys Pro Thr Thr Pro Ile Ile Ser
        355                 360                 365

Gly Gly Met Asn Ala Leu Arg Leu Pro Gly Phe Phe Glu Asn Leu Gly
    370                 375                 380

His Gly Asn Val Ile Asn Thr Ala Gly Gly Gly Ser Tyr Gly His Ile
385                 390                 395                 400

Asp Ser Pro Ala Ala Gly Ala Ile Ser Leu Arg Gln Ser Tyr Glu Cys
                405                 410                 415

Trp Lys Gln Gly Ala Asp Pro Ile Glu Phe Ala Lys Glu His Lys Glu
            420                 425                 430

Phe Ala Arg Ala Phe Glu Ser Phe Pro Lys Asp Ala Asp Lys Leu Phe
        435                 440                 445

Pro Gly Trp Arg Glu Lys Leu Gly Val His Ser
    450                 455
```

<210> SEQ ID NO 3
<211> LENGTH: 1059
<212> TYPE: DNA
<213> ORGANISM: Spinacia oleracea
<220> FEATURE:
<221> NAME/KEY: CDS
<222> LOCATION: (1)..(1059)

<400> SEQUENCE: 3

```
atg tca caa caa caa aca att gtg att ggt tta gca gca gat tca ggt    48
Met Ser Gln Gln Gln Thr Ile Val Ile Gly Leu Ala Ala Asp Ser Gly
1               5                   10                  15
```

| | | | | | | | | | | | | | | | | |
|---|---|---|---|---|---|---|---|---|---|---|---|---|---|---|---|---|
| tgt | ggt | aag | agt | aca | ttc | atg | agg | agg | tta | aca | agt | gtt | ttc | ggt | ggc | 96 |
| Cys | Gly | Lys | Ser | Thr | Phe | Met | Arg | Arg | Leu | Thr | Ser | Val | Phe | Gly | Gly | |
| | | | 20 | | | | | 25 | | | | | 30 | | | |
| gcg | gcc | gag | cca | cca | aag | ggt | ggt | aac | cca | gat | tca | aac | aca | ttg | att | 144 |
| Ala | Ala | Glu | Pro | Pro | Lys | Gly | Gly | Asn | Pro | Asp | Ser | Asn | Thr | Leu | Ile | |
| | | 35 | | | | | 40 | | | | | 45 | | | | |
| agt | gac | act | act | act | gtt | atc | tgt | ttg | gat | gat | ttt | cat | tcc | ctt | gat | 192 |
| Ser | Asp | Thr | Thr | Thr | Val | Ile | Cys | Leu | Asp | Asp | Phe | His | Ser | Leu | Asp | |
| | 50 | | | | | 55 | | | | | 60 | | | | | |
| aga | aat | ggc | agg | aaa | gtg | gaa | aaa | gtt | act | gct | tta | gac | cca | aaa | gct | 240 |
| Arg | Asn | Gly | Arg | Lys | Val | Glu | Lys | Val | Thr | Ala | Leu | Asp | Pro | Lys | Ala | |
| 65 | | | | | 70 | | | | | 75 | | | | | 80 | |
| aat | gat | ttt | gat | ctt | atg | tat | gaa | caa | gtt | aag | gct | ttg | aaa | gaa | ggt | 288 |
| Asn | Asp | Phe | Asp | Leu | Met | Tyr | Glu | Gln | Val | Lys | Ala | Leu | Lys | Glu | Gly | |
| | | | | 85 | | | | | 90 | | | | | 95 | | |
| aaa | gct | gtt | gat | aaa | cct | att | tat | aat | cat | gtt | tct | ggt | ttg | ttg | gac | 336 |
| Lys | Ala | Val | Asp | Lys | Pro | Ile | Tyr | Asn | His | Val | Ser | Gly | Leu | Leu | Asp | |
| | | | 100 | | | | | 105 | | | | | 110 | | | |
| cct | cct | gag | ctt | att | caa | cct | cct | aag | atc | ttg | gtc | att | gaa | ggg | tta | 384 |
| Pro | Pro | Glu | Leu | Ile | Gln | Pro | Pro | Lys | Ile | Leu | Val | Ile | Glu | Gly | Leu | |
| | | 115 | | | | | 120 | | | | | 125 | | | | |
| cac | ccc | atg | tat | gac | gca | cgt | gtg | agg | gaa | ttg | cta | gac | ttc | agc | atc | 432 |
| His | Pro | Met | Tyr | Asp | Ala | Arg | Val | Arg | Glu | Leu | Leu | Asp | Phe | Ser | Ile | |
| | 130 | | | | | 135 | | | | | 140 | | | | | |
| tac | ttg | gac | att | agc | aat | gaa | gtt | aaa | ttt | gcc | tgg | aaa | att | cag | aga | 480 |
| Tyr | Leu | Asp | Ile | Ser | Asn | Glu | Val | Lys | Phe | Ala | Trp | Lys | Ile | Gln | Arg | |
| 145 | | | | | 150 | | | | | 155 | | | | | 160 | |
| gac | atg | aaa | gaa | aga | gga | cac | agt | ctt | gaa | agc | atc | aaa | gcc | agt | att | 528 |
| Asp | Met | Lys | Glu | Arg | Gly | His | Ser | Leu | Glu | Ser | Ile | Lys | Ala | Ser | Ile | |
| | | | | 165 | | | | | 170 | | | | | 175 | | |
| gaa | tcc | aga | aag | cca | gat | ttt | gat | gct | tac | att | gac | cca | caa | aag | cag | 576 |
| Glu | Ser | Arg | Lys | Pro | Asp | Phe | Asp | Ala | Tyr | Ile | Asp | Pro | Gln | Lys | Gln | |
| | | | 180 | | | | | 185 | | | | | 190 | | | |
| cat | gct | gat | gta | gtg | att | gaa | gta | ttg | cca | act | gaa | ctc | att | cct | gat | 624 |
| His | Ala | Asp | Val | Val | Ile | Glu | Val | Leu | Pro | Thr | Glu | Leu | Ile | Pro | Asp | |
| | | 195 | | | | | 200 | | | | | 205 | | | | |
| gat | gat | gaa | ggc | aaa | gtg | ttg | aga | gta | agg | atg | att | cag | aaa | gaa | gga | 672 |
| Asp | Asp | Glu | Gly | Lys | Val | Leu | Arg | Val | Arg | Met | Ile | Gln | Lys | Glu | Gly | |
| 210 | | | | | 215 | | | | | 220 | | | | | | |
| gtc | aag | ttt | ttc | aac | cca | gtt | tac | ttg | ttt | gat | gaa | gga | tct | acc | att | 720 |
| Val | Lys | Phe | Phe | Asn | Pro | Val | Tyr | Leu | Phe | Asp | Glu | Gly | Ser | Thr | Ile | |
| 225 | | | | | 230 | | | | | 235 | | | | | 240 | |
| tca | tgg | att | cca | tgt | ggt | aga | aaa | tta | aca | tgt | tct | tac | cct | ggt | atc | 768 |
| Ser | Trp | Ile | Pro | Cys | Gly | Arg | Lys | Leu | Thr | Cys | Ser | Tyr | Pro | Gly | Ile | |
| | | | | 245 | | | | | 250 | | | | | 255 | | |
| aaa | ttt | tcc | tat | ggc | cca | gac | acc | ttc | tat | ggc | aac | gag | gtg | aca | gta | 816 |
| Lys | Phe | Ser | Tyr | Gly | Pro | Asp | Thr | Phe | Tyr | Gly | Asn | Glu | Val | Thr | Val | |
| | | | 260 | | | | | 265 | | | | | 270 | | | |
| gta | gag | atg | gat | ggg | atg | ttt | gac | aga | tta | gac | gaa | cta | atc | tac | gtc | 864 |
| Val | Glu | Met | Asp | Gly | Met | Phe | Asp | Arg | Leu | Asp | Glu | Leu | Ile | Tyr | Val | |
| | | 275 | | | | | 280 | | | | | 285 | | | | |
| gaa | agc | cat | ttg | agc | aat | cta | tca | acc | aag | ttt | tat | ggt | gaa | gtc | act | 912 |
| Glu | Ser | His | Leu | Ser | Asn | Leu | Ser | Thr | Lys | Phe | Tyr | Gly | Glu | Val | Thr | |
| | 290 | | | | | 295 | | | | | 300 | | | | | |
| caa | caa | atg | ttg | aag | cac | caa | aat | ttc | cca | gga | agc | aac | aat | gga | act | 960 |
| Gln | Gln | Met | Leu | Lys | His | Gln | Asn | Phe | Pro | Gly | Ser | Asn | Asn | Gly | Thr | |
| 305 | | | | | 310 | | | | | 315 | | | | | 320 | |
| ggt | ttc | ttc | caa | acc | ata | att | gga | ttg | aag | atc | aga | gac | ttg | ttc | gag | 1008 |
| Gly | Phe | Phe | Gln | Thr | Ile | Ile | Gly | Leu | Lys | Ile | Arg | Asp | Leu | Phe | Glu | |

|  |  |  |  |  | 325 |  |  |  |  | 330 |  |  |  |  | 335 |  |  |
|---|---|---|---|---|---|---|---|---|---|---|---|---|---|---|---|---|---|

```
cag ctc gtt gct agc agg tct aca gca act gca aca gct gct aaa gcc    1056
Gln Leu Val Ala Ser Arg Ser Thr Ala Thr Ala Thr Ala Ala Lys Ala
        340                 345                 350 tag                                                                1059
```

<210> SEQ ID NO 4
<211> LENGTH: 352
<212> TYPE: PRT
<213> ORGANISM: Spinacia oleracea

<400> SEQUENCE: 4

Met Ser Gln Gln Gln Thr Ile Val Ile Gly Leu Ala Ala Asp Ser Gly
1               5                   10                  15

Cys Gly Lys Ser Thr Phe Met Arg Arg Leu Thr Ser Val Phe Gly Gly
            20                  25                  30

Ala Ala Glu Pro Pro Lys Gly Gly Asn Pro Asp Ser Asn Thr Leu Ile
        35                  40                  45

Ser Asp Thr Thr Thr Val Ile Cys Leu Asp Asp Phe His Ser Leu Asp
    50                  55                  60

Arg Asn Gly Arg Lys Val Glu Lys Val Thr Ala Leu Asp Pro Lys Ala
65                  70                  75                  80

Asn Asp Phe Asp Leu Met Tyr Glu Gln Val Lys Ala Leu Lys Glu Gly
                85                  90                  95

Lys Ala Val Asp Lys Pro Ile Tyr Asn His Val Ser Gly Leu Leu Asp
            100                 105                 110

Pro Pro Glu Leu Ile Gln Pro Pro Lys Ile Leu Val Ile Glu Gly Leu
        115                 120                 125

His Pro Met Tyr Asp Ala Arg Val Arg Glu Leu Leu Asp Phe Ser Ile
    130                 135                 140

Tyr Leu Asp Ile Ser Asn Glu Val Lys Phe Ala Trp Lys Ile Gln Arg
145                 150                 155                 160

Asp Met Lys Glu Arg Gly His Ser Leu Glu Ser Ile Lys Ala Ser Ile
                165                 170                 175

Glu Ser Arg Lys Pro Asp Phe Asp Ala Tyr Ile Asp Pro Gln Lys Gln
            180                 185                 190

His Ala Asp Val Val Ile Glu Val Leu Pro Thr Glu Leu Ile Pro Asp
        195                 200                 205

Asp Asp Glu Gly Lys Val Leu Arg Val Arg Met Ile Gln Lys Glu Gly
    210                 215                 220

Val Lys Phe Phe Asn Pro Val Tyr Leu Phe Asp Glu Gly Ser Thr Ile
225                 230                 235                 240

Ser Trp Ile Pro Cys Gly Arg Lys Leu Thr Cys Ser Tyr Pro Gly Ile
                245                 250                 255

Lys Phe Ser Tyr Gly Pro Asp Thr Phe Tyr Gly Asn Glu Val Thr Val
            260                 265                 270

Val Glu Met Asp Gly Met Phe Asp Arg Leu Asp Glu Leu Ile Tyr Val
        275                 280                 285

Glu Ser His Leu Ser Asn Leu Ser Thr Lys Phe Tyr Gly Glu Val Thr
    290                 295                 300

Gln Gln Met Leu Lys His Gln Asn Phe Pro Gly Ser Asn Asn Gly Thr
305                 310                 315                 320

Gly Phe Phe Gln Thr Ile Ile Gly Leu Lys Ile Arg Asp Leu Phe Glu
                325                 330                 335

```
                            Gln Leu Val Ala Ser Arg Ser Thr Ala Thr Ala Thr Ala Lys Ala
                                            340                 345                 350

<210> SEQ ID NO 5
<211> LENGTH: 807
<212> TYPE: DNA
<213> ORGANISM: Artificial Sequence
<220> FEATURE:
<223> OTHER INFORMATION: synthetic, based on cbbQ2 gene from
      Thiobacillus denitrificans -codon optimized
<220> FEATURE:
<221> NAME/KEY: CDS
<222> LOCATION: (1)..(807)

<400> SEQUENCE: 5 atg act act aac aag gaa caa tac aag gtt cac caa gaa cca tac tac        48
Met Thr Thr Asn Lys Glu Gln Tyr Lys Val His Gln Glu Pro Tyr Tyr
1               5                   10                  15 caa gct caa ggt aga gaa gtt caa ttg tac gaa gct gct tac aga aac        96
Gln Ala Gln Gly Arg Glu Val Gln Leu Tyr Glu Ala Ala Tyr Arg Asn
                20                  25                  30 aga ttg cca gtt atg gtt aag ggt cca act ggt tgt ggt aag tct aga       144
Arg Leu Pro Val Met Val Lys Gly Pro Thr Gly Cys Gly Lys Ser Arg
            35                  40                  45 ttc gtt gaa tac atg gct tgg aag ttg aac aag cca ttg atc act gtt       192
Phe Val Glu Tyr Met Ala Trp Lys Leu Asn Lys Pro Leu Ile Thr Val
        50                  55                  60 gct tgt aac gaa gac atg act gct tct gac ttg gtt ggt aga tac ttg       240
Ala Cys Asn Glu Asp Met Thr Ala Ser Asp Leu Val Gly Arg Tyr Leu
65                  70                  75                  80 ttg gaa gct aac ggt act aga tgg ttg gac ggt cca ttg act act gct       288
Leu Glu Ala Asn Gly Thr Arg Trp Leu Asp Gly Pro Leu Thr Thr Ala
                85                  90                  95 gct aga atc ggt gct atc tgt tac ttg gac gaa gtt gtt gaa gct aga       336
Ala Arg Ile Gly Ala Ile Cys Tyr Leu Asp Glu Val Val Glu Ala Arg
                100                 105                 110 caa gac act act gtt gtt atc cac cca ttg act gac cac aga aga act       384
Gln Asp Thr Thr Val Val Ile His Pro Leu Thr Asp His Arg Arg Thr
            115                 120                 125 ttg cca ttg gac aag aag ggt gaa ttg atc gaa gct cac cca gac ttc       432
Leu Pro Leu Asp Lys Lys Gly Glu Leu Ile Glu Ala His Pro Asp Phe
        130                 135                 140 caa ttg gtt atc tct tac aac cca ggt tac caa tct ttg atg aag gac       480
Gln Leu Val Ile Ser Tyr Asn Pro Gly Tyr Gln Ser Leu Met Lys Asp
145                 150                 155                 160 ttg aag caa tct act aag caa aga ttc gct gct ttc gac ttc gac tac       528
Leu Lys Gln Ser Thr Lys Gln Arg Phe Ala Ala Phe Asp Phe Asp Tyr
                165                 170                 175 cca gac gct gct ttg gaa act act atc ttg gct aga gaa act ggt ttg       576
Pro Asp Ala Ala Leu Glu Thr Thr Ile Leu Ala Arg Glu Thr Gly Leu
            180                 185                 190 gac gaa act act gct ggt aga ttg gtt aag atc ggt ggt gtt gct aga       624
Asp Glu Thr Thr Ala Gly Arg Leu Val Lys Ile Gly Gly Val Ala Arg
        195                 200                 205 aac ttg aag ggt cac ggt ttg gac gaa ggt atc tct act aga ttg ttg       672
Asn Leu Lys Gly His Gly Leu Asp Glu Gly Ile Ser Thr Arg Leu Leu
    210                 215                 220 gtt tac gct gct act ttg atg aag gac ggt gtt gac gct ggt gac gct       720
Val Tyr Ala Ala Thr Leu Met Lys Asp Gly Val Asp Ala Gly Asp Ala
225                 230                 235                 240 tgt aga atg gct ttg gtt aga cca atc act gac gac gct gac atc aga       768
Cys Arg Met Ala Leu Val Arg Pro Ile Thr Asp Asp Ala Asp Ile Arg
```

```
                       245                 250                 255
gaa act ttg gac cac gct atc gac gct act ttc gct taa              807
Glu Thr Leu Asp His Ala Ile Asp Ala Thr Phe Ala
                260                 265
```

<210> SEQ ID NO 6
<211> LENGTH: 268
<212> TYPE: PRT
<213> ORGANISM: Artificial Sequence
<220> FEATURE:
<223> OTHER INFORMATION: Synthetic Construct

<400> SEQUENCE: 6

```
Met Thr Thr Asn Lys Glu Gln Tyr Lys Val His Gln Glu Pro Tyr Tyr
1               5                   10                  15

Gln Ala Gln Gly Arg Glu Val Gln Leu Tyr Glu Ala Ala Tyr Arg Asn
            20                  25                  30

Arg Leu Pro Val Met Val Lys Gly Pro Thr Gly Cys Gly Lys Ser Arg
        35                  40                  45

Phe Val Glu Tyr Met Ala Trp Lys Leu Asn Lys Pro Leu Ile Thr Val
    50                  55                  60

Ala Cys Asn Glu Asp Met Thr Ala Ser Asp Leu Val Gly Arg Tyr Leu
65                  70                  75                  80

Leu Glu Ala Asn Gly Thr Arg Trp Leu Asp Gly Pro Leu Thr Thr Ala
                85                  90                  95

Ala Arg Ile Gly Ala Ile Cys Tyr Leu Asp Glu Val Val Glu Ala Arg
            100                 105                 110

Gln Asp Thr Thr Val Val Ile His Pro Leu Thr Asp His Arg Arg Thr
        115                 120                 125

Leu Pro Leu Asp Lys Lys Gly Glu Leu Ile Ala His Pro Asp Phe
    130                 135                 140

Gln Leu Val Ile Ser Tyr Asn Pro Gly Tyr Gln Ser Leu Met Lys Asp
145                 150                 155                 160

Leu Lys Gln Ser Thr Lys Gln Arg Phe Ala Ala Phe Asp Phe Asp Tyr
                165                 170                 175

Pro Asp Ala Ala Leu Glu Thr Thr Ile Leu Ala Arg Glu Thr Gly Leu
            180                 185                 190

Asp Glu Thr Thr Ala Gly Arg Leu Val Lys Ile Gly Gly Val Ala Arg
        195                 200                 205

Asn Leu Lys Gly His Gly Leu Asp Glu Gly Ile Ser Thr Arg Leu Leu
    210                 215                 220

Val Tyr Ala Ala Thr Leu Met Lys Asp Gly Val Asp Ala Gly Asp Ala
225                 230                 235                 240

Cys Arg Met Ala Leu Val Arg Pro Ile Thr Asp Asp Ala Asp Ile Arg
                245                 250                 255

Glu Thr Leu Asp His Ala Ile Asp Ala Thr Phe Ala
            260                 265
```

<210> SEQ ID NO 7
<211> LENGTH: 2289
<212> TYPE: DNA
<213> ORGANISM: Artificial Sequence
<220> FEATURE:
<223> OTHER INFORMATION: Synthetic, based on cbbO2 gene from
      Thiobacillus denitrificans -codon optimized
<220> FEATURE:
<221> NAME/KEY: CDS
<222> LOCATION: (1)..(2289)

<400> SEQUENCE: 7

```
atg gct gct tac tgg aag gct ttg gac act aga ttc gct caa gtt gaa      48
Met Ala Ala Tyr Trp Lys Ala Leu Asp Thr Arg Phe Ala Gln Val Glu
1               5                   10                  15 gaa gtt ttc gac gac tgt atg gct gaa gct ttg act gtt ttg tct gct      96
Glu Val Phe Asp Asp Cys Met Ala Glu Ala Leu Thr Val Leu Ser Ala
                20                  25                  30 gaa ggt gtt gct gct tac ttg gaa gct ggt aga gtt atc ggt aag ttg     144
Glu Gly Val Ala Ala Tyr Leu Glu Ala Gly Arg Val Ile Gly Lys Leu
            35                  40                  45 ggt aga ggt gtt gaa cca atg ttg gct ttc ttg gaa gaa tgg cca tct     192
Gly Arg Gly Val Glu Pro Met Leu Ala Phe Leu Glu Glu Trp Pro Ser
 50                  55                  60 act gct caa gct gtt ggt gaa gct gct ttg cca atg gtt atg gct ttg     240
Thr Ala Gln Ala Val Gly Glu Ala Ala Leu Pro Met Val Met Ala Leu
65                  70                  75                  80 atc caa aga atg caa aag tct cca aac ggt aag gct atc gct cca ttc     288
Ile Gln Arg Met Gln Lys Ser Pro Asn Gly Lys Ala Ile Ala Pro Phe
                85                  90                  95 ttg caa act ttg gct cca gtt gct aga aga ttg caa tct gct gaa caa     336
Leu Gln Thr Leu Ala Pro Val Ala Arg Arg Leu Gln Ser Ala Glu Gln
                100                 105                 110 ttg caa cac tac gtt gac gtt act ttg gac ttc atg act aga act act     384
Leu Gln His Tyr Val Asp Val Thr Leu Asp Phe Met Thr Arg Thr Thr
            115                 120                 125 ggt tct atc cac ggt cac cac act act ttc cca tct cca ggt ttg cca     432
Gly Ser Ile His Gly His His Thr Thr Phe Pro Ser Pro Gly Leu Pro
130                 135                 140 gaa ttc ttc gct caa gct cca aac ttg ttg aac caa ttg act ttg gct     480
Glu Phe Phe Ala Gln Ala Pro Asn Leu Leu Asn Gln Leu Thr Leu Ala
145                 150                 155                 160 ggt ttg aga aac tgg gtt gaa tac ggt atc aga aac tac ggt act cac     528
Gly Leu Arg Asn Trp Val Glu Tyr Gly Ile Arg Asn Tyr Gly Thr His
                165                 170                 175 cca gaa aga caa caa gac tac ttc tct ttg caa tct gct gac gct aga     576
Pro Glu Arg Gln Gln Asp Tyr Phe Ser Leu Gln Ser Ala Asp Ala Arg
                180                 185                 190 gct gtt ttg caa aga gaa aga cac ggt act ttg ttg gtt gac gtt gaa     624
Ala Val Leu Gln Arg Glu Arg His Gly Thr Leu Leu Val Asp Val Glu
            195                 200                 205 aga aag ttg gac ttg tac ttg aga ggt ttg tgg caa gac cac gac cac     672
Arg Lys Leu Asp Leu Tyr Leu Arg Gly Leu Trp Gln Asp His Asp His
210                 215                 220 ttg gtt cca tac tct act gct ttc gac gaa atc aga aag cca gtt cca     720
Leu Val Pro Tyr Ser Thr Ala Phe Asp Glu Ile Arg Lys Pro Val Pro
225                 230                 235                 240 tac tac gac aag ttg ggt atg aga ttg cca gac gtt tac gac gac ttg     768
Tyr Tyr Asp Lys Leu Gly Met Arg Leu Pro Asp Val Tyr Asp Asp Leu
                245                 250                 255 gtt ttg cca tgt cca gct ggt aga ggt ggt gct ggt ggt gaa gac gtt     816
Val Leu Pro Cys Pro Ala Gly Arg Gly Gly Ala Gly Gly Glu Asp Val
                260                 265                 270 ttg gtt tct ggt ttg gac aga tac aga gct act ttg gct cac atg gtt     864
Leu Val Ser Gly Leu Asp Arg Tyr Arg Ala Thr Leu Ala His Met Val
            275                 280                 285 ggt cac aga aga tgg tct gaa gct caa atc gct gac aac tgg tct cca     912
Gly His Arg Arg Trp Ser Glu Ala Gln Ile Ala Asp Asn Trp Ser Pro
290                 295                 300 ttc caa aga atg gct gtt gaa ttc ttc gaa gac tgt aga gtt gaa act     960
Phe Gln Arg Met Ala Val Glu Phe Phe Glu Asp Cys Arg Val Glu Thr
```

```
                Phe Gln Arg Met Ala Val Glu Phe Phe Glu Asp Cys Arg Val Glu Thr
                305                 310                 315                 320 ttg ttg atg aga gaa tac cca ggt ttg gct aga atc ttc aga gct ttg        1008
Leu Leu Met Arg Glu Tyr Pro Gly Leu Ala Arg Ile Phe Arg Ala Leu
                325                 330                 335 cac cca aag cca gtt gaa gct gct tgt gac ggt gaa act act tct tgt        1056
His Pro Lys Pro Val Glu Ala Ala Cys Asp Gly Glu Thr Thr Ser Cys
                340                 345                 350 ttg aga cac aga ttg gct atg ttg tct aga gct ttc atc gac cca gac        1104
Leu Arg His Arg Leu Ala Met Leu Ser Arg Ala Phe Ile Asp Pro Asp
                355                 360                 365 cac ggt tac gct gct cca gtt ttg aac gac ttc gtt gct aga ttc cac        1152
His Gly Tyr Ala Ala Pro Val Leu Asn Asp Phe Val Ala Arg Phe His
            370                 375                 380 gct aga ttg gct gac ggt act tct tct act tct gaa atg gct gac ttg        1200
Ala Arg Leu Ala Asp Gly Thr Ser Ser Thr Ser Glu Met Ala Asp Leu
385                 390                 395                 400 gct ttg tct tac gtt gct aag act aga aga cca tct gac caa ttc gct        1248
Ala Leu Ser Tyr Val Ala Lys Thr Arg Arg Pro Ser Asp Gln Phe Ala
                405                 410                 415 aag gtt cac ttc gac gac act gtt gtt gac tac aga gac gac aac aga        1296
Lys Val His Phe Asp Asp Thr Val Val Asp Tyr Arg Asp Asp Asn Arg
                420                 425                 430 caa ttg tgg aag ttc atc gaa gaa ggt gac gaa gaa gaa gct ttc gac        1344
Gln Leu Trp Lys Phe Ile Glu Glu Gly Asp Glu Glu Glu Ala Phe Asp
            435                 440                 445 gct aag aga aag atc gaa cca ggt gaa gaa atc caa ggt ttg cca cca        1392
Ala Lys Arg Lys Ile Glu Pro Gly Glu Glu Ile Gln Gly Leu Pro Pro
450                 455                 460 aga cac tac cca gaa tgg gac tac act tct caa act tac aga cca gac        1440
Arg His Tyr Pro Glu Trp Asp Tyr Thr Ser Gln Thr Tyr Arg Pro Asp
465                 470                 475                 480 tgg gtt tct gtt tac gaa ggt ttg cac aga tct ggt aac gct ggt gac        1488
Trp Val Ser Val Tyr Glu Gly Leu His Arg Ser Gly Asn Ala Gly Asp
                485                 490                 495 atc gac aga ttg ttg gct aag cac gct gct ttg gct aag aga ttg aag        1536
Ile Asp Arg Leu Leu Ala Lys His Ala Ala Leu Ala Lys Arg Leu Lys
                500                 505                 510 aag atg ttg gac ttg ttg aag cca caa gac aag gtt aga gtt aga tac        1584
Lys Met Leu Asp Leu Leu Lys Pro Gln Asp Lys Val Arg Val Arg Tyr
            515                 520                 525 caa gaa gaa ggt tct gaa ttg gac ttg gac gtt gct atc aga tct ttg        1632
Gln Glu Glu Gly Ser Glu Leu Asp Leu Asp Val Ala Ile Arg Ser Leu
                530                 535                 540 atc gac ttc aag ggt ggt gct act cca gac cca aga atc aac atg tct        1680
Ile Asp Phe Lys Gly Gly Ala Thr Pro Asp Pro Arg Ile Asn Met Ser
545                 550                 555                 560 cac aga tct gac ggt aga gac atc gct gtt atg ttg ttg gac ttg           1728
His Arg Ser Asp Gly Arg Asp Ile Ala Val Met Leu Leu Asp Leu
                565                 570                 575 tct gaa tct ttg aac gaa aag gct gct ggt gct ggt caa act atc ttg        1776
Ser Glu Ser Leu Asn Glu Lys Ala Ala Gly Ala Gly Gln Thr Ile Leu
                580                 585                 590 gaa ttg tct caa gaa gct gtt tct ttg ttg gct tgg tct atc gaa aag        1824
Glu Leu Ser Gln Glu Ala Val Ser Leu Leu Ala Trp Ser Ile Glu Lys
                595                 600                 605 ttg ggt gac cca ttc gct atc gct ggt ttc cac tct aac act aga cac        1872
Leu Gly Asp Pro Phe Ala Ile Ala Gly Phe His Ser Asn Thr Arg His
            610                 615                 620
```

| | | |
|---|---|---|
| gac gtt aga tac ttc cac atc aag ggt tac tct gaa aga tgg aac gac<br>Asp Val Arg Tyr Phe His Ile Lys Gly Tyr Ser Glu Arg Trp Asn Asp<br>625                         630                      635                    640 | 1920 |
| gac gtt aag gct aga ttg gct gct atg gaa gct ggt tac tct act aga<br>Asp Val Lys Ala Arg Leu Ala Ala Met Glu Ala Gly Tyr Ser Thr Arg<br>                        645                      650                      655 | 1968 |
| atg ggt gct gct atg aga cac gct gct cac tac ttg tct gct aga cca<br>Met Gly Ala Ala Met Arg His Ala Ala His Tyr Leu Ser Ala Arg Pro<br>                 660                      665                      670 | 2016 |
| gct gac aag aag ttg atg ttg atc ttg act gac ggt aga cca tct gac<br>Ala Asp Lys Lys Leu Met Leu Ile Leu Thr Asp Gly Arg Pro Ser Asp<br>675                         680                      685 | 2064 |
| gtt gac gct gct gac gaa aga ttg ttg gtt gaa gac gct aga caa gct<br>Val Asp Ala Ala Asp Glu Arg Leu Leu Val Glu Asp Ala Arg Gln Ala<br>                 690                      695                      700 | 2112 |
| gtt aag gaa ttg gac aga caa ggt atc ttc gct tac tgt atc tct ttg<br>Val Lys Glu Leu Asp Arg Gln Gly Ile Phe Ala Tyr Cys Ile Ser Leu<br>705                         710                      715                    720 | 2160 |
| gac gct caa ttg aag gct ggt gct gac gac tac gtt gct gaa atc ttc<br>Asp Ala Gln Leu Lys Ala Gly Ala Asp Asp Tyr Val Ala Glu Ile Phe<br>                        725                      730                      735 | 2208 |
| ggt aga caa tac act gtt atc gac aga gtt gaa aga ttg cca gaa aga<br>Gly Arg Gln Tyr Thr Val Ile Asp Arg Val Glu Arg Leu Pro Glu Arg<br>               740                      745                      750 | 2256 |
| ttg cca gaa ttg ttc atg gct ttg act aag taa<br>Leu Pro Glu Leu Phe Met Ala Leu Thr Lys<br>             755                      760 | 2289 |

<210> SEQ ID NO 8
<211> LENGTH: 762
<212> TYPE: PRT
<213> ORGANISM: Artificial Sequence
<220> FEATURE:
<223> OTHER INFORMATION: Synthetic Construct

<400> SEQUENCE: 8

Met Ala Ala Tyr Trp Lys Ala Leu Asp Thr Arg Phe Ala Gln Val Glu
1                 5                    10                  15

Glu Val Phe Asp Asp Cys Met Ala Glu Ala Leu Thr Val Leu Ser Ala
                  20                    25                    30

Glu Gly Val Ala Ala Tyr Leu Glu Ala Gly Arg Val Ile Gly Lys Leu
        35                    40                    45

Gly Arg Gly Val Glu Pro Met Leu Ala Phe Leu Glu Glu Trp Pro Ser
   50                    55                    60

Thr Ala Gln Ala Val Gly Glu Ala Ala Leu Pro Met Val Met Ala Leu
65                   70                    75                    80

Ile Gln Arg Met Gln Lys Ser Pro Asn Gly Lys Ala Ile Ala Pro Phe
                  85                    90                  95

Leu Gln Thr Leu Ala Pro Val Ala Arg Arg Leu Gln Ser Ala Glu Gln
        100                   105                  110

Leu Gln His Tyr Val Asp Val Thr Leu Asp Phe Met Thr Arg Thr Thr
       115                   120                  125

Gly Ser Ile His Gly His His Thr Thr Phe Pro Ser Pro Gly Leu Pro
   130                   135                  140

Glu Phe Phe Ala Gln Ala Pro Asn Leu Leu Asn Gln Leu Thr Leu Ala
145                 150                  155                  160

Gly Leu Arg Asn Trp Val Glu Tyr Gly Ile Arg Asn Tyr Gly Thr His
                 165                   170                  175

```
Pro Glu Arg Gln Gln Asp Tyr Phe Ser Leu Gln Ser Ala Asp Ala Arg
            180                 185                 190

Ala Val Leu Gln Arg Glu Arg His Gly Thr Leu Leu Val Asp Val Glu
            195                 200                 205

Arg Lys Leu Asp Leu Tyr Leu Arg Gly Leu Trp Gln Asp His Asp His
            210                 215                 220

Leu Val Pro Tyr Ser Thr Ala Phe Asp Glu Ile Arg Lys Pro Val Pro
225                 230                 235                 240

Tyr Tyr Asp Lys Leu Gly Met Arg Leu Pro Asp Val Tyr Asp Asp Leu
            245                 250                 255

Val Leu Pro Cys Pro Ala Gly Arg Gly Gly Ala Gly Gly Glu Asp Val
            260                 265                 270

Leu Val Ser Gly Leu Asp Arg Tyr Arg Ala Thr Leu Ala His Met Val
            275                 280                 285

Gly His Arg Arg Trp Ser Glu Ala Gln Ile Ala Asp Asn Trp Ser Pro
            290                 295                 300

Phe Gln Arg Met Ala Val Glu Phe Phe Glu Asp Cys Arg Val Glu Thr
305                 310                 315                 320

Leu Leu Met Arg Glu Tyr Pro Gly Leu Ala Arg Ile Phe Arg Ala Leu
            325                 330                 335

His Pro Lys Pro Val Glu Ala Ala Cys Asp Gly Glu Thr Thr Ser Cys
            340                 345                 350

Leu Arg His Arg Leu Ala Met Leu Ser Arg Ala Phe Ile Asp Pro Asp
            355                 360                 365

His Gly Tyr Ala Ala Pro Val Leu Asn Asp Phe Val Ala Arg Phe His
            370                 375                 380

Ala Arg Leu Ala Asp Gly Thr Ser Ser Thr Ser Glu Met Ala Asp Leu
385                 390                 395                 400

Ala Leu Ser Tyr Val Ala Lys Thr Arg Arg Pro Ser Asp Gln Phe Ala
            405                 410                 415

Lys Val His Phe Asp Asp Thr Val Val Asp Tyr Arg Asp Asp Asn Arg
            420                 425                 430

Gln Leu Trp Lys Phe Ile Glu Glu Gly Asp Glu Glu Ala Phe Asp
            435                 440                 445

Ala Lys Arg Lys Ile Glu Pro Gly Glu Glu Ile Gln Gly Leu Pro Pro
450                 455                 460

Arg His Tyr Pro Glu Trp Asp Tyr Thr Ser Gln Thr Tyr Arg Pro Asp
465                 470                 475                 480

Trp Val Ser Val Tyr Glu Gly Leu His Arg Ser Gly Asn Ala Gly Asp
            485                 490                 495

Ile Asp Arg Leu Leu Ala Lys His Ala Ala Leu Ala Lys Arg Leu Lys
            500                 505                 510

Lys Met Leu Asp Leu Leu Lys Pro Gln Asp Lys Val Arg Val Arg Tyr
            515                 520                 525

Gln Glu Glu Gly Ser Glu Leu Asp Leu Asp Val Ala Ile Arg Ser Leu
            530                 535                 540

Ile Asp Phe Lys Gly Gly Ala Thr Pro Asp Pro Arg Ile Asn Met Ser
545                 550                 555                 560

His Arg Ser Asp Gly Arg Asp Ile Ala Val Met Leu Leu Leu Asp Leu
            565                 570                 575

Ser Glu Ser Leu Asn Glu Lys Ala Ala Gly Ala Gly Gln Thr Ile Leu
            580                 585                 590

Glu Leu Ser Gln Glu Ala Val Ser Leu Leu Ala Trp Ser Ile Glu Lys
```

-continued

```
                595                 600                 605

Leu Gly Asp Pro Phe Ala Ile Ala Gly Phe His Ser Asn Thr Arg His
            610                 615                 620

Asp Val Arg Tyr Phe His Ile Lys Gly Tyr Ser Glu Arg Trp Asn Asp
625                 630                 635                 640

Asp Val Lys Ala Arg Leu Ala Ala Met Glu Ala Gly Tyr Ser Thr Arg
                645                 650                 655

Met Gly Ala Ala Met Arg His Ala Ala His Tyr Leu Ser Ala Arg Pro
            660                 665                 670

Ala Asp Lys Lys Leu Met Leu Ile Leu Thr Asp Gly Arg Pro Ser Asp
        675                 680                 685

Val Asp Ala Ala Asp Glu Arg Leu Leu Val Glu Asp Ala Arg Gln Ala
    690                 695                 700

Val Lys Glu Leu Asp Arg Gln Gly Ile Phe Ala Tyr Cys Ile Ser Leu
705                 710                 715                 720

Asp Ala Gln Leu Lys Ala Gly Ala Asp Asp Tyr Val Ala Glu Ile Phe
                725                 730                 735

Gly Arg Gln Tyr Thr Val Ile Asp Arg Val Glu Arg Leu Pro Glu Arg
            740                 745                 750

Leu Pro Glu Leu Phe Met Ala Leu Thr Lys
        755                 760

<210> SEQ ID NO 9
<211> LENGTH: 1647
<212> TYPE: DNA
<213> ORGANISM: Artificial Sequence
<220> FEATURE:
<223> OTHER INFORMATION: synthetic, based on GroEL from E. coli - codon
      optimized
<220> FEATURE:
<221> NAME/KEY: CDS
<222> LOCATION: (1)..(1647)

<400> SEQUENCE: 9 atg gct gct aag gac gtt aag ttc ggt aac gac gct aga gtt aag atg      48
Met Ala Ala Lys Asp Val Lys Phe Gly Asn Asp Ala Arg Val Lys Met
1               5                   10                  15 ttg aga ggt gtt aac gtt ttg gct gac gct gtt aag gtt act ttg ggt      96
Leu Arg Gly Val Asn Val Leu Ala Asp Ala Val Lys Val Thr Leu Gly
            20                  25                  30 cca aag ggt aga aac gtt gtt ttg gac aag tct ttc ggt gct cca act     144
Pro Lys Gly Arg Asn Val Val Leu Asp Lys Ser Phe Gly Ala Pro Thr
        35                  40                  45 atc act aag gac ggt gtt tct gtt gct aga gaa atc gaa ttg gaa gac     192
Ile Thr Lys Asp Gly Val Ser Val Ala Arg Glu Ile Glu Leu Glu Asp
    50                  55                  60 aag ttc gaa aac atg ggt gct caa atg gtt aag gaa gtt gct tct aag     240
Lys Phe Glu Asn Met Gly Ala Gln Met Val Lys Glu Val Ala Ser Lys
65                  70                  75                  80 gct aac gac gct gct ggt gac ggt act act act gct act gtt ttg gct     288
Ala Asn Asp Ala Ala Gly Asp Gly Thr Thr Thr Ala Thr Val Leu Ala
                85                  90                  95 caa gct atc atc act gaa ggt ttg aag gct gtt gct gct ggt atg aac     336
Gln Ala Ile Ile Thr Glu Gly Leu Lys Ala Val Ala Ala Gly Met Asn
            100                 105                 110 cca atg gac ttg aag aga ggt atc gac aag gct gtt act gct gct gtt     384
Pro Met Asp Leu Lys Arg Gly Ile Asp Lys Ala Val Thr Ala Ala Val
        115                 120                 125 gaa gaa ttg aag gct ttg tct gtt cca tgt tct gac tct aag gct atc     432
```

```
                Glu Glu Leu Lys Ala Leu Ser Val Pro Cys Ser Asp Ser Lys Ala Ile
                            130                 135                 140 gct caa gtt ggt act atc tct gct aac tct gac gaa act gtt ggt aag        480
Ala Gln Val Gly Thr Ile Ser Ala Asn Ser Asp Glu Thr Val Gly Lys
145                 150                 155                 160 ttg atc gct gaa gct atg gac aag gtt ggt aag gaa ggt gtt atc act        528
Leu Ile Ala Glu Ala Met Asp Lys Val Gly Lys Glu Gly Val Ile Thr
                165                 170                 175 gtt gaa gac ggt act ggt ttg caa gac gaa ttg gac gtt gtt gaa ggt        576
Val Glu Asp Gly Thr Gly Leu Gln Asp Glu Leu Asp Val Val Glu Gly
            180                 185                 190 atg caa ttc gac aga ggt tac ttg tct cca tac ttc atc aac aag cca        624
Met Gln Phe Asp Arg Gly Tyr Leu Ser Pro Tyr Phe Ile Asn Lys Pro
                195                 200                 205 gaa act ggt gct gtt gaa ttg gaa tct cca ttc atc ttg ttg gct gac        672
Glu Thr Gly Ala Val Glu Leu Glu Ser Pro Phe Ile Leu Leu Ala Asp
210                 215                 220 aag aag atc tct aac atc aga gaa atg ttg cca gtt ttg gaa gct gtt        720
Lys Lys Ile Ser Asn Ile Arg Glu Met Leu Pro Val Leu Glu Ala Val
225                 230                 235                 240 gct aag gct ggt aag cca ttg ttg atc atc gct gaa gac gtt gaa ggt        768
Ala Lys Ala Gly Lys Pro Leu Leu Ile Ile Ala Glu Asp Val Glu Gly
                245                 250                 255 gaa gct ttg gct act ttg gtt gtt aac act atg aga ggt atc gtt aag        816
Glu Ala Leu Ala Thr Leu Val Val Asn Thr Met Arg Gly Ile Val Lys
            260                 265                 270 gtt gct gct gtt aag gct cca ggt ttc ggt gac aga aga aag gct atg        864
Val Ala Ala Val Lys Ala Pro Gly Phe Gly Asp Arg Arg Lys Ala Met
                275                 280                 285 ttg caa gac atc gct act ttg act ggt ggt act gtt atc tct gaa gaa        912
Leu Gln Asp Ile Ala Thr Leu Thr Gly Gly Thr Val Ile Ser Glu Glu
290                 295                 300 atc ggt atg gaa ttg gaa aag gct act ttg gaa gac ttg ggt caa gct        960
Ile Gly Met Glu Leu Glu Lys Ala Thr Leu Glu Asp Leu Gly Gln Ala
305                 310                 315                 320 aag aga gtt gtt atc aac aag gac act act act atc atc gac ggt gtt       1008
Lys Arg Val Val Ile Asn Lys Asp Thr Thr Thr Ile Ile Asp Gly Val
                325                 330                 335 ggt gaa gaa gct gct atc caa ggt aga gtt gct caa atc aga caa caa       1056
Gly Glu Glu Ala Ala Ile Gln Gly Arg Val Ala Gln Ile Arg Gln Gln
            340                 345                 350 atc gaa gaa gct act tct gac tac gac aga gaa aag ttg caa gaa aga       1104
Ile Glu Glu Ala Thr Ser Asp Tyr Asp Arg Glu Lys Leu Gln Glu Arg
                355                 360                 365 gtt gct aag ttg gct ggt ggt gtt gct gtt atc aag gtt ggt gct gct       1152
Val Ala Lys Leu Ala Gly Gly Val Ala Val Ile Lys Val Gly Ala Ala
370                 375                 380 act gaa gtt gaa atg aag gaa aag aag gct aga gtt gaa gac gct ttg       1200
Thr Glu Val Glu Met Lys Glu Lys Lys Ala Arg Val Glu Asp Ala Leu
385                 390                 395                 400 cac gct act aga gct gct gtt gaa gaa ggt gtt gtt gct ggt ggt ggt       1248
His Ala Thr Arg Ala Ala Val Glu Glu Gly Val Val Ala Gly Gly Gly
                405                 410                 415 gtt gct ttg atc aga gtt gct tct aag ttg gct gac ttg aga ggt caa       1296
Val Ala Leu Ile Arg Val Ala Ser Lys Leu Ala Asp Leu Arg Gly Gln
            420                 425                 430 aac gaa gac caa aac gtt ggt atc aag gtt gct ttg aga gct atg gaa       1344
Asn Glu Asp Gln Asn Val Gly Ile Lys Val Ala Leu Arg Ala Met Glu
                435                 440                 445
```

```
gct cca ttg aga caa atc gtt ttg aac tgt ggt gaa gaa cca tct gtt    1392
Ala Pro Leu Arg Gln Ile Val Leu Asn Cys Gly Glu Glu Pro Ser Val
    450                 455                 460 gtt gct aac act gtt aag ggt ggt gac ggt aac tac ggt tac aac gct    1440
Val Ala Asn Thr Val Lys Gly Gly Asp Gly Asn Tyr Gly Tyr Asn Ala
465                 470                 475                 480 gct act gaa gaa tac ggt aac atg atc gac atg ggt atc ttg gac cca    1488
Ala Thr Glu Glu Tyr Gly Asn Met Ile Asp Met Gly Ile Leu Asp Pro
                485                 490                 495 act aag gtt act aga tct gct ttg caa tac gct gct tct gtt gct ggt    1536
Thr Lys Val Thr Arg Ser Ala Leu Gln Tyr Ala Ala Ser Val Ala Gly
            500                 505                 510 ttg atg atc act act gaa tgt atg gtt act gac ttg cca aag aac gac    1584
Leu Met Ile Thr Thr Glu Cys Met Val Thr Asp Leu Pro Lys Asn Asp
        515                 520                 525 gct gct gac ttg ggt gct gct ggt ggt atg ggt ggt atg ggt ggt atg    1632
Ala Ala Asp Leu Gly Ala Ala Gly Gly Met Gly Gly Met Gly Gly Met
    530                 535                 540 ggt ggt atg atg taa                                                1647
Gly Gly Met Met
545

<210> SEQ ID NO 10
<211> LENGTH: 548
<212> TYPE: PRT
<213> ORGANISM: Artificial Sequence
<220> FEATURE:
<223> OTHER INFORMATION: Synthetic Construct

<400> SEQUENCE: 10

Met Ala Ala Lys Asp Val Lys Phe Gly Asn Asp Ala Arg Val Lys Met
1               5                   10                  15

Leu Arg Gly Val Asn Val Leu Ala Asp Ala Val Lys Val Thr Leu Gly
            20                  25                  30

Pro Lys Gly Arg Asn Val Val Leu Asp Lys Ser Phe Gly Ala Pro Thr
        35                  40                  45

Ile Thr Lys Asp Gly Val Ser Val Ala Arg Glu Ile Glu Leu Glu Asp
    50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Ile Thr Glu Gly Leu Lys Ala Val Ala Ala Gly Met Asn
            100                 105                 110

Pro Met Asp Leu Lys Arg Gly Ile Asp Lys Ala Val Thr Ala Ala Val
        115                 120                 125

Glu Glu Leu Lys Ala Leu Ser Val Pro Cys Ser Asp Ser Lys Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

Val Glu Asp Gly Thr Gly Leu Gln Asp Glu Leu Asp Val Val Glu Gly
            180                 185                 190

Met Gln Phe Asp Arg Gly Tyr Leu Ser Pro Tyr Phe Ile Asn Lys Pro
        195                 200                 205

Glu Thr Gly Ala Val Glu Leu Glu Ser Pro Phe Ile Leu Leu Ala Asp
    210                 215                 220
```

Lys Lys Ile Ser Asn Ile Arg Glu Met Leu Pro Val Leu Glu Ala Val
225                 230                 235                 240

Ala Lys Ala Gly Lys Pro Leu Leu Ile Ile Ala Glu Asp Val Glu Gly
            245                 250                 255

Glu Ala Leu Ala Thr Leu Val Val Asn Thr Met Arg Gly Ile Val Lys
        260                 265                 270

Val Ala Ala Val Lys Ala Pro Gly Phe Gly Asp Arg Arg Lys Ala Met
    275                 280                 285

Leu Gln Asp Ile Ala Thr Leu Thr Gly Gly Thr Val Ile Ser Glu Glu
290                 295                 300

Ile Gly Met Glu Leu Glu Lys Ala Thr Leu Glu Asp Leu Gly Gln Ala
305                 310                 315                 320

Lys Arg Val Val Ile Asn Lys Asp Thr Thr Thr Ile Ile Asp Gly Val
                325                 330                 335

Gly Glu Glu Ala Ala Ile Gln Gly Arg Val Ala Gln Ile Arg Gln Gln
        340                 345                 350

Ile Glu Glu Ala Thr Ser Asp Tyr Asp Arg Glu Lys Leu Gln Glu Arg
    355                 360                 365

Val Ala Lys Leu Ala Gly Gly Val Ala Val Ile Lys Val Gly Ala Ala
370                 375                 380

Thr Glu Val Glu Met Lys Glu Lys Lys Ala Arg Val Glu Asp Ala Leu
385                 390                 395                 400

His Ala Thr Arg Ala Ala Val Glu Glu Gly Val Val Ala Gly Gly Gly
                405                 410                 415

Val Ala Leu Ile Arg Val Ala Ser Lys Leu Ala Asp Leu Arg Gly Gln
        420                 425                 430

Asn Glu Asp Gln Asn Val Gly Ile Lys Val Ala Leu Arg Ala Met Glu
    435                 440                 445

Ala Pro Leu Arg Gln Ile Val Leu Asn Cys Gly Glu Glu Pro Ser Val
450                 455                 460

Val Ala Asn Thr Val Lys Gly Gly Asp Gly Asn Tyr Gly Tyr Asn Ala
465                 470                 475                 480

Ala Thr Glu Glu Tyr Gly Asn Met Ile Asp Met Gly Ile Leu Asp Pro
                485                 490                 495

Thr Lys Val Thr Arg Ser Ala Leu Gln Tyr Ala Ala Ser Val Ala Gly
        500                 505                 510

Leu Met Ile Thr Thr Glu Cys Met Val Thr Asp Leu Pro Lys Asn Asp
    515                 520                 525

Ala Ala Asp Leu Gly Ala Ala Gly Gly Met Gly Gly Met Gly Gly Met
530                 535                 540

Gly Gly Met Met
545

<210> SEQ ID NO 11
<211> LENGTH: 294
<212> TYPE: DNA
<213> ORGANISM: Artificial Sequence
<220> FEATURE:
<223> OTHER INFORMATION: synthetic, based on GroES E. coli - codon
      optimized
<220> FEATURE:
<221> NAME/KEY: CDS
<222> LOCATION: (1)..(294)

<400> SEQUENCE: 11 atg aac atc aga cca ttg cac gac aga gtt atc gtt aag aga aag gaa    48

```
Met Asn Ile Arg Pro Leu His Asp Arg Val Ile Val Lys Arg Lys Glu
1               5                   10                  15 gtt gaa act aag tct gct ggt ggt atc gtt ttg act ggt tct gct gct        96
Val Glu Thr Lys Ser Ala Gly Gly Ile Val Leu Thr Gly Ser Ala Ala
            20                  25                  30 gct aag tct act aga ggt gaa gtt ttg gct gtt ggt aac ggt aga atc       144
Ala Lys Ser Thr Arg Gly Glu Val Leu Ala Val Gly Asn Gly Arg Ile
        35                  40                  45 ttg gaa aac ggt gaa gtt aag cca ttg gac gtt aag gtt ggt gac atc       192
Leu Glu Asn Gly Glu Val Lys Pro Leu Asp Val Lys Val Gly Asp Ile
    50                  55                  60 gtt atc ttc aac gac ggt tac ggt gtt aag tct gaa aag atc gac aac       240
Val Ile Phe Asn Asp Gly Tyr Gly Val Lys Ser Glu Lys Ile Asp Asn
65                  70                  75                  80 gaa gaa gtt ttg atc atg tct gaa tct gac atc ttg gct atc gtt gaa       288
Glu Glu Val Leu Ile Met Ser Glu Ser Asp Ile Leu Ala Ile Val Glu
                85                  90                  95 gct taa                                                                294
Ala

<210> SEQ ID NO 12
<211> LENGTH: 97
<212> TYPE: PRT
<213> ORGANISM: Artificial Sequence
<220> FEATURE:
<223> OTHER INFORMATION: Synthetic Construct

<400> SEQUENCE: 12

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45

Leu Glu Asn Gly Glu Val Lys Pro Leu Asp Val Lys Val Gly Asp Ile
    50                  55                  60

Val Ile Phe Asn Asp Gly Tyr Gly Val Lys Ser Glu Lys Ile Asp Asn
65                  70                  75                  80

Glu Glu Val Leu Ile Met Ser Glu Ser Asp Ile Leu Ala Ile Val Glu
                85                  90                  95

Ala

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
tgacatctag atgtcacaac aacaaacaat tg                                    32

<210> SEQ ID NO 14
<211> LENGTH: 32
<212> TYPE: DNA
<213> ORGANISM: Artificial Sequence
<220> FEATURE:
<223> OTHER INFORMATION: primer

<400> SEQUENCE: 14
tgacatctag atgtcacaac aacaaacaat tg                                    32
```

<210> SEQ ID NO 15
<211> LENGTH: 85
<212> TYPE: DNA
<213> ORGANISM: Artificial Sequence
<220> FEATURE:
<223> OTHER INFORMATION: primer

<400> SEQUENCE: 15
ttgtaaaacg acggccagtg agcgcgcgta atacgactca ctatagggcg aattgggtac    60
agctggagct cagtttatca ttatc    85

<210> SEQ ID NO 16
<211> LENGTH: 81
<212> TYPE: DNA
<213> ORGANISM: Artificial Sequence
<220> FEATURE:
<223> OTHER INFORMATION: primer

<400> SEQUENCE: 16
ggaatctgtg tagtatgcct ggaatgtctg ccgtgccata gccatgtatg ctgatatgtc    60
ggtaccggcc gcaaattaaa g    81

<210> SEQ ID NO 17
<211> LENGTH: 120
<212> TYPE: DNA
<213> ORGANISM: Artificial Sequence
<220> FEATURE:
<223> OTHER INFORMATION: primer

<400> SEQUENCE: 17
atcactctta ccaggctagg acgaccctac tcatgtattg agatcgacga gatttctagg    60
ccagcttttg ttccctttag tgagggttaa ttgcgcgctt ggcgtaatca tggtcatagc    120

<210> SEQ ID NO 18
<211> LENGTH: 120
<212> TYPE: DNA
<213> ORGANISM: Artificial Sequence
<220> FEATURE:
<223> OTHER INFORMATION: primer

<400> SEQUENCE: 18
gacatatcag catacatggc tatggcacgg cagacattcc aggcatacta cacagattcc    60
atcactctta ccaggctagg acgaccctac tcatgtattg agatcgacga gatttctagg    120

<210> SEQ ID NO 19
<211> LENGTH: 119
<212> TYPE: DNA
<213> ORGANISM: Artificial Sequence
<220> FEATURE:
<223> OTHER INFORMATION: primer

<400> SEQUENCE: 19
gttggatcca gtttttaatc tgtcgtcaat cgaaagttta tttcagagtt cttcagactt    60
cttaactcct gtaaaaacaa aaaaaaaaa aggcatagca agctggagct cagtttatc    119

<210> SEQ ID NO 20
<211> LENGTH: 80
<212> TYPE: DNA
<213> ORGANISM: Artificial Sequence
<220> FEATURE:
<223> OTHER INFORMATION: primer

```
<400> SEQUENCE: 20
agatatactg caaagtccgg agcaacagtc gtataactcg agcagccctc tactttgttg    60
ttgcgctaag agaatggacc                                                80

<210> SEQ ID NO 21
<211> LENGTH: 80
<212> TYPE: DNA
<213> ORGANISM: Artificial Sequence
<220> FEATURE:
<223> OTHER INFORMATION: primer

<400> SEQUENCE: 21
gctatgacca tgattacgcc aagcgcgcaa ttaaccctca ctaaagggaa caaaagctgg    60
ttgcgctaag agaatggacc                                                80

<210> SEQ ID NO 22
<211> LENGTH: 81
<212> TYPE: DNA
<213> ORGANISM: Artificial Sequence
<220> FEATURE:
<223> OTHER INFORMATION: primer

<400> SEQUENCE: 22
caacaaagta gagggctgct cgagttatac gactgttgct ccggactttg cagtatatct    60
gctggagctc tagtacggat t                                              81

<210> SEQ ID NO 23
<211> LENGTH: 80
<212> TYPE: DNA
<213> ORGANISM: Artificial Sequence
<220> FEATURE:
<223> OTHER INFORMATION: primer

<400> SEQUENCE: 23
ggaatctgtg tagtatgcct ggaatgtctg ccgtgccata gccatgtatg ctgatatgtc    60
gtaccggccg caaattaaag                                                80

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
gacatatcag catacatggc tatgg                                          25

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
ggacacgctt gacagaatgt caaagg                                         26

<210> SEQ ID NO 26
<211> LENGTH: 21
<212> TYPE: DNA
<213> ORGANISM: Artificial Sequence
<220> FEATURE:
<223> OTHER INFORMATION: primer
```

```
<400> SEQUENCE: 26
cgtccgatat gatctgattg g                                           21

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
cctagaaatc tcgtcgatct c                                           21

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
atcactctta ccaggctagg                                             20

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29 ctggaccttia atcgtgtgcg catcctc                                    27

<210> SEQ ID NO 30
<211> LENGTH: 27
<212> TYPE: DNA
<213> ORGANISM: Artificial Sequence
<220> FEATURE:
<223> OTHER INFORMATION: primer

<400> SEQUENCE: 30
ccgtatagct taatagccag ctttatc                                     27

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
gctatgacca tgattacgcc aagc                                        24

<210> SEQ ID NO 32
<211> LENGTH: 80
<212> TYPE: DNA
<213> ORGANISM: Artificial Sequence
<220> FEATURE:
<223> OTHER INFORMATION: primer

<400> SEQUENCE: 32
ccagcttttg ttccctttag tgagggttaa ttgcgcgctt ggcgtaatca tggtcatagc   60
ctgtgaagat cccagcaaag                                             80
```

<210> SEQ ID NO 33
<211> LENGTH: 120
<212> TYPE: DNA
<213> ORGANISM: Artificial Sequence
<220> FEATURE:
<223> OTHER INFORMATION: primer

<400> SEQUENCE: 33
agctcattga tcccttaaac tttcttttcg gtgtatgact tatgagggtg agaatgcgaa      60
atggcgtgga atgtgatca aaggtaataa aacgtcatat atccgcaggc taaccggaac     120

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ggcgattaag ttgggtaacg      20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
aactgagctc cagctgtacc      20

<210> SEQ ID NO 36
<211> LENGTH: 19
<212> TYPE: DNA
<213> ORGANISM: Artificial Sequence
<220> FEATURE:
<223> OTHER INFORMATION: primer

<400> SEQUENCE: 36
acgcgtgtac gcatgtaac      19

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
gcgcgtggct tcctataatc      20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
gtgaatgctg gtcgctatac      20

<210> SEQ ID NO 39
<211> LENGTH: 20
<212> TYPE: DNA
<213> ORGANISM: Artificial Sequence

```
<220> FEATURE:
<223> OTHER INFORMATION: primer

<400> SEQUENCE: 39
gtaagcagca acaccttcag                                              20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
acctgaccta caggaaagag                                              20

<210> SEQ ID NO 41
<211> LENGTH: 19
<212> TYPE: DNA
<213> ORGANISM: Artificial Sequence
<220> FEATURE:
<223> OTHER INFORMATION: primer

<400> SEQUENCE: 41
tgaagtggta cggcgatgc                                               19

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
atagccaccc aaggcatttc                                              20

<210> SEQ ID NO 43
<211> LENGTH: 19
<212> TYPE: DNA
<213> ORGANISM: Artificial Sequence
<220> FEATURE:
<223> OTHER INFORMATION: primer

<400> SEQUENCE: 43
ccgcactttc tccatgagg                                               19

<210> SEQ ID NO 44
<211> LENGTH: 19
<212> TYPE: DNA
<213> ORGANISM: Artificial Sequence
<220> FEATURE:
<223> OTHER INFORMATION: primer

<400> SEQUENCE: 44
cgacggttac ggtgttaag                                               19

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
cttccggctc ctatgttgtg                                              20
```

RECOMBINANT YEAST EXPRESSING RUBISCO AND PHOSPHORIBULOKINASE

CROSS-REFERENCE TO RELATED APPLICATIONS

This patent application is a continuation patent application of U.S. patent application Ser. No. 15/980,413, filed May 15, 2018 is a continuation patent application of U.S. patent application Ser. No. 14/767,661, filed Aug. 13, 2015, now U.S. Pat. No. 10,093,937, issued Oct. 9, 2018, which is a national phase of International Patent Application No. PCT/NL2014/050106, filed Feb. 21, 2014, which claims the benefit of European Patent Application No. 13156448.6, filed Feb. 22, 2013, the disclosures of each of which is incorporated by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2919208-499002_Sequence_Listing_ST25.txt" created on 18 Nov. 2020, and 66,586 bytes in size) is submitted concurrently with the instant application, and the entire contents of the Sequence Listing are incorporated herein by reference.

FIELD OF THE INVENTION

The invention relates to a recombinant micro-organism having the ability to produce a desired fermentation product, to the functional expression of heterologous peptides in a micro-organism, and to a method for producing a fermentation product wherein said microorganism is used. In a preferred embodiment the micro-organism is a yeast. The invention is further related to a use of $CO_2$ in micro-organisms.

BACKGROUND OF THE INVENTION

Microbial fermentation processes are applied for industrial production of a broad and rapidly expanding range of chemical compounds from renewable carbohydrate feedstocks.

Especially in anaerobic fermentation processes, redox balancing of the cofactor couple $NADH/NAD^+$ can cause important constraints on product yields. This challenge is exemplified by the formation of glycerol as major by-product in the industrial production of—for instance—fuel ethanol by *Saccharomyces cerevisiae*, a direct consequence of the need to reoxidize NADH formed in biosynthetic reactions.

Ethanol production by *Saccharomyces cerevisiae* is currently, by volume, the single largest fermentation process in industrial biotechnology, but various other compounds, including other alcohols, carboxylic acids, isoprenoids, amino acids etc, are currently produced in industrial biotechnological processes.

Various approaches have been proposed to improve the fermentative properties of organisms used in industrial biotechnology by genetic modification.

WO 2008/028019 relates to a method for forming fermentation products utilizing a microorganism having at least one heterologous gene sequence, the method comprising the steps of converting at least one carbohydrate to 3-phosphoglycerate and fixing carbon dioxide, wherein at least one of said steps is catalyzed by at least one exogenous enzyme. Further, it relates to a microorganism for forming fermentation products of at least one sugar, the microorganism comprising at least one heterologous gene sequence encoding at least one enzyme selected from the group consisting of phosphopentose epimerase, phosphoribulokinase, and ribulose bisphosphate carboxylase.

In an example, a yeast is mentioned wherein a heterologous PRK and a heterologous Rubisco gene are incorporated. In an embodiment the yeast is used for ethanol production. The results (FIG. 24) show concentrations for transgenic controls and the modified strains. Little difference is noticeable between modified yeast and its corresponding control. No information is apparent regarding product yield, sugar conversion, yeast growth, evaporation rates of ethanol. Thus, it is apparent that results are not conclusive with respect to an improvement in ethanol yield.

Further, WO 2008/028019 is silent on the problem of glycerol side-product formation.

A major challenge relating to the stoichiometry of yeast-based production of ethanol, but also of other compounds, is that substantial amounts of NADH-dependent side-products (in particular glycerol) are generally formed as a by-product, especially under anaerobic and oxygen-limited conditions or under conditions where respiration is otherwise constrained or absent. It has been estimated that, in typical industrial ethanol processes, up to about 4 wt. % of the sugar feedstock is converted into glycerol (Nissen et al. Yeast 16 (2000) 463-474). Under conditions that are ideal for anaerobic growth, the conversion into glycerol may even be higher, up to about 10%.

Glycerol production under anaerobic conditions is primarily linked to redox metabolism. During anaerobic growth of *S. cerevisiae*, sugar dissimilation occurs via alcoholic fermentation. In this process, the NADH formed in the glycolytic glyceraldehyde-3-phosphate dehydrogenase reaction is reoxidized by converting acetaldehyde, formed by decarboxylation of pyruvate to ethanol via $NAD^+$-dependent alcohol dehydrogenase. The fixed stoichiometry of this redox-neutral dissimilatory pathway causes problems when a net reduction of $NAD^+$ to NADH occurs elsewhere in metabolism. Under anaerobic conditions, NADH reoxidation in *S. cerevisiae* is strictly dependent on reduction of sugar to glycerol. Glycerol formation is initiated by reduction of the glycolytic intermediate dihydroxyacetone phosphate (DHAP) to glycerol 3-phosphate (glycerol-3P), a reaction catalyzed by $NAD^+$-dependent glycerol 3-phosphate dehydrogenase. Subsequently, the glycerol 3-phosphate formed in this reaction is hydrolysed by glycerol-3-phosphatase to yield glycerol and inorganic phosphate. Consequently, glycerol is a major by-product during anaerobic production of ethanol by *S. cerevisiae*, which is undesired as it reduces overall conversion of sugar to ethanol. Further, the presence of glycerol in effluents of ethanol production plants may impose costs for waste-water treatment.

In WO 2011/010923, the NADH-related side-product (glycerol) formation in a process for the production of ethanol from a carbohydrate containing feedstock—in particular a carbohydrate feedstock derived from lignocellulosic biomass-glycerol side-production problem is addressed by providing a recombinant yeast cell comprising one or more recombinant nucleic acid sequences encoding an $NAD^+$-dependent acetylating acetaldehyde dehydrogenase (EC 1.2.1.10) activity, said cell either lacking enzymatic activity needed for the NADH-dependent glycerol synthesis or the cell having a reduced enzymatic activity with respect to the NADH-dependent glycerol synthesis compared to its corresponding wild-type yeast cell. A cell is described that is effective in essentially eliminating glycerol production. Also, the cell uses acetate to reoxidise NADH, whereby ethanol yield can be increased if an acetate-containing feedstock is used.

Although the described process in WO 2011/010923 is advantageous, there is a continuing need for alternatives, in particular alternatives that also allow the production of a useful organic compound, such as ethanol, without needing acetate or other organic electron acceptor molecules in order to eliminate or at least reduce NADH-dependent side-product synthesis. It would in particular be desirable to provide a microorganism wherein NADH-dependent side-product synthesis is reduced and which allows increased product yield, also in the absence of acetate.

The inventors realised that it may be possible to reduce or even eliminate NADH-dependent side-product synthesis by functionally expressing a recombinant enzyme in a heterotrophic, chemotrophic microorganism cell, in particular a yeast cell, using carbon dioxide as a substrate.

SUMMARY OF THE INVENTION

Accordingly, the present invention relates to the use of carbon dioxide as an electron acceptor in a recombinant chemoheterotrophic micro-organism, in particular a eukaryotic micro-organism. Chemotrophic, (chemo)heterotrophic and autotrophic and other classifications of a microorganism are herein related to the micro-organism before recombination, this organism is herein also referred to as the host. For instance, through recombination as disclosed herein a host micro-organism that is originally (chemo)heterotroph and not autotrophic may become autotrophic after recombination, since applying what is disclosed herein causes that the recombined organism may assimilate carbon dioxide, thus resulting in (partial) (chemo)autotrophy.

Advantageously, the inventors have found a way to incorporate the carbon dioxide as a co-substrate in metabolic engineering of heterotrophic industrial microorganisms that can be used to improve product yields and/or to reduce side-product formation.

In particular, the inventors found it to be possible to reduce or even eliminate NADH-dependent side-product synthesis by functionally expressing at least two recombinant enzyme from two specific groups in a eukaryotic microorganism, in particular a yeast cell, wherein one of the enzymes catalysis a reaction wherein carbon dioxide is used and the other uses ATP as a cofactor.

Accordingly, the invention further relates to a recombinant, in a particular transgenic, eukaryotic microorganism, in particular a yeast cell, said microorganism functionally expressing one or more recombinant, in particular heterologous, nucleic acid sequences encoding a ribulose-1,5-biphosphate carboxylase oxygenase (Rubisco) and a phosphoribulokinase (PRK).

BRIEF DESCRIPTION OF THE DRAWING

FIG. 1 is a graph showing comparative results for Rubisco activity in cell extracts described in Example 5.

DETAILED DESCRIPTION OF THE INVENTION

A microorganism according to the invention has in particular been found advantageous in that in the presence of Rubisco and the PRK NADH-dependent side-product formation (glycerol) is reduced considerably or essentially completely eliminated and production of the desired product can be increased. It is thought that the carbon dioxide acts as an electron acceptor for NADH whereby less NADH is available for the reaction towards the side-product (such as glycerol).

The invention further relates to a method for preparing an organic compound, in particular an alcohol, organic acid or amino acid, comprising converting a carbon source, in particular a carbohydrate or another organic carbon source using a microorganism, thereby forming the organic compound, wherein the microorganism is a microorganism according to the invention or wherein carbon dioxide is used as an electron acceptor in a recombinant chemotrophic or chemoheterotrophic micro-organism.

The invention further relates to a vector for the functional expression of a heterologous polypeptide in a yeast cell, wherein said vector comprises a heterologous nucleic acid sequence encoding Rubisco and PRK, wherein said Rubisco exhibits activity of carbon fixation. The term "a" or "an" as used herein is defined as "at least one" unless specified otherwise.

When referring to a noun (e.g. a compound, an additive, etc.) in the singular, the plural is meant to be included. Thus, when referring to a specific moiety, e.g. "compound", this means "at least one" of that moiety, e.g. "at least one compound", unless specified otherwise.

The term 'or' as used herein is to be understood as 'and/or'.

When referring to a compound of which several isomers exist (e.g. a D and an L enantiomer), the compound in principle includes all enantiomers, diastereomers and cis/trans isomers of that compound that may be used in the particular method of the invention; in particular when referring to such as compound, it includes the natural isomer(s).

For the purpose of clarity and a concise description features are described herein as part of the same or separate embodiments, however, it will be appreciated that the scope of the invention may include embodiments having combinations of all or some of the features described". In view of this passage it is evident to the skilled reader that the variants of claim 1 as filed may be combined with other features described in the application as filed, in particular with features disclosed in the dependent claims, such claims usually relating to the most preferred embodiments of an invention.

The term 'fermentation', 'fermentative' and the like is used herein in a classical sense, i.e. to indicate that a process is or has been carried out under anaerobic conditions. Anaerobic conditions are herein defined as conditions without any oxygen or in which essentially no oxygen is consumed by the yeast cell, in particular a yeast cell, and usually corresponds to an oxygen consumption of less than 5 mmol/l·h, in particular to an oxygen consumption of less than 2.5 mmol/l·h, or less than 1 mmol/l·h. More preferably 0 mmol/L/h is consumed (i.e. oxygen consumption is not detectable). This usually corresponds to a dissolved oxygen concentration in the culture broth of less than 5% of air saturation, in particular to a dissolved oxygen concentration of less than 1% of air saturation, or less than 0.2% of air saturation.

The term "yeast" or "yeast cell" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well known species.

The term "recombinant (cell)" or "recombinant microorganism" as used herein, refers to a strain (cell) containing nucleic acid which is the result of one or more genetic modifications using recombinant DNA technique(s) and/or another mutagenic technique(s). In particular a recombinant cell may comprise nucleic acid not present in a corresponding wild-type cell, which nucleic acid has been introduced into that strain (cell) using recombinant DNA techniques (a transgenic cell), or which nucleic acid not present in said wild-type is the result of one or more mutations—for example using recombinant DNA techniques or another mutagenesis technique such as UV-irradiation—in a nucleic acid sequence present in said wild-type (such as a gene encoding a wild-type polypeptide) or wherein the nucleic acid sequence of a gene has been modified to target the polypeptide product (encoding it) towards another cellular compartment. Further, the term "recombinant (cell)" in particular relates to a strain (cell) from which DNA sequences have been removed using recombinant DNA techniques.

The term "transgenic (yeast) cell" as used herein, refers to a strain (cell) containing nucleic acid not naturally occurring in that strain (cell) and which has been introduced into that strain (cell) using recombinant DNA techniques, i.e. a recombinant cell).

The term "mutated" as used herein regarding proteins or polypeptides means that at least one amino acid in the wild-type or naturally occurring protein or polypeptide sequence has been replaced with a different amino acid, inserted or deleted from the sequence via mutagenesis of nucleic acids encoding these amino acids. Mutagenesis is a well-known method in the art, and includes, for example, site-directed mutagenesis by means of PCR or via oligo-nucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleic acid sequence of that gene or a regulatory sequence thereof, has been replaced with a different nucleotide, or has been deleted from the sequence via mutagenesis, resulting in the transcription of a protein sequence with a qualitatively of quantitatively altered function or the knock-out of that gene.

The term "gene", as used herein, refers to a nucleic acid sequence containing a template for a nucleic acid polymerase, in eukaryotes, RNA polymerase II. Genes are transcribed into mRNAs that are then translated into protein.

The term "nucleic acid" as used herein, includes reference to a deoxyribonucleotide or ribonucleotide polymer, i.e. a polynucleotide, in either single or double-stranded form, and unless otherwise limited, encompasses known analogues having the essential nature of natural nucleotides in that they hybridize to single-stranded nucleic acids in a manner similar to naturally occurring nucleotides (e. g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

When an enzyme is mentioned with reference to an enzyme class (EC), the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at the NC-IUBMB website chem.qmul.ac.uk/iubmb/enzyme. Other suitable enzymes that have not (yet) been classified in a specified class but may be classified as such, are meant to be included.

If referred herein to a protein or a nucleic acid sequence, such as a gene, by reference to a accession number, this number in particular is used to refer to a protein or nucleic acid sequence (gene) having a sequence as can be found at the National Center for Biotechnology Information (NCBI-NIH) website ncbi.nlm.nih.gov unless specified otherwise.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations" and represent one species of conservatively modified variation.

The term "functional homologue" (or in short "homologue") of a polypeptide having a specific sequence (e.g. SEQ ID NO: X), as used herein, refers to a polypeptide comprising said specific sequence with the proviso that one or more amino acids are substituted, deleted, added, and/or inserted, and which polypeptide has (qualitatively) the same enzymatic functionality for substrate conversion. This functionality may be tested by use of an assay system comprising a recombinant yeast cell comprising an expression vector for the expression of the homologue in yeast, said expression vector comprising a heterologous nucleic acid sequence operably linked to a promoter functional in the yeast and said heterologous nucleic acid sequence encoding the homologous polypeptide of which enzymatic activity for converting acetyl-Coenzyme A to acetaldehyde in the yeast cell is to be tested, and assessing whether said conversion occurs in said cells. Candidate homologues may be identified by using in silico similarity analyses. A detailed example of such an analysis is described in Example 2 of WO2009/013159. The skilled person will be able to derive there from how suitable candidate homologues may be found and, optionally upon codon (pair) optimization, will be able to test the required functionality of such candidate homologues using a suitable assay system as described above. A suitable homologue represents a polypeptide having an amino acid sequence similar to a specific polypeptide of more than 50%, preferably of 60% or more, in particular of at least 70%, more in particular of at least 80%, at least 90%, at least 95%, at least 97%, at least 98% or at least 99% and having the required enzymatic functionality. With respect to nucleic acid sequences, the term functional homologue is meant to include nucleic acid sequences which differ from another nucleic acid sequence due to the degeneracy of the genetic code and encode the same polypeptide sequence.

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively. Although disputed, to indicate "percent identity" or "percent similarity", "level of homology" or "percent homology" are frequently used interchangeably. A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss-.bioinformatics.nl). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

Global Homology Definition

The homology or identity is the percentage of identical matches between the two full sequences over the total aligned region including any gaps or extensions. The homology or identity between the two aligned sequences is calculated as follows: Number of corresponding positions in the alignment showing an identical amino acid in both sequences divided by the total length of the alignment including the gaps. The identity defined as herein can be obtained from NEEDLE and is labelled in the output of the program as "IDENTITY".

Longest Identity Definition

The homology or identity between the two aligned sequences is calculated as follows: Number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labeled in the output of the program as "longest-identity".

A variant of a nucleotide or amino acid sequence disclosed herein may also be defined as a nucleotide or amino acid sequence having one or several substitutions, insertions and/or deletions as compared to the nucleotide or amino acid sequence specifically disclosed herein (e.g. in de the sequence listing).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asp aragine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Nucleotide sequences of the invention may also be defined by their capability to hybridise with parts of specific nucleotide sequences disclosed herein, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in eukaryotic host cell systems such as yeast are well known to those of skill in the art. A polynucleotide comprising a nucleic acid sequence of a gene encoding an enzyme with a specific activity can be expressed in such a eukaryotic system. In some embodiments, transformed/transfected yeast cells may be employed as expression systems for the expression of the enzymes. Expression of heterologous proteins in yeast is well known. Sherman, F., et al., Methods in Yeast Genetics, Cold Spring Harbor Laboratory (1982) is a well recognized work describing the various methods available to express proteins in yeast. Two widely utilized yeasts are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. If a promoter is an inducible promoter, then the rate of transcription increases in response to an inducing agent.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleic acid sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are eukaryotic cells of the order of Actinomycetales.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

The microorganism, preferably is selected from the group of Saccharomycetaceae, such as *Saccharomyces cerevisiae, Saccharomyces pastorianus, Saccharomyces beticus, Saccharomyces fermentati, Saccharomyces paradoxus, Saccharomyces uvarum* and *Saccharomyces bayanus; Schizosaccharomyces* such as *Schizosaccharomyces pombe, Schizosaccharomyces japonicus, Schizosaccharomyces octosporus* and *Schizosaccharomyces cryophilus; Toru-*

*laspora* such as *Torulaspora delbrueckii*; *Kluyveromyces* such as *Kluyveromyces marxianus*; *Pichia* such as *Pichia stipitis*, *Pichia pastoris* or *pichia angusta*, *Zygosaccharomyces* such as *Zygosaccharomyces bailii*; *Brettanomyces* such as *Brettanomyces intermedius*, *Brettanomyces bruxellensis*, *Brettanomyces anomalus*, *Brettanomyces custersianus*, *Brettanomyces naardenensis*, *Brettanomyces nanus*, *Dekkera bruxellensis* and *Dekkera anomala*; *Metschnikowia*, *Issatchenkia*, such as *Issatchenkia orientalis*, *Kloeckera* such as *Kloeckera apiculata*; *Aureobasidium* such as *Aureobasidium pullulans*.

In a highly preferred embodiment, the microorganism is a yeast cell is selected from the group of Saccharomycetaceae. In particular, good results have been achieved with a *Saccharomyces cerevisiae* cell. It has been found possible to use such a cell according to the invention in a method for preparing an alcohol (ethanol) wherein the NADH-dependent side-product formation (glycerol) was reduced by about 90%, and wherein the yield of the desired product (ethanol) was increase by about 10%, compared to a similar cell without Rubisco and PRK.

The Rubisco may in principle be selected from eukaryotic and prokaryotic Rubisco's.

The Rubisco is preferably from a non-phototrophic organism. In particular, the Rubisco may be from a chemolithoautotrophic microorganism.

Good results have been achieved with a bacterial Rubisco. Preferably, the bacterial Rubisco originates from a *Thiobacillus*, in particular, *Thiobacillus denitrificans*, which is chemolithoautotrophic.

The Rubisco may be a single-subunit Rubisco or a Rubisco having more than one subunit. In particular, good results have been achieved with a single-subunit Rubisco.

In particular, good results have been achieved with a form-II Rubisco, more in particular CbbM.

SEQUENCE ID NO: 2 shows the sequence of a particularly preferred Rubisco in accordance with the invention. It is encoded by the cbbM gene from *Thiobacillus denitrificans*. A preferred alternative to this Rubisco, is a functional homologue of this Rubisco, in particular such functional homologue comprising a sequence having at least 80%, 85%, 90% or 95% sequence identity with SEQUENCE ID NO: 2. Suitable natural Rubisco polypeptides are given in Table 1.

TABLE 1

Rubisco polypeptides

| Source | Accession no. | MAX ID (%) |
|---|---|---|
| *Thiobacillus denitrificans* | AAA99178.2 | 100 |
| *Sideroxydans lithotrophicus* ES-1 | YP_003522651.1 | 94 |
| *Thiothrix nivea* DSM 5205 | ZP_10101642.1 | 91 |
| *Halothiobacillus neapolitanus* c2 | YP_003262978.1 | 90 |
| *Acidithiobacillus ferrooxidans* ATCC 53993 | YP_002220242.1 | 88 |
| *Rhodoferax ferrireducens* T118 | YP_522655.1 | 86 |
| *Thiorhodococcus drewsii* AZ1 | ZP_08824342.1 | 85 |
| uncultured prokaryote | AGE14067.1 | 82 |

In accordance with the invention, the Rubisco is functionally expressed in the microorganism, at least during use in an industrial process for preparing a compound of interest.

To increase the likelihood that herein enzyme activity is expressed at sufficient levels and in active form in the transformed (recombinant) host cells of the invention, the nucleotide sequence encoding these enzymes, as well as the Rubisco enzyme and other enzymes of the invention (see below), are preferably adapted to optimise their codon usage to that of the host cell in question. The adaptiveness of a nucleotide sequence encoding an enzyme to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences which have been codon optimised for expression in the fungal host cell in question such as e.g. *S. cerevisiae* cells.

Preferably, the functionally expressed Rubisco has an activity, defined by the rate of ribulose-1,5-bisphosphate-dependent $^{14}$C-bicarbonate incorporation by cell extracts of at least 1 nmol·min$^{-1}$·(mg protein)$^{-1}$, in particular an activity of at least 2 nmol·min$^{-1}$·(mg protein)$^{-1}$, more in particular an activity of at least 4 nmol·min$^{-1}$·(mg protein)$^{-1}$. The upper limit for the activity is not critical. In practice, the activity may be about 200 nmol·min$^{-1}$·(mg protein)$^{-1}$ or less, in particular 25 nmol·min$^{-1}$·(mg protein)$^{-1}$, more in particular 15 nmol·min$^{-1}$·(mg protein)$^{-1}$ or less, e.g. about 10 nmol·min$^{-1}$·(mg protein)$^{-1}$ or less. When referred herein to the activity of Rubisco, in particular the activity at 30° C. is meant. The conditions for an assay for determining this Rubisco activity are as found in the Examples, below (Example 4).

A functionally expressed phosphoribulokinase (PRK, (EC 2.7.1.19)) according to the invention is capable of catalysing the chemical reaction:

$$\text{ATP} + \text{D-ribulose 5-phosphate} \rightleftharpoons \text{ADP} + \text{D-ribulose 1,5-bisphosphate} \qquad (1)$$

Thus, the two substrates of this enzyme are ATP and D-ribulose 5-phosphate, whereas its two products are ADP and D-ribulose 1,5-bisphosphate.

PRK belongs to the family of transferases, specifically those transferring phosphorus-containing groups (phosphotransferases) with an alcohol group as acceptor. The systematic name of this enzyme class is ATP:D-ribulose-5-phosphate 1-phosphotransferase. Other names in common use include phosphopentokinase, ribulose-5-phosphate kinase, phosphopentokinase, phosphoribulokinase (phosphorylating), 5-phosphoribulose kinase, ribulose phosphate kinase, PKK, PRuK, and PRK. This enzyme participates in carbon fixation.

The PRK can be from a prokaryote or a eukaryote. Good results have been achieved with a PRK originating from a eukaryote. Preferably the eukaryotic PRK originates from a plant selected from Caryophyllales, in particular from Amaranthaceae, more in particular from *Spinacia*.

As a preferred alternative to PRK from *Spinacia* a functional homologue of PRK from *Spinacia* may be present, in particular a functional homologue comprising a sequence having at least 70%, 75%, 80%, 85%, 90% or 95% sequence identity with SEQUENCE ID NO 4.

Suitable natural PRK polypeptides are given in Table 2.

TABLE 2

Natural PRK polypeptides suitable for expression

| Source | Accession no. | MAX ID (%) |
|---|---|---|
| Spinacia oleracea | P09559.1 | 100 |
| Medicago truncatula | XP_003612664.1 | 88 |
| Arabidopsis thaliana | NP_174486.1 | 87 |
| Vitis vinifera | XP_002263724.1 | 86 |
| Closterium peracerosum | BAL03266.1 | 82 |
| Zea mays | NP_001148258.1 | 78 |

In an advantageous embodiment, the recombinant microorganism further comprises a nucleic acid sequence encoding one or more heterologous prokaryotic or eukaryotic molecular chaperones, which—when expressed—are capable of functionally interacting with an enzyme in the microorganism, in particular with at least one of Rubisco and PRK.

Chaperonins are proteins that provide favourable conditions for the correct folding of other proteins, thus preventing aggregation. Newly made proteins usually must fold from a linear chain of amino acids into a three-dimensional form. Chaperonins belong to a large class of molecules that assist protein folding, called molecular chaperones. The energy to fold proteins is supplied by adenosine triphosphate (ATP). A review article about chaperones that is useful herein is written by Yebenes (2001); "Chaperonins: two rings for folding"; Hugo Yebenes et al. Trends in Biochemical Sciences, August 2011, Vol. 36, No. 8.

In a preferred embodiment, the chaperone or chaperones are from a bacterium, more preferably from *Escherichia*, in particular *E. coli* GroEL and GroEs from *E. coli* may in particular be encoded in a microorganism according to the invention. Other preferred chaperones are chaperones from *Saccharomyces*, in particular *Saccharomyces cerevisiae* Hsp10 and Hsp60. If the chaperones are naturally expressed in an organelle such as a mitochondrion (examples are Hsp60 and Hsp10 of *Saccharomyces cerevisiae*) relocation to the cytosol can be achieved e.g. by modifying the native signal sequence of the chaperonins.

In eukaryotes the proteins Hsp60 and Hsp10 are structurally and functionally nearly identical to GroEL and GroES, respectively. Thus, it is contemplated that Hsp60 and Hsp10 from any eukaryotic cell may serve as a chaperone for the Rubisco. See Zeilstra-Ryalls J, Fayet O, Georgopoulos C (1991). "The universally conserved GroE (Hsp60) chaperonins" Annu Rev Microbiol. 45: 301-25. doi:10.1146/annurev.mi.45.100191.001505. PMID 1683763 and Horwich A L, Fenton W A, Chapman E, Farr G W (2007). "Two Families of Chaperonin: Physiology and Mechanism". Annu Rev Cell Dev Biol. 23: 115-45. doi:10.1146/annurev.cellbio.23.090506.123555. PMID 17489689.

Particularly good results have been achieved with a recombinant yeast cell comprising both the heterologous chaperones GroEL and GroES.

As a preferred alternative to GroEL a functional homologue of GroEL may be present, in particular a functional homologue comprising a sequence having at least 70%, 75%, 80%, 85%, 90% or 95% sequence identity with SEQUENCE ID NO: 10.

Suitable natural chaperones polypeptide homologous to SEQUENCE ID NO: 10 are given in Table 3.

TABLE 3

Natural chaperones homologous to SEQUENCE ID NO: 10 polypeptides suitable for expression >gi | 115388105 | ref | XP_001211558.1 | :2-101 10 kDa heat shock protein, mitochondrial [*Aspergillus terreus* NIH2624]
>gi | 116196854 | ref | XP_001224239.1 | :1-102 conserved hypothetical protein [*Chaetomium globosum* CBS 148.51]
>gi | 119175741 | ref | XP_001240050.1 | :3-102 hypothetical protein CIMG_09671 [*Coccidioides immitis* RS]
>gi | 119471607 | ref | XP_001258195.1 | :12-111 chaperonin, putative [*Neosartorya fischeri* NRRL181]
>gi | 121699818 | ref | XP_001268174.1 | :8-106 chaperonin, putative [*Aspergillus clavatus* NRRL 1]
>gi | 126274604 | ref | XP_001387607.1 | :2-102 predicted protein [*Scheffersomyces stipitis* CBS 6054]
>gi | 146417701 | ref | XP_001484818.1 | :5-106 conserved hypothetical protein [*Meyerozyma guilliermondii* ATCC 6260]
>gi | 154303611 | ref | XP_001552212.1 | :1-102 10 kDa heat shock protein, mitochondrial [*Botryotinia fuckeliana* B05.10]
>gi | 156049571 | ref | XP_001590752.1 | :1-102 hypothetical protein SS1G_08492 [*Sclerotinia sclerotiorum* 1980]
>gi | 156840987 | ref | XP_001643870.1 | :1-103 hypothetical protein Kpol_495p10 [*Vanderwaltozyma polyspora* DSM 70924]
>gi | 169608295 | ref | XP_001797567.1 | :1-101 hypothetical protein SNOG_07218 [*Phaeosphaeria nodorum* SN15]
>gi | 171688384 | ref | XP_001909132.1 | :1-102 hypothetical protein [*Podospora anserina* S mat+]
>gi | 189189366 | ref | XP_001931022.1 | :71-168 10 kDa chaperonin [*Pyrenophora tritici-repentis* Pt-1C-BFP]
>gi | 19075598 | ref | NP_588098.1 | :1-102 mitochondrial heat shock protein Hsp10 (predicted) [*Schizosaccharomyces pombe* 972h-]
>gi | 212530240 | ref | XP_002145277.1 | :3-100 chaperonin, putative [*Talaromyces marneffei* ATCC 18224]
>gi | 212530242 | ref | XP_002145278.1 | :3-95 chaperonin, putative [*Talaromyces marneffei* ATCC 18224]
>gi | 213404320 | ref | XP_002172932.1 | :1-102 mitochondrial heat shock protein Hsp10 [*Schizosaccharomyces japonicus* yFS275]
>gi | 225557301 | gb | EEH05587.1 | :381-478 pre-mRNA polyadenylation factor fip1 [*Ajellomyces capsulatus* G186AR]

TABLE 3-continued

Natural chaperones homologous to SEQUENCE ID
NO: 10 polypeptides suitable for expression >gi | 225684092 | gb | EEH22376.1 | :3-100 heat shock protein [*Paracoccidioides brasiliensis* Pb03]
>gi | 238490530 | ref | XP_002376502.1 | :2-104 chaperonin, putative [*Aspergillus flavus* NRRL3357]
>gi | 238878220 | gb | EEQ41858.1 | :1-106 10 kDa heat shock protein, mitochondrial [*Candida albicans* WO-1]
>gi | 240280207 | gb | EER43711.1 | :426-523 pre-mRNA polyadenylation factor fip1 [*Ajellomyces capsulatus* H143]
>gi | 241950445 | ref | XP_002417945.1 | :1-103 10 kda chaperonin, putative; 10 kda heat shock protein mitochondrial (hsp10), putative [*Candida dubliniensis* CD36]
>gi | 242819222 | ref | XP_002487273.1 | :90-182 chaperonin, putative [*Talaromyces stipitatus* ATC
>gi | 254566327 | ref | XP_002490274.1 | :1-102 Putative protein of unknown function [*Komagataella pastoris* GS115]
>gi | 254577241 | ref | XP_002494607.1 | :1-103 ZYRO0A05434p [*Zygosaccharomyces rouxii*]
>gi | 255717999 | ref | XP_002555280.1 | :1-103 KLTH0G05588p [*Lachancea thermotolerans*]
>gi | 255956581 | ref | XP_002569043.1 | :2-101 Pc21g20560 [*Penicillium chrysogenum* Wisconsin 54-1255]
>gi | 258572664 | ref | XP_002545094.1 | :16-108 chaperonin GroS [*Uncinocarpus reesii* 1704]
>gi | 261190594 | ref | XP_002621706.1 | :3-100 chaperonin [*Ajellomyces dermatitidis* SLH14081]
>gi | 295664909 | ref | XP_002793006.1 | :3-100 10 kDa heat shock protein, mitochondrial [*Paracoccidioides* sp. 'lutzii'Pb01]
>gi | 296412657 | ref | XP_002836039.1 | :76-177 hypothetical protein [*Tuber melanosporum* Mel28]
>gi | 302307854 | ref | NP_984626.2 | :2-102 AEL235Wp [*Ashbya gossypii* ATCC 10895]
>gi | 302894117 | ref | XP_003045939.1 | :1-102 predicted protein [*Nectria haematococca* mpVI 77-13-4]
>gi | 303318351 | ref | XP_003069175.1 | :3-100 10 kDa heat shock protein, mitochondrial, putative [*Coccidioides posadasii* C735 delta SOWgp]
>gi | 310795300 | gb | EFQ30761.1 | :1-102 chaperonin 10 kDa subunit [*Glomerella graminicola* M1.001]
>gi | 315053085 | ref | XP_003175916.1 | :12-109 chaperonin GroS [*Arthroderma gypseum* CBS 118893]
>gi | 317032114 | ref | XP_001394060.2 | :334-433 heat shock protein [*Aspergillus niger* CBS 513.88]
>gi | 317032116 | ref | XP_001394059.2 | :2-101 heat shock protein [*Aspergillus niger* CBS 513.88]
>gi | 320583288 | gb | EFW97503.1 | :6-106 chaperonin, putative heat shock protein, putative [*Ogataea parapolymorpha* DL-1]
>gi | 320591507 | gb | EFX03946.1 | :1-102 heat shock protein [*Grosmannia clavigera* kw1407]
>gi | 322700925 | gb | EFY92677.1 | :1-102 chaperonin [*Metarhizium acridum* CQMa 102]
>gi | 325096696 | gb | EGC50006.1 | :409-506 pre-mRNA polyadenylation factor fip1 [*Ajellomyces capsulatus* H88]
>gi | 326471604 | gb | EGD95613.1 | :14-111 chaperonin 10 Kd subunit [*Trichophyton tonsurans* CBS112818]
>gi | 327293056 | ref | XP_003231225.1 | :3-100 chaperonin [*Trichophyton rubrum* CBS 118892]
>gi | 330942654 | ref | XP_003306155.1 | :37-136 hypothetical protein PTT_19211 [*Pyrenophora teres f. teres* 0-1]
>gi | 336268042 | ref | XP_003348786.1 | :47-147 hypothetical protein SMAC_01809 [*Sordaria macrospora* khell]
>gi | 340519582 | gb | EGR49820.1 | :1-109 predicted protein [*Trichoderma reesei* QM6a]
>gi | 340960105 | gb | EGS21286.1 | :3-103 putative mitochondrial 10 kDa heat shock protein [*Chaetomium thermophilum* var. *thermophilum* DSM 1495]
>gi | 342883802 | gb | EGU84224.1 | :1-102 hypothetical protein FOXB_05181 [*Fusarium oxysporum* Fo5176]
>gi | 344302342 | gb | EGW32647.1 | :2-102 hypothetical protein SPAPADRAFT_61712 [*Spathaspora passalidarum* NRRL Y-27907]
>gi | 345570750 | gb | EGX53571.1 | :1-102 hypothetical protein AOL_s00006g437 [*Arthrobotrys oligospora* ATCC 24927]
>gi | 346321154 | gb | EGX90754.1 | :1-102 chaperonin [*Cordyceps militaris* CM01]
>gi | 346970393 | gb | EGY13845.1 | :1-102 heat shock protein [*Verticillium dahliae* VdLs.17]
>gi | 354548296 | emb | CCE45032.1 | :1-106 hypothetical protein CPAR2_700360 [*Candida parapsilosis*]
>gi | 358385052 | gb | EHK22649.1 | :1-102 hypothetical protein TRIVIDRAFT_230640 [*Trichoderma virens* Gv 29-8]

TABLE 3-continued

Natural chaperones homologous to SEQUENCE ID
NO: 10 polypeptides suitable for expression >gi | 358393422 | gb | EHK42823.1 | :1-101 hypothetical protein TRIATDRAFT_258186 [*Trichoderma atroviride* IMI 206040]
>gi | 361126733 | gb | EHK98722.1 | :1-97 putative 10 kDa heat shock protein, mitochondrial [*Glare lozoyensis* 74030]
>gi | 363753862 | ref | XP_003647147.1 | :2-102 hypothetical protein Ecym_5593 [*Eremothecium cymbalariae* DBVPG#7215]
>gi | 365758401 | gb | EHN00244.1 | :1-106 Hsp10p [*Saccharomyces cerevisiae* × *Saccharomyces kudriavzevii* VIN7]
>gi | 365987664 | ref | XP_003670663.1 | :1-103 hypothetical protein NDAI_0F01010 [*Naumovozyma dairenensis* CBS 421]
>gi | 366995125 | ref | XP_003677326.1 | :1-103 hypothetical protein NCAS_0G00860 [*Naumovozyma castellii* CBS 4309]
>gi | 366999797 | ref | XP_003684634.1 | :1-103 hypothetical protein TPHA_0C00430 [*Tetrapisispora phaffii* CBS 4417]
>gi | 367009030 | ref | XP_003679016.1 | :1-103 hypothetical protein TDEL_0A04730 [*Torulaspora delbruekii*]
>gi | 367023138 | ref | XP_003660854.1 | :1-104 hypothetical protein MYCTH_59302 [*Myceliophthora thermophila* ATCC 42464]
>gi | 367046344 | ref | XP_003653552.1 | :1-102 hypothetical protein THITE_2116070 [*Thielavia terrestris* NRRL8126]
>gi | 378726440 | gb | EHY52899.1 | :9-109 chaperonin GroES [*Exophiala dermatitidis* NIH/UT8656]
>gi | 380493977 | emb | CCF33483.1 | :1-102 chaperonin 10 kDa subunit [*Colletotrichum higginsianu*
>gi | 385305728 | gb | EIF49680.1 | :1-102 10 kda heat shock mitochondrial [*Dekkera bruxellensis* AWRI1499]
>gi | 389628546 | ref | XP_003711926.1 | :1-102 hsp10-like protein [*Magnaporthe oryzae* 70-15]
>gi | 396462608 | ref | XP_003835915.1 | :1-101 similar to 10 kDa heat shock protein [*Leptosphaeria maculans* JN3]
>gi | 398392541 | ref | XP_003849730.1 | :1-102 hypothetical protein MYCGRDRAFT_105721 [*Zymoseptoria tritici* IPO323]
>gi | 400597723 | gb | EJP65453.1 | :24-124 chaperonin 10 kDa subunit [*Beauveria bassiana* ARSEF 2860]
>gi | 401623646 | gb | EJS41738.1 | :1-106 hsp10p [*Saccharomyces arboricola* H-6]
>gi | 401842164 | gb | EJT44422.1 | :1-92 HSP10-like protein [*Saccharomyces kudriavzevii* IFO 1802]
>gi | 402084027 | gb | EJT79045.1 | :1-102 hsp10-like protein [*Gaeumannomyces graminis* var. triti
>gi | 403215209 | emb | CCK69709.1 | :1-104 hypothetical protein KNAG_0C06130 [*Kazachstania naganishii* CBS 8797]
>gi | 406604629 | emb | CCH43969.1 | :4-100 hypothetical protein BN7_3524 [*Wickerhamomyces ciferrii*]
>gi | 406867021 | gb | EKD20060.1 | :56-156 hypothetical protein MBM_02012 [*Marssonina brunnea* f. sp. 'multigermtubi' MB_m1]
>gi | 407926227 | gb | EKG19196.1 | :74-174 GroES-like protein [*Macrophomina phaseolina* MS6]
>gi | 408398157 | gb | EKJ77291.1 | :11-111 hypothetical protein FPSE_02566 [*Fusarium pseudograminearum* CS3096]
>gi | 410082063 | ref | XP_003958610.1 | :1-103 hypothetical protein KAFR_0H00660 [*Kazachstania africana* CBS2517]
>gi | 425777664 | gb | EKV15823.1 | :58-157 Chaperonin, putative [*Penicillium digitatum* Pd1]
>gi | 440639680 | gb | ELR09599.1 | :1-102 chaperonin GroES [*Geomyces destructans* 20631-21]
>gi | 444323906 | ref | XP_004182593.1 | :1-105 hypothetical protein TBLA_0J00760 [*Tetrapisisporablattae* CBS 6284]
>gi | 448083208 | ref | XP_004195335.1 | :2-101 Piso0_005888 [*Millerozyma farinosa* CBS 7064]
>gi | 448087837 | ref | XP_004196425.1 | :2-102 Piso0_005888 [*Millerozyma farinosa* CBS 7064]
>gi | 448534948 | ref | XP_003870866.1 | :1-106 Hsp10 protein [*Candida orthopsilosis* Co 90-125]
>gi | 449295977 | gb | EMC91998.1 | :1-102 hypothetical protein BAUCODRAFT_39148 [*Baudoinia compn*
>gi | 46123659 | ref | XP_386383.1 | :3-103 hypothetical protein FG06207.1 [*Gibberella zeae* PH-1]
>gi | 50289455 | ref | XP_447159.1 | :1-103 hypothetical protein [*Candida glabrata* CBS 138]
>gi | 50308731 | ref | XP_454370.1 | :1-103 hypothetical protein [*Kluyveromyces lactis* NRRL Y-1140]
>gi | 50411066 | ref | XP_457014.1 | :1-106 DEHA2B01122p [*Debaryomyces hansenii* CBS767]
>gi | 50545998 | ref | XP_500536.1 | :1-102 YALI0B05610p [*Yarrowia lipolytica*]
>gi | 51013895 | gb | AAT93241.1 | :1-106 YOR020C [*Saccharomyces cerevisiae*]
>gi | 6324594 | ref | NP_014663.1 | :1-106 Hsp10p [*Saccharomyces cerevisiae* S288c]

TABLE 3-continued

Natural chaperones homologous to SEQUENCE ID
NO: 10 polypeptides suitable for expression >gi | 67523953 | ref | XP_660036.1 | :2-101 hypothetical protein AN2432.2
[*Aspergillus nidulans* FGSC A4]
>gi | 70992219 | ref | XP_750958.1 | :12-106 chaperonin [*Aspergillus fumigatus* Af293]
>gi | 85079266 | ref | XP_956315.1 | :1-104 hypothetical protein NCU04334
[*Neurospora crassa* OR74A]

As a preferred alternative to GroES a functional homologue of GroES may be present, in particular a functional homologue comprising a sequence having at least 70%, 75%, 80%, 85%, 90% or 95% sequence identity with SEQUENCE ID NO: 12.

Suitable natural chaperones polypeptides homologous to SEQUENCE ID NO: 12 are given in Table 4.

TABLE 4

Natural chaperones homologous to SEQUENCE ID
NO: 12 polypeptides suitable for expression >gi | 115443330 | ref | XP_001218472.1 | heat shock protein 60, mitochondrial precursor [*Aspergillus terreus* NIH2624]
>gi | 114188341 | gb | EAU30041.1 | heat shock protein 60, mitochondrial precursor [*Aspergillus terreus* NIH2624]
>gi | 119480793 | ref | XP_001260425.1 | antigenic mitochondrial protein HSP60, putative [*Neosartorya fischeri* NRRL 181] >gi | 119408579 | gb | EAW18528.1 | antigenic mitochondrial protein HSP60, putative [*Neosartorya fischeri* NRRL 181]
>gi | 126138730 | ref | XP_001385888.1 | hypothetical protein PICST_90190 [*Scheffersomyces stipitis* CBS 6054] >gi | 126093166 | gb | ABN67859.1 | mitochondrial groEL-type heat shock protein [*Scheffersomyces stipitis* CBS 6054]
>gi | 145246630 | ref | XP_001395564.1 | heat shock protein 60 [*Aspergillus niger* CBS 513.88] >gi | 134080285 | emb | CAK46207.1 | unnamed protein product [*Aspergillus niger*] >gi | 350636909 | gb | EHA25267.1 | hypothetical protein ASPNIDRAFT_54001 [*Aspergillus niger* ATCC 1015]
>gi | 146413148 | ref | XP_001482545.1 | heat shock protein 60, mitochondrial precursor [*Meyerozyma guilliermondii* ATCC 6260]
>gi | 154277022 | ref | XP_001539356.1 | heat shock protein 60, mitochondrial precursor [*Ajellomyces capsulatus* NAm1] >gi | 150414429 | gb | EDN09794.1 | heat shock protein 60, mitochondrial precursor [*Ajellomyces capsulatus* NAm1]
>gi | 154303540 | ref | XP_001552177.1 | heat shock protein 60 [*Botryotinia fuckeliana* B05.10] >gi | 347840915 | emb | CCD55487.1 | similar to heat shock protein 60 [*Botryotinia fuckeliana*]
>gi | 156063938 | ref | XP_001597891.1 | heat shock protein 60, mitochondrial precursor [*Sclerotinia sclerotiorum* 1980] >gi | 154697421 | gb | EDN97159.1 | heat shock protein 60, mitochondrial precursor [*Sclerotinia sclerotiorum* 1980 UF-70]
>gi | 156844469 | ref | XP_001645297.1 | hypothetical protein Kpol_1037p35 [*Vanderwaltozyma polyspora* DSM 70294] >gi | 156115957 | gb | EDO17439.1 | hypothetical protein Kpol_1037p35 [*Vanderwaltozyma polyspora* DSM 70294]
>gi | 16416029 | emb | CAB91379.2 | probable heat-shock protein hsp60 [*Neurospora crassa*] >gi | 350289516 | gb | EGZ70741.1 | putative heat-shock protein hsp60 [*Neurospora tetrasperma* FGSC 2509]
>gi | 169626377 | ref | XP_001806589.1 | hypothetical protein SNOG_16475 [*Phaeosphaeria nodorum* SN15] >gi | 111055053 | gb | EAT76173.1 | hypothetical protein SNOG_16475 [*Phaeosphaeria nodorum* SN15]
>gi | 169783766 | ref | XP_001826345.1 | heat shock protein 60 [*Aspergillus oryzae* RIB40] >gi | 238493601 | ref | XP_002378037.1 | antigenic mitochondrial protein HSP60, putative [*Aspergillus flavus* NRRL3357] >gi | 83775089 | dbj | BAE65212.1 | unnamed protein product [*Aspergillus oryzae* RIB40]
>gi | 220696531 | gb | EED52873.1 | antigenic mitochondrial protein HSP60, putative [*Aspergillus flavus* NRRL3357] >gi | 391869413 | gb | EIT78611.1 | chaperonin, Cpn60/Hsp60p [*Aspergillus oryzae* 3.042]
>gi | 189190432 | ref | XP_001931555.1 | heat shock protein 60, mitochondrial precursor [*Pyrenophora tritici-repentis* Pt-1C-BFP]
>gi | 187973161 | gb | EDU40660.1 | heat shock protein 60, mitochondrial precursor [*Pyrenophora tritici-repentis* Pt-1C-BFP]
>gi | 190348913 | gb | EDK41467.2 | heat shock protein 60, mitochondrial precursor [*Meyerozyma guilliermondii* ATCC 6260]
>gi | 225554633 | gb | EEH02929.1 | hsp60-like protein [*Ajellomyces capsulatus* G186AR]
>gi | 238880068 | gb | EEQ43706.1 | heat shock protein 60, mitochondrial precursor [*Candida albicans* WO-1]
>gi | 239613490 | gb | EEQ90477.1 | chaperonin GroL [*Ajellomyces dermatitidis* ER-3]
>gi | 240276977 | gb | EER40487.1 | hsp60-like protein [*Ajellomyces capsulatus* H143]

TABLE 4-continued

Natural chaperones homologous to SEQUENCE ID
NO: 12 polypeptides suitable for expression >gi | 241958890 | ref | XP_002422164.1 | heat shock protein 60, mitochondrial precursor, putative [*Candida dubliniensis* CD36] >gi | 223645509 | emb | CAX40168.1 | heat shock protein 60, mitochondrial precursor, putative [*Candida dubliniensis* CD36]
>gi | 254572906 | ref | XP_002493562.1 | Tetradecameric mitochondrial chaperonin [*Komagataella pastoris* GS115] >gi | 238033361 | emb | CAY71383.1 | Tetradecameric mitochondrial chaperonin [*Komagataella pastoris* GS115]
>gi | 254579947 | ref | XP_002495959.1 | ZYRO0C07106p [*Zygosaccharomyces rouxii*]
>gi | 238938850 | emb | CAR27026.1 | ZYRO0C07106p [*Zygosaccharomyces rouxii*]
>gi | 255712781 | ref | XP_002552673.1 | KLTH0C10428p [*Lachancea thermotolerans*]
>gi | 238934052 | emb | CAR22235.1 | KLTH0C10428p [*Lachancea thermotolerans* CBS 6340]
>gi | 255721795 | ref | XP_002545832.1 | heat shock protein 60, mitochondrial precursor [*Candida tropicalis* MYA-3404] >gi | 240136321 | gb | EER35874.1 | heat shock protein 60, mitochondrial precursor [*Candida tropicalis* MYA-3404]
>gi | 255941288 | ref | XP_002561413.1 | Pc16g11070 [*Penicillium chrysogenum* Wisconsin 54-1255] >gi | 211586036 | emb | CAP93777.1 | Pc16g11070 [*Penicillium chrysogenum* Wisconsin 54-1255]
>gi | 259148241 | emb | CAY81488.1 | Hsp60p [*Saccharomyces cerevisiae* EC1118]
>gi | 260950325 | ref | XP_002619459.1 | heat shock protein 60, mitochondrial precursor [*Clavispora lusitaniae* ATCC 42720] >gi | 238847031 | gb | EEQ36495.1 | heat shock protein 60, mitochondrial precursor [*Clavispora lusitaniae* ATCC 42720]
>gi | 261194577 | ref | XP_002623693.1 | chaperonin GroL [*Ajellomyces dermatitidis* SLH14081] >gi | 239588231 | gb | EEQ70874.1 | chaperonin GroL [*Ajellomyces dermatitidis* SLH14081] >gi | 327355067 | gb | EGE83924.1 | chaperonin GroL [*Ajellomyces dermatitidis* ATCC 18188]
>gi | 296422271 | ref | XP_002840685.1 | hypothetical protein [*Tuber melanosporum* Mel28] >gi | 295636906 | emb | CAZ84876.1 | unnamed protein product [*Tuber melanosporum*]
>gi | 296809035 | ref | XP_002844856.1 | heat shock protein 60 [*Arthroderma otae* CBS 113480] >gi | 238844339 | gb | EEQ34001.1 | heat shock protein 60 [*Arthroderma otae* CBS 113480]
>gi | 302308696 | ref | NP_985702.2 | AFR155Wp [*Ashbya gossypii* ATCC 10895]
>gi | 299790751 | gb | AAS53526.2 | AFR155Wp [*Ashbya gossypii* ATCC 10895]
>gi | 374108933 | gb | AEY97839.1 | FAFR155Wp [*Ashbya gossypii* FDAG1]
>gi | 302412525 | ref | XP_003004095.1 | heat shock protein [*Verticillium albo-atrum* VaMs.102] >gi | 261356671 | gb | EEY19099.1 | heat shock protein [*Verticillium albo-atrum* VaMs. 102]
>gi | 302505585 | ref | XP_003014499.1 | hypothetical protein ARB_07061 [*Arthroderma benhamiae* CBS 112371] >gi | 291178320 | gb | EFE34110.1 | hypothetical protein ARB_07061 [*Arthroderma benhamiae* CBS 112371]
>gi | 302656385 | ref | XP_003019946.1 | hypothetical protein TRV_05992 [*Trichophyton verrucosum* HKI 0517] >gi | 291183723 | gb | EFE39322.1 | hypothetical protein TRV_05992 [*Trichophyton verrucosum* HKI 0517]
>gi | 302915513 | ref | XP_003051567.1 | predicted protein [*Nectria haematococca* mpVI 77-13-4] >gi | 256732506 | gb | EEU45854.1 | predicted protein [*Nectria haematococca* mpVI 77-13-4]
>gi | 310794550 | gb | EFQ30011.1 | chaperonin GroL [*Glomerella graminicola* M1.001]
>gi | 315048491 | ref | XP_003173620.1 | chaperonin GroL [*Arthroderma gypseum* CBS 118893] >gi | 311341587 | gb | EFR00790.1 | chaperonin GroL [*Arthroderma gypseum* CBS 118893]
>gi | 320580028 | gb | EFW94251.1 | Tetradecameric mitochondrial chaperonin [*Ogataea parapolymorpha* DL-1]
>gi | 320586014 | gb | EFW98693.1 | heat shock protein mitochondrial precursor [*Grosmannia clavigera* kw1407]
>gi | 322692465 | gb | EFY84374.1 | Heat shock protein 60 precursor (Antigen HIS-62) [*Metarhizium acridum* CQMa 102]
>gi | 322705285 | gb | EFY96872.1 | Heat shock protein 60 (Antigen HIS-62) [*Metarhizium anisopliae* ARSEF 23]
>gi | 323303806 | gb | EGA57589.1 | Hsp60p [*Saccharomyces cerevisiae* FostersB]
>gi | 323307999 | gb | EGA61254.1 | Hsp60p [*Saccharomyces cerevisiae* FostersO]
>gi | 323332364 | gb | EGA73773.1 | Hsp60p [*Saccharomyces cerevisiae* AWRI796]
>gi | 326468648 | gb | EGD92657.1 | heat shock protein 60 [*Trichophyton tonsurans* CBS 112818] >gi | 326479866 | gb | EGE03876.1 | chaperonin GroL [*Trichophyton equinum* CBS 127.97]
>gi | 330915493 | ref | XP_003297052.1 | hypothetical protein PTT_07333 [*Pyrenophora teres f. teres* 0-1] >gi | 311330479 | gb | EFQ94847.1 | hypothetical protein PTT_07333 [*Pyrenophora teres f. teres* 0-1]
>gi | 336271815 | ref | XP_003350665.1 | hypothetical protein SMAC_02337 [*Sordaria macrospora k-hell*] >gi | 380094827 | emb | CCC07329.1 | unnamed protein product [*Sordaria macrospora k-hell*]
>gi | 336468236 | gb | EGO56399.1 | hypothetical protein NEUTE1DRAFT_122948 [*Neurospora tetrasperma* FGSC 2508]
>gi | 340522598 | gb | EGR52831.1 | hsp60 mitochondrial precursor-like protein [*Trichoderma reesei* QM6a]
>gi | 341038907 | gb | EGS23899.1 | mitochondrial heat shock protein 60-like protein [*Chaetomium thermophilum* var. *thermophilum* DSM 1495]

TABLE 4-continued

Natural chaperones homologous to SEQUENCE ID
NO: 12 polypeptides suitable for expression \>gi | 342886297 | gb | EGU86166.1 | hypothetical protein FOXB_03302 [*Fusarium oxysporum* Fo5176]
\>gi | 344230084 | gb | EGV61969.1 | chaperonin GroL [*Candida tenuis* ATCC 10573]
\>gi | 344303739 | gb | EGW33988.1 | hypothetical protein SPAPADRAFT_59397 [*Spathaspora passalidarum* NRRL Y-27907]
\>gi | 345560428 | gb | EGX43553.1 | hypothetical protein AOL_s00215g289 [*Arthrobotrys oligospora* ATCC 24927]
\>gi | 346323592 | gb | EGX93190.1 | heat shock protein 60 (Antigen HIS-62) [*Cordyceps militaris* CM01]
\>gi | 346975286 | gb | EGY18738.1 | heat shock protein [*Verticillium dahliae* VdLs.17]
\>gi | 354545932 | emb | CCE42661.1 | hypothetical protein CPAR2_203040 [*Candida parapsilosis*]
\>gi | 358369894 | dbj | GAA86507.1 | heat shock protein 60, mitochondrial precursor [*Aspergillus kawachii* IFO 4308]
\>gi | 358386867 | gb | EHK24462.1 | hypothetical protein TRIVIDRAFT_79041 [*Trichoderma virens* Gv29-8]
\>gi | 358399658 | gb | EHK48995.1 | hypothetical protein TRIATDRAFT_297734 [*Trichoderma atroviride* IMI 206040]
\>gi | 363750488 | ref | XP_003645461.1 | hypothetical protein Ecym_3140 [*Eremothecium cymbalariae* DBVPG#7215]
\>gi | 356889095 | gb | AET38644.1 | Hypothetical protein Ecym_3140 [*Eremothecium cymbalariae* DBVPG#7215]
\>gi | 365759369 | gb | EHN01160.1 | Hsp60p [*Saccharomyces cerevisiae* × *Saccharomyces kudriavzevii* VIN7]
\>gi | 365764091 | gb | EHN05616.1 | Hsp60p [*Saccharomyces cerevisiae* × *Saccharomyces kudriavzevii* VIN7]
\>gi | 365985626 | ref | XP_003669645.1 | hypothetical protein NDAI_0D00880 [*Naumovozyma dairenensis* CBS 421]
\>gi | 343768414 | emb | CCD24402.1 | hypothetical protein NDAI_0D00880 [*Naumovozyma dairenensis* CBS 421]
\>gi | 366995970 | ref | XP_003677748.1 | hypothetical protein NCAS_0H00890 [*Naumovozyma castellii* CBS 4309]
\>gi | 342303618 | emb | CCC71399.1 | hypothetical protein NCAS_0H00890 [*Naumovozyma castellii* CBS 4309]
\>gi | 367005154 | ref | XP_003687309.1 | hypothetical protein TPHA_0J00520 [*Tetrapisispora phaffii* CBS 4417] \>gi | 357525613 | emb | CCE64875.1 | hypothetical protein TPHA_0J00520 [*Tetrapisispora phaffii* CBS 4417]
\>gi | 367017005 | ref | XP_003683001.1 | hypothetical protein TDEL_0G04230 [*Torulaspora delbrueckii*] \>gi | 359750664 | emb | CCE93790.1 | hypothetical protein TDEL_0G04230 [*Torulaspora delbrueckii*]
\>gi | 367035486 | ref | XP_003667025.1 | hypothetical protein MYCTH_2097570 [*Myceliophthora thermophila* ATCC 42464]
\>gi | 347014298 | gb | AEO61780.1 | hypothetical protein MYCTH_2097570 [*Myceliophthora thermophila* ATCC 42464]
\>gi | 367055018 | ref | XP_003657887.1 | hypothetical protein THITE_127923 [*Thielavia terrestris* NRRL 8126] \>gi | 347005153 | gb | AEO71551.1 | hypothetical protein THITE_127923 [*Thielavia terrestris* NRRL 8126]
\>gi | 378728414 | gb | EHY54873.1 | heat shock protein 60 [*Exophiala dermatitidis* NIH/UT8656]
\>gi | 380494593 | emb | CCF33032.1 | heat shock protein 60 [*Colletotrichum higginsianum*]
\>gi | 385305893 | gb | EIF49836.1 | heat shock protein 60 [*Dekkera bruxellensis* AWRI1499]
\>gi | 389638386 | ref | XP_003716826.1 | heat shock protein 60 [*Magnaporthe oryzae* 70-15] \>gi | 351642645 | gb | EHA50507.1 | heat shock protein 60 [*Magnaporthe oryzae* 70-15] \>gi | 440474658 | gb | ELQ43388.1 | heat shock protein 60 [*Magnaporthe oryzae* Y34] \>gi | 440480475 | gb | ELQ61135.1 | heat shock protein 60 [*Magnaporthe oryzae* P131]
\>gi | 393243142 | gb | EJD50658.1 | chaperonin GroL [*Auricularia delicata* TFB-10046 SS5]
\>gi | 396494741 | ref | XP_003844378.1 | similar to heat shock protein 60 [*Leptosphaeria maculans* JN3] \>gi | 312220958 | emb | CBY00899.1 | similar to heat shock protein 60 [*Leptosphaeria maculans* JN3]
\>gi | 398393428 | ref | XP_003850173.1 | chaperone ATPase HSP60 [*Zymoseptoria tritici* IPO323] \>gi | 339470051 | gb | EGP85149.1 | hypothetical protein MYCGRDRAFT_75170 [*Zymoseptoria tritici* IPO323]
\>gi | 401624479 | gb | EJS42535.1 | hsp60p [*Saccharomyces arboricola* H-6]
\>gi | 401842294 | gb | EJT44530.1 | HSP60-like protein [*Saccharomyces kudriavzevii* IFO 1802]
\>gi | 402076594 | gb | EJT72017.1 | heat shock protein 60 [*Gaeumannomyces graminis* var. *tritici* R3-111a-1]
\>gi | 403213867 | emb | CCK68369.1 | hypothetical protein KNAG_0A07160 [*Kazachstania naganishii* CBS 8797]
\>gi | 406606041 | emb | CCH42514.1 | Heat shock protein 60, mitochondrial [*Wickerhamomyces ciferrii*]
\>gi | 406863285 | gb | EKD16333.1 | heat shock protein 60 [*Marssonina brunnea* f. sp. 'multigermtubi' MB_m1]

TABLE 4-continued

Natural chaperones homologous to SEQUENCE ID
NO: 12 polypeptides suitable for expression >gi | 407922985 | gb | EKG16075.1 | Chaperonin Cpn60 [*Macrophomina phaseolina* MS6]
>gi | 408399723 | gb | EKJ78816.1 | hypothetical protein FPSE_00959 [*Fusarium pseudograminearum* CS3096]
>gi | 410083028 | ref | XP_003959092.1 | hypothetical protein KAFR_0I01760 [*Kazachstania africana* CBS 2517] >gi | 372465682 | emb | CCF59957.1 | hypothetical protein KAFR_0I01760 [*Kazachstania africana* CBS 2517]
>gi | 444315528 | ref | XP_004178421.1 | hypothetical protein TBLA_0B00580 [*Tetrapisispora blattae* CBS 6284] >gi | 387511461 | emb | CCH58902.1 | hypothetical protein TBLA_0B00580 [*Tetrapisispora blattae* CBS 6284]
>gi | 448090588 | ref | XP_004197110.1 | Piso0_004347 [*Millerozyma farinosa* CBS 7064] >gi | 448095015 | ref | XP_004198141.1 | Piso0_004347 [*Millerozyma farinosa* CBS 7064] >gi | 359378532 | emb | CCE84791.1 | Piso0_004347 [*Millerozyma farinosa* CBS 7064] >gi | 359379563 | emb | CCE83760.1 | Piso0_004347 [*Millerozyma farinosa* CBS 7064]
>gi | 448526196 | ref | XP_003869293.1 | Hsp60 heat shock protein [*Candida orthopsilosis* Co 90-125] >gi | 380353646 | emb | CCG23157.1 | Hsp60 heat shock protein [*Candida orthopsilosis*]
>gi | 46123737 | ref | XP_386422.1 | HS60_AJECA Heat shock protein 60, mitochondrial precursor (Antigen HIS-62) [*Gibberella zeae* PH-1]
>gi | 50292099 | ref | XP_448482.1 | hypothetical protein [*Candida glabrata* CBS 138]
>gi | 49527794 | emb | CAG61443.1 | unnamed protein product [*Candida glabrata*]
>gi | 50310975 | ref | XP_455510.1 | hypothetical protein [*Kluyveromyces lactis* NRRL Y-1140] >gi | 49644646 | emb | CAG98218.1 | KLLA0F09449p [*Kluyveromyces lactis*]
>gi | 50422027 | ref | XP_459575.1 | DEHA2E05808p [*Debaryomyces hansenii* CBS767] >gi | 49655243 | emb | CAG87802.1 | DEHA2E05808p [*Debaryomyces hansenii* CBS767]
>gi | 50555023 | ref | XP_504920.1 | YALI0F02805p [*Yarrowia lipolytica*]
>gi | 49650790 | emb | CAG77725.1 | YALI0F02805p [*Yarrowia lipolytica* CLIB122]
>gi | 6323288 | ref | NP_013360.1 | Hsp60p [*Saccharomyces cerevisiae* S288c]
>gi | 123579 | sp | P19882.1 | HSP60_YEAST RecName: Full = Heat shock protein 60, mitochondrial; AltName: Full = CPN60; AltName: Full = P66; AltName: Full = Stimulator factor I 66 kDa component; Flags:Precursor
>gi | 171720 | gb | AAA34690.1 | heat shock protein 60 (HSP60) [*Saccharomyces cerevisiae*] >gi | 577181 | gb | AAB67380.1 | Hsp60p: Heat shock protein 60 [*Saccharomyces cerevisiae*] >gi | 151941093 | gb | EDN59473.1 | chaperonin [*Saccharomyces cerevisiae* YJM789] >gi | 190405319 | gb | EDV08586.1 | chaperonin [*Saccharomyces cerevisiae* RM11-1a] >gi | 207342889 | gb | EDZ70518.1 | YLR259Cp-like protein [*Saccharomyces cerevisiae* AWRI1631]
>gi | 256271752 | gb | EEU06789.1 | Hsp60p [*Saccharomyces cerevisiae* JAY291]
>gi | 285813676 | tpg | DAA09572.1 | TPA: chaperone ATPase HSP60 [*Saccharomyces cerevisiae* S288c] >gi | 323353818 | gb | EGA85673.1 | Hsp60p [*Saccharomyces cerevisiae* VL3] >gi | 349579966 | dbj | GAA25127.1 | K7_Hsp60p [*Saccharomyces cerevisiae* Kyokai no. 7] >gi | 392297765 | gb | EIW08864.1 | Hsp60p [*Saccharomyces cerevisiae* CEN.PK113-7D] >gi | 226279 | prf | | 1504305A mitochondrial assembly factor
>gi | 68485963 | ref | XP_713100.1 | heat shock protein 60 [*Candida albicans* SC5314]
>gi | 68486010 | ref | XP_713077.1 | heat shock protein 60 [*Candida albicans* SC5314]
>gi | 6016258 | sp | O74261.1 | HSP60_CANAL RecName: Full = Heat shock protein 60, mitochondrial; AltName: Full = 60 kDa chaperonin; AltName: Full = Protein Cpn60; Flags: Precursor >gi | 3552009 | gb | AAC34885.1 | heat shock protein 60 [*Candida albicans*] >gi | 46434552 | gb | EAK93958.1 | heat shock protein 60 [*Candida albicans* SC5314] >gi | 46434577 | gb | EAK93982.1 | heat shock protein 60 [*Candida albicans* SC5314]
>gi | 71001164 | ref | XP_755263.1 | antigenic mitochondrial protein HSP60 [*Aspergillus fumigatus* Af293] >gi | 66852901 | gb | EAL93225.1 | antigenic mitochondrial protein HSP60, putative [*Aspergillus fumigatus* Af293]
>gi | 159129345 | gb | EDP54459.1 | antigenic mitochondrial protein HSP60, putative [*Aspergillus fumigatus* A1163]
>gi | 90970323 | gb | ABE02805.1 | heat shock protein 60 [*Rhizophagus intraradices*]

In an embodiment, a 10 kDa chaperone from Table 3 is combined with a matching 60 kDa chaperone from table 4 of the same organism genus or species for expression in the host.

For instance: >gi|189189366|ref|XP_001931022.1|:71-168 10 kDa chaperonin [Pyrenophora tritici-repentis] expressed together with matching >gi|189190432|ref|XP_001931555.1| heat shock protein 60, mitochondrial precursor [Pyrenophora tritici-repentis Pt-1C-BFP].

All other combinations from Table 3 and 4 similarly made with same organism source are also available to the skilled person for expression.

Further, one may combine a chaperone from Table 3 from one organism with a chaperone from Table 4 from another organism, or one may combine GroES with a chaperone from Table 3, or one may combine GroEL with a chaperone from Table 4.

As follows from the above, the invention further relates to a method for preparing an organic compound comprising converting a carbon source, using a microorganism, thereby forming the organic compound. The method may be carried out under aerobic, oxygen-limited or anaerobic conditions.

The invention allows in particular a reduction in formation of an NADH dependent side-product, especially glycerol, by up to 100%, up to 99%, or up to 90%, compared to said production in a corresponding reference strain. The NADH dependent side-product formation is preferably reduced by more than 10% compared to the corresponding reference strain, in particular by at least 20%, more in particular by at least 50%. NADH dependent side-product production is preferably reduced by 10-100%, in particular by 20-95%, more in particular by 50-90%.

In preferred method wherein Rubisco, or another enzyme capable of catalysing the formation of an organic compound from $CO_2$ (and another substrate) or another enzyme that catalyses the function of $CO_2$ as an electron acceptor, is used, the carbon dioxide concentration in the reaction medium is at least 5% of the $CO_2$ saturation concentration under the reaction conditions, in particular at least 10% of said $CO_2$ saturation concentration, more in particular at least 20% of said $CO_2$ saturation concentration. This is in particular advantageous with respect to product yield. The reaction medium may be oversaturated in $CO_2$ concentration, saturated in $CO_2$ concentration or may have a concentration below saturation concentration. In a specific embodiment, the $CO_2$ concentration is 75% of the saturation concentration or less, in particular 50% of said saturation concentration or less, more in particular is 25% of the $CO_2$ saturation concentration or less.

In a specific embodiment, the carbon dioxide or part thereof is formed in situ by the microorganism. If desired, the method further comprises the step of adding external $CO_2$ to the reaction system, usually by aeration with $CO_2$ or a gas mixture containing $CO_2$, for instance a $CO_2$/nitrogen mixture. Adding external $CO_2$ in particular is used to (increase or) maintain the $CO_2$ within a desired concentration range, if no or insufficient $CO_2$ is formed in situ.

Determination of the $CO_2$ concentration in a fluid is within the routine skills of the person skilled in the art. In practice, one may routinely determine the $CO_2$ concentration in the gas phase above a culture of the yeast (practically the off-gas if the medium is purged with a gas). This can routinely be measured using a commercial gas analyser, such as a RosemountNGA200000 gas analyser (Rosemount Analytical, Orrvile, USA). The concentration in the liquid phase (relative to the saturation concentration), can then be calculated from the measured value in the gas, from the $CO_2$ saturation concentration and Henri coefficients of under the existing conditions in the method. These parameters are available from handbooks or can be routinely determined.

As a carbon source, in principle any carbon source that the microorganism can use as a substrate can be used. In particular an organic carbon source may be used, selected from the group of carbohydrates and lipids (including fatty acids). Suitable carbohydrates include monosaccharides, disaccharides, and hydrolysed polysaccharides (e.g. hydrolysed starches, lignocellulosic hydrolysates). Although a carboxylic acid may be present, it is not necessary to include a carboxylic acid such as acetic acid, as a carbon source.

It is in particular an advantage of the present invention that an improved ethanol yield and a reduced glycerol production is feasible compared to, e.g., a wild type yeast cell, without needing to intervene in the genome of the cell by inhibition of a glycerol 3-phosphate phosphohydrolase and/or encoding a glycerol 3-phosphate dehydrogenase gene.

Still, in a specific embodiment, a yeast cell according to the invention may comprise a deletion or disruption of one or more endogenous nucleotide sequence encoding a glycerol 3-phosphate phosphohydrolase and/or encoding a glycerol 3-phosphate dehydrogenase gene:

Herein in the cell, enzymatic activity needed for the NADH-dependent glycerol synthesis is reduced or deleted. The reduction or deleted of this enzymatic activity can be achieved by modifying one or more genes encoding a NAD-dependent glycerol 3-phosphate dehydrogenase activity (GPD) or one or more genes encoding a glycerol phosphate phosphatase activity (GPP), such that the enzyme is expressed considerably less than in the wild-type or such that the gene encoded a polypeptide with reduced activity.

Such modifications can be carried out using commonly known biotechnological techniques, and may in particular include one or more knock-out mutations or site-directed mutagenesis of promoter regions or coding regions of the structural genes encoding GPD and/or GPP. Alternatively, yeast strains that are defective in glycerol production may be obtained by random mutagenesis followed by selection of strains with reduced or absent activity of GPD and/or GPP. S. cerevisiae GPD1, GPD2, GPP1 and GPP2 genes are shown in WO 2011/010923, and are disclosed in SEQ ID NO: 24-27 of that application. The contents of this application are incorporated by reference, in particular the contents relating to GPD and/or GPP.

As shown in the Examples below, the invention is in particular found to be advantageous in a process for the production of an alcohol, notably ethanol. However, it is contemplated that the insight that $CO_2$ can be used as an electron acceptor in microorganisms that do not naturally allow this, has an industrial benefit for other biotechnological processes for the production of organic molecules, in particular organic molecules of a relatively low molecular weight, particularly organic molecules with a molecular weight below 1000 g/mol. The following items are mentioned herein as preferred embodiments of the use of carbon dioxide as an electron acceptor in accordance with the invention.

1. Use of carbon dioxide as an electron acceptor in a recombinant chemotrophic micro-organism is a non-phototrophic eukaryotic micro-organism.
2. Use of carbon dioxide as an electron acceptor in a recombinant chemotrophic micro-organism, wherein the micro-organism produces an organic compound under anaerobic conditions.
3. Use according to item 1 or 2, wherein the carbon dioxide serves as an electron acceptor in a process with NADH as an electron donor.
5. Use according to any of the preceding items, wherein the micro-organism produces an organic compound in a process with an excess production of ATP and/or NADH.
6. Use according to any of the preceding items, wherein the micro-organism comprises a heterologous nucleic acid sequence encoding a polypeptide from a (naturally) autotrophic organism.
7. Use according to item 6, wherein the micro-organism comprises a heterologous nucleic acid sequence encoding a first prokaryotic chaperone for said polypeptide and preferably a nucleic acid sequence encoding a second prokaryotic chaperone—different from the first—for said polypeptide.
8. Use according to item 7, wherein the chaperones are GroEL and GroES.
9. Use according to any of the preceding items, wherein the micro-organism produces an organic compound selected from the group consisting of alcohols (such as methanol, ethanol, propanol, butanol, phenol, polyphenol), ribosomal peptides, antibiotics (such as penicillin), bio-diesel, alkynes, alkenes, isoprenoids, esters, carboxylic acids (such as succinic acid, citric acid, adipic acid, lactic acid), amino acids, polyketides, lipids, and carbohydrates.

10. Use according to any of the preceding items, wherein the microorganism comprises a heterologous nucleic acid sequence functionally expressing a polypeptide selected from the group consisting of carbonic anhydrases, carboxylases, oxygenases, hydrogenases, dehydrogenases, isomerases, aldolases, transketolases, transaldolases, phosphatases, epimerases, kinases, carboxykinases, oxidoreductases, aconitases, fumarases, reductases, lactonases, phosphoenolpyruvate (PEP) carboxylases, phosphoglycerate kinases, glyceraldehyde 3-phosphate dehydrogenases, triose phosphate isomerases, fructose-1,6-bisphosphatases, sedoheptulose-1,7-bisphosphatases, phosphopentose isomerases, phosphopentose epimerase, phosphoribulokinases (PRK), glucose 6-phosphate dehydrogenases, 6-phosphogluconolactonases, 6-phosphogluconate dehydrogenases, ribulose 5-phosphate isomerases, ribulose 5-phosphate 3-epimerases, Ribulose-1,5-bisphosphate carboxylase oxygenases, lactate dehydrogenases, malate synthases, isocitrate lyases, pyruvate carboxylases, phosphoenolpyruvate carboxykinases, fructose-1,6-bisphosphatases, phosphoglucoisomerases, glucose-6-phosphatases, hexokinases, glucokinases, phosphofructokinases, pyruvate kinases, succinate dehydrogenases, citrate synthases, isocitrate dehydrogenases, α-ketoglutarate dehydrogenases, succinyl-CoA synthetases, malate dehydrogenases, nucleoside-diphosphate kinases, xylose reductases, xylitol dehydrogenases, xylose isomerases, isoprenoid synthases, and xylonate dehydratases.

11. Use according to item 10, wherein the microorganism comprises a heterologous nucleic acid sequence functionally expressing Ribulose-1,5-bisphosphate carboxylase oxygenase (Rubisco) and/or a heterologous nucleic acid sequence functionally expressing a phosphoribulokinase (PRK).

12. Use according to any of the preceding items, wherein the microorganism is selected from the group of is selected from the group consisting of Saccharomycetaceae, *Penicillium*, *Yarrowia* and *Aspergillus*.

13. Use according to any of the preceding items, wherein the carbon dioxide is used as an electron acceptor to reduce production of an NAD+-dependent side-product or NADH-dependent side-product, such as glycerol, in a process for preparing another organic compound, such as another alcohol or a carboxylic acid.

14. Recombinant micro-organism, in particular a eukaryotic micro-organism, having an enzymatic system allowing the micro-organism to use carbon dioxide as an electron acceptor under chemotrophic (non-phototrophic) conditions, wherein the microorganism is preferably as defined in the prevision items.

15. Recombinant micro-organism according to item 14, wherein the micro-organism has an enzymatic system for producing an organic compound in a process with an excess production of ATP and/or NADH.

The production of the organic compound of interest may take place in a organism known for it usefulness in the production of the organic compound of interest, with the proviso that the organism has been genetically modified to enable the use of carbon dioxide as an electron acceptor in the organism.

Although it is contemplated that the invention is interesting for the production of a variety of industrially relevant organic compounds, a method or use according the invention is in particular considered advantageous for the production of an alcohol, in particular an alcohol selected from the group of ethanol, n-butanol and 2,3-butanediol; or in the production of an organic acid/carboxylate, in particular a carboxylate selected from the group of L-lactate, 3-hydroxypropionate, D-malate, L-malate, succinate, citrate, pyruvate and itaconate.

Regarding the production of ethanol, details are found herein above, when describing the yeast cell comprising PRK and Rubisco and in the examples. The ethanol or another alcohol is preferably produced in a fermentative process.

For the production of several organic acids (carboxylates), e.g. citric acid, an aerobic process is useful. For citric acid production for instance *Aspergillus niger*, *Yarrowia lipolytica*, or another known citrate producing organism may be used.

An example of an organic acid that is preferably produced anaerobically is lactic acid. Various lactic acid producing bacterial strains and yeast strains that have been engineered for lactate production are generally known in the art.

EXAMPLES

Example 1. Construction of the Expression Vector

Phosphoribulokinase (PRK) cDNA from *Spinacia oleracea* (spinach) (EMBL accession number: X07654.1) was PCR-amplified using Phusion Hot-start polymerase (Finnzymes, Landsmeer, the Netherlands) and the oligonucleotides XbaI_prk-FW2 and RV1_XhoI_prk (Table 5), and was ligated in pCR®-Blunt II-TOPO® (Life Technologies Europe BV, Bleiswijk, the Netherlands).

TABLE 5

Oligonucleotides

| SEQ ID NO | Name | Sequence (5' to 3') | Purpose |
|---|---|---|---|
| | | Cloning | |
| 12 | XbaI_prk_FW2 | TGACATCTAGATGTCACAACAACAAACAATTG | cloning of PRK into pUDE046. |
| 13 | RV1_XhoI_prk | TGACATCTAGATGTCACAACAACAAACAATTG | cloning of PRK into pUDE046. |

TABLE 5-continued

Oligonucleotides

| SEQ ID NO | Name | Sequence (5' to 3') | Purpose |
|---|---|---|---|
| | | Primers used for in vivo plasmid assembly | |
| 14 | HR-cbbM-FW-65 | TTGTAAAACGACGGCCAGTGAGCGCGCGTAATACGACTCACTATAGGGCGAATTGGGTACAGCTGGAGCTCAGTTTATCATTATC | Rubisco cbbM cassette for plasmids pUDC075, pUDC099, and pUDC100. |
| 15 | HR-cbbM-RV-65 | GGAATCTGTGTAGTATGCCTGGAATGTCTGCCGTGCCATAGCCATGTATGCTGATATGTCGGTACCGGCCGCAAATTAAAG | Rubisco cbbM cassette for plasmids pUDC075, pUDC099, and pUDC100 |
| 16 | linker-cbbO2-pRS416 | ATCACTCTTACCAGGCTAGGACGACCCTACTCATGTATTGAGATCGACGAGATTTCTAGGCCAGCTTTTGTTCCCTTTAGTGAGGGTTAATTGCGCGCTTGGCGTAATCATGGTCATAGC | Linker fragment for assembly of plasmid pUDC099. |
| 17 | linker-cbbM-GroEL | GACATATCAGCATACATGGCTATGGCACGGCAGACATTCCAGGCATACTACACAGATTCCATCACTCTTACCAGGCTAGGACGACCCTACTCATGTATTGAGATCGACGAGATTTCTAGG | Linker fragment for assembly of plasmid pUDC100. |
| | | Primers used for in vivo integration assembly | |
| 18 | FW pTDH3-HR-CAN1up | GTTGGATCCAGTTTTTAATCTGTCGTCAATCGAAAGTTTATTTCAGAGTTCTTCAGACTTCTTAACTCCTGTAAAAACAAAAAAAAAAAAAAAGGCATAGCAAGCTGGAGCTCAGTTTATC | $1^{st}$ cloning expression cassette linker fragment between CAN1 upstream and PRK expression cassette (IMI229), and CAN1up-linker and KlLEU2 expression cassette (IMI232). |
| 19 | RV linker-iHR2B | AGATATACTGCAAAGTCCGGAGCAACAGTCGTATAACTCGAGCAGCCCTCTACTTTGTTGTTGCGCTAAGAGAATGGACC | $1^{st}$ cloning fragment: linker fragment between CAN1up-linker and PRK expression cassette (IMI229). |
| 20 | RV linker-iHR6 | GCTATGACCATGATTACGCCAAGCGCGCAATTAACCCTCACTAAAGGGAACAAAAGCTGGTTGCGCTAAGAGAATGGACC | $1^{st}$ cloning fragment: linker fragment between CAN1up-linker and KlLEU2 expression cassette (IMI232). |
| 21 | FW pGAL1-prk HR2B | CAACAAAGTAGAGGGCTGCTCGAGTTATACGACTGTTGCTCCGGACTTTGCAGTATATCTGCTGGAGCTCTAGTACGGATT | $2^{nd}$ cloning fragment: GAL1$_p$-PRK-CYC1$_t$ expression cassette (IMI229) from pUDE046. |
| 22 | RV CYC1t-prk HR2 | GGAATCTGTGTAGTATGCCTGGAATGTCTGCCGTGCCATAGCCATGTATGCTGATATGTCGTACCGGCGCAAATTAAAG | $2^{nd}$ cloning fragment: GAL1$_p$-PRK-CYC1$_t$ expression cassette (IMI229) from pUDE046. |
| 23 | FW HR2-cbbQ2-HR3 | GACATATCAGCATACATGGCTATGG | $3^{rd}$I cloning fragment: PGI1$_p$-cbbQ2-TEF2$_t$ cassette (IMI229). |
| 24 | RV HR2-cbbQ2-HR3 | GGACACGCTTGACAGAATGTCAAAGG | $3^{rd}$ cloning fragment: PGI1$_p$-cbbQ2-TEF2$_t$ cassette (IMI229). |
| 25 | FW HR3-cbbO2-HR4 | CGTCCGATATGATCTGATTGG | $4^{th}$ TARI cloning fragment: PGK1$_p$-cbbO2-ADH1$_t$ cassette (IMI229). |
| 26 | RV HR3-cbbO2-HR4 | CCTAGAAATCTCGTCGATCTC | $4^{th}$ cloning fragment: PGK1$_p$-cbbO2-ADH1$_t$ cassette (IMI229). |
| 27 | FW HR4-GroEL-HR5 | ATCACTCTTACCAGGCTAGG | $5^{th}$ cloning fragment: TEF1$_p$-groEL-ACT1$_t$ cassette (IMI229). |
| 28 | RV HR4-GroEL-HR5 | CTGGACCTTAATCGTGTGCGCATCCTC | $5^{th}$ cloning fragment: TEF1$_p$-groEL-ACT1$_t$ cassette (IMI229). |
| 29 | FW HRS-GroES-HR6 | CCGTATAGCTTAATAGCCAGCTTTATC | $6^{th}$ cloning fragment: TPI1$_p$-groES-PGI1$_t$ cassette (IMI229). |
| 30 | RV HRS-GroES-HR6 | GCTATGACCATGATTACGCCAAGC | $6^{th}$ cloning fragment: TPI1$_p$-groES-PGI1$_t$ cassette (IMI229). |
| 31 | FW HR6-LEU2-CAN1dwn | CCAGCTTTTGTTCCCTTTAGTGAGGGTTAATTGCGCGCTTGGCGTAATCATGGTCATAGCCTGTGAAGATCCAGCAAAG | $7^{th}$ (IMI229) or $2^{nd}$ (IMI232) cloning fragment: KlLEU2 cassette from pUG73. |

TABLE 5-continued

Oligonucleotides

| SEQ ID NO | Name | Sequence (5' to 3') | Purpose |
|---|---|---|---|
| 32 | RV LEU2 HR-CAN1 | AGCTCATTGATCCCTTAAACTTTCTTTTCGGTGTATGACTTATGAGGGTGAGAATGCGAAATGGCGTGGAAATGTGATCAAAGGTAATAAAACGTCATATATCCGCAGGCTAACCGGAAC | 7$^{th}$ (IMI229) or 2$^{nd}$ (IMI232) cloning fragment: KlLEU2 cassette from pUG73. |

Primers used for verification of the in vivo assembled constructs

| | | | |
|---|---|---|---|
| 33 | m-PCR-HR1-FW | GGCGATTAAGTTGGGTAACG | Diagnostic for assembly of plasmids pUDC075, pUDC099, and pUDC100,. |
| 34 | m-PCR-HR1-RV | AACTGAGCTCCAGCTGTACC | Diagnostic for assembly of plasmids pUDC075, pUDC099, pUDC100, and integration in strain IMI229. |
| 35 | m-PCR-HR2-FW | ACGCGTGTACGCATGTAAC | Diagnostic for assembly of pUDC075, pUDC099, pUDC100, and integration in strain IMI229 |
| 36 | m-PCR-HR2-RV | GCGCGTGGCTTCCTATAATC | Diagnostic for assembly of pUDC075, pUDC099, pUDC100, and integration in strain IMI229 |
| 37 | m-PCR-HR3-FW | GTGAATGCTGGTCGCTATAC | Diagnostic for assembly of pUDC075, pUDC099, pUDC100, and integration in strain IMI229. |
| 38 | m-PCR-HR3-RV | GTAAGCAGCAACACCTTCAG | Diagnostic for assembly of pUDC075, pUDC099, pUDC100, and integration in strain IMI229. |
| 39 | m-PCR-HR4-FW | ACCTGACCTACAGGAAAGAG | Diagnostic for assembly of pUDC075, pUDC099, pUDC100, and integration in strain IMI229. |
| 40 | m-PCR-HR4-RV | TGAAGTGGTACGGCGATGC | Diagnostic for assembly of pUDC075, pUDC099, pUDC100, and integration in strain IMI229. |
| 41 | m-PCR-HR5-FW | ATAGCCACCCAAGGCATTTC | Diagnostic for assembly of pUDC075, pUDC099, pUDC100, and integration in strain IMI229. |
| 42 | m-PCR-HR5-RV | CCGCACTTTCTCCATGAGG | Diagnostic for assembly of pUDC075, pUDC099, pUDC100, and integration in strain IMI229. |
| 43 | m-PCR-HR6-FW | CGACGGTTACGGTGTTAAG | Diagnostic for assembly of pUDC075, pUDC099, pUDC100, and integration in strain IMI229. |
| 44 | m-PCR-HR6-RV | CTTCCGGCTCCTATGTTGTG | Diagnostic for assembly of pUDC075, pUDC099, pUDC100, and integration in strain IMI229. |

After restriction by XbaI and XhoI, the PRK-containing fragment was ligated into pTEF424. The TEF1p was later replaced by GAL1p from plasmid pSH47 by XbaI and SacI restriction/ligation, creating plasmid pUDE046 (see Table 6).

TABLE 6

Plasmids

| Name | Relevant genotype | Source/reference |
|---|---|---|
| pFL451 | pAOX1-prk (Spinach)-AOX1t (pHIL2-D2 HIS4 Amp centromeric) | Brandes et al. 1996.[14] |
| pCR ®-Blunt II-TOPO | bla | Life Technologies Europe BV |
| pTEF424_TEF | TRP1 2μ bla | Mumberg et al. 1995[25]. |
| pSH47 | URA3 CEN6 ARS4 GAL1$_p$-cre-CYC1$_t$ bla | Güldener et al 1996[26] |
| pUD0E46 | TRP1 2μ GAL1p-prk-CYC1$_t$ bla | This study. |
| pPCR-Script | bla | Life Technologies Europe BV |
| pGPD_426 | URA3 2μ bla | Mumberg et al. 1995[25]. |
| pRS416 | URA3 CEN6 ARS4 bla | Mumberg et al. 1995[25]. |
| pBTWW002 | URA3 2μ TDH3$_p$-cbbM-CYC1$_t$ bla | This study. |
| pUDC098 | URA3 CEN6 ARS4 TDH3$_p$-cbbM-CYC1$_t$ bla | This study. |
| pMK-RQ | nptII | Life Technologies Europe BV |
| pUD230 | PGI1$_p$-cbbQ2-TEF2$_t$ nptII | Life Technologies Europe BV |
| pUD231 | PGK1$_p$-cbbO2-ADH1$_t$ nptII | Life Technologies Europe BV |
| pUD232 | TEF1$_p$-groEL-ACT1$_t$ nptII | Life Technologies Europe BV |
| pUD233 | TPI1$_p$-groES-PGI1$_t$ nptII | Life Technologies Europe BV |
| pUDC075 | URA3 CEN6 ARS4 TDH3$_p$-cbbM-CYC1$_t$;PGI1$_p$-cbbQ2-TEF2$_t$;PGK1$_p$-cbbO2-ADH1$_t$;TEF1$_p$-groEL-ACT1$_t$;TPI1$_p$-groES-PGI1$_t$ bla | This study. |
| pUDC099 | URA3 CEN6 ARS4 TDH3$_p$-cbbM-CYC1$_t$;PGI1$_p$-cbbQ2-TEF2$_t$;PGK1$_p$-cbbO2-ADH1$_t$ bla | This study. |
| pUDC100 | URA3 CEN6 ARS4 TDH3$_p$-cbbM-CYC1$_t$; TEF1$_p$-groEL-ACT1$_t$;TPI1$_p$-groES-PGI1$_t$ bla | This study. |

Rubisco form II gene cbbM from *Thiobacillus denitrificans* (*T. denitrificans*) flanked by KpnI and SacI sites was codon optimized synthesized at GeneArt (Life Technologies Europe BV), and ligated into pPCR-Script., the plasmid was then digested by BamHI and SacI. The cbbM-containing fragment was ligated into the BamHI and SacI restricted vector pGPD_426 creating plasmid pBTWW002. The cbbM expression cassette was transferred into pRS416 using KpnI and SacI, yielding pUDC098.

Expression cassette of the specific Rubisco form II cheparones from *T. denitrificans* cbbQ2 and ebbO2, and chaperones groEL and groES from *E. coli*, were condon optimized. The expression cassettes contained a yeast constitutive promoters and terminator, flanking the codon optimized gene. The cassette was flanked by unique 60 bp regions obtained by randomly combining bar-code sequences used in the *Saccharomyces* Genome Deletion Project and an EcoRV site (GeneArt). The expression cassettes were inserted in plasmid pMK-RQ (GeneArt) using the SfiI cloning sites yielding pUB230 (PGI1p-cbbQ2-TEF2t), pUD231 (PGK1p-cbbO2-ADH1t), pUD232 (TEF1p-groEL-ACT1t), and pUDE233 (TPI1p-groES-PGI1t) Table 6). The expression cassette TDH3p-cbbM-CYC1t was PCR-amplified from plasmid pBTWW002 using Phusion Hot-Start Polymerase (Finnzymes) and primers HR-cbbM-FW-65 and HR-cbbM-RV-65 in order to incorporate the 60-bp region for recombination cloning.

Example 2. Strain Construction, Isolation and Maintenance

All *Saccharomyces cerevisiae* strains used (Table 7) belong to the CEN.PK family. All strains were grown in 2% w/v glucose synthetic media supplemented with 150 mg L$^{-1}$ uracil when required until they reached end exponential phase, then sterile glycerol was added up to ca. 30% v/v and aliquots of 1 ml were stored at −80° C.

TABLE 7

Saccharomyces cerevisiae strains

| Strain | Relevant genotype | Source/reference |
|---|---|---|
| CEN.PK113-5D | MATa ura3-52 | Euroscarf |
| CEN.PK102-3A | MATa ura3-52 leu2-3, 112 | Euroscarf |
| IMC014 | MATa ura3-52 pUDC075 (CEN6 ARS4 URA3 TDH3$_p$-cbbM-CYC1$_t$ PGI1$_p$-cbbQ2-TEF2$_t$ PGK1$_p$-cbbO2-ADH1$_t$ TEF1$_p$-groEL-ACT1$_t$ TPI1$_p$-groES-PGI1$_t$) | This study. |
| IMC033 | MATa ura3-52 pUDC098 (CEN6 ARS4 URA3 TDH3$_p$-cbbM-CYC1$_t$) | This study. |
| IMC034 | MATa ura3-52 pUDC099 (CEN6 ARS4 URA3 TDH3$_p$-cbbM-CYC1$_t$ PGI1$_p$-cbbQ2-TEF2$_t$ PGK1$_p$-cbbO2-ADH1$_t$,cbbO2-pRS416 linker) | This study. |
| IMC035 | MATa ura3-52 pUDC100 (CEN6 ARS4 URA3 TEF1$_p$-groEL-ACT1$_t$ TPI1$_p$-groES-PGI1$_t$ cbbM-GroEL linker) | This study. |
| IMI229 | MATa ura3-52 leu2-3, 112 can1Δ::GAL1$_p$-prk-CYC1$_t$ PGI1$_p$-cbbQ2-TEF2$_t$,PGK1$_p$-cbbO2-ADH1$_t$,TEF1$_p$-groEL-ACT1$_t$,TPI1$_p$-groES-PGI1, KlLEU2 | This study. |
| IMI232 | MATa ura3-52 leu2-3, 112 can1Δ::KlLEU2 | This study. |
| IMU032 | IMI232 p426_GPD (2μ URA3) | This study. |
| IMU033 | IMI229 pUDC100 (CEN6 ARS4 URA3 TEF1$_p$-groEL-ACT1$_t$ TPI1$_p$-groES-PGI1$_t$ cbbM-GroEL linker) | This study. |

The strain IMC014 that co-expressed the Rubisco form II ccbM and the four chaperones cbbQ2, ebbO2, groEL, and groES was constructed using in vivo transformation associated recombination. 200 fmol of each expression cassette were pooled with 100 fmol of the KpnI/SacI linearized pRS416 backbone in a final volume of 50 μl and transformed in CEN.PK 113-5D using the lithium acetate protocol (Gietz, et al., Yeast Transformation by the LiAc/SS Carrier DNA/PEG Method in Yeast Protocol, *Humana press*, 2006). Cells were selected on synthetic medium. Correct assembly of the fragment of pUDC075 was performed by multiplex PCR on transformant colonies using primers enabling amplification over the regions used for homologous recombination (Table 5) and by restriction analysis after re-transformation of the isolated plasmid in *E. coli* DH5a. PUDC075 was sequenced by Next-Generation Sequencing (Illumina, San Diego, California, U.S.A.) (100br reads paired-end, 50 Mb) and assembled with Velvet (Zerbino, et al., Velvet: Algorithms for De Novo Short Read Assembly Using De Bruijn Graphs, *Genome Research*, 2008). The assembled sequence did not contain mutations in any of the assembled expression cassettes. The strains IMC034 and IMC035 that expressed ccbM/ccbQ2/ccbO2 and ccbM/groEL/groES respectively were constructed using the same in vivo assembly method with the following modification. To construct plasmids pUDC099 and pUDC100, 120 bp cbbO2-pRS416 linker and cbbM-GroEL linker were used to close the assembly respectively (Table 5), 100 fmol of each of complementary 120 bp oligonucleotides were added to the transformation. The strain IMC033 that only expressed the cbbM gene was constructed by transforming CEN.PK113-5D with pUDC098.

To construct the strain IMU033 that co-expressed PRK, ccbM, ccbQ2, ccbO2, GroEL, GroES, the intermediate strain IMI229 was constructed by integrating PRK, the four chaperones and KlLEU2 (Güldener, et al., A second set of loxP marker cassettes for Cre-mediated multiple gene knockouts in budding yeast, Nucleic Acids Research, 2002) at the CAN1 locus by in vivo homologous integration in CEN.PK102-3A. The expression cassettes were PCR amplified using Phusion Hot-Start Polymerase (Finnzymes, Thermo Fisher Scientific Inc. Massachusetts, U.S.A.), the corresponding oligonucleotides and DNA templates (Table 5). Finally, the strain IMI229 was transformed with pUDC100 that carries the Rubisco form II ccbM and the two *E. coli* chaperones groEL and groES.

Strain IMI232 was constructed by transforming CEN.PK102-3A with the KlLEU2 cassette. IMI232 was finally transformed with the plasmid p426GPD to restore prototrophy resulting in the reference strain IMU032.

Example 3. Experimental Set-Up of Chemostat and Batch Experiments

Anaerobic chemostat cultivation was performed essentially as described (Basso, et al., Engineering topology and kinetics of sucrose metabolism in *Saccharomyces cerevisiae* for improved ethanol yield, Metabolic Engineering 13:694-703, 2011), but with 12.5 g 1-1 glucose and 12.5 g 1-1 galactose as the carbon source and where indicated, a mixture of 10% $CO_2$/90% $N_2$ replaced pure nitrogen as the sparging gas. Residual glucose and galactose concentrations were determined after rapid quenching (Mashego, et al., Critical evaluation of sampling techniques for residual glucose determination in carbon-limited chemostat culture of *Saccharomyces cerevisiae*, Biotechnology and Bioengineering 83:395-399, 2003) using commercial enzymatic assays for glucose (Boehringer, Mannheim, Germany) and D-galactose (Megazyme, Bray, Ireland). Anaerobic bioreactor batch cultures were grown essentially as described (Guadalupe Medina, et al., Elimination of glycerol production in anaerobic cultures of a *Saccharomyces cerevisiae* strain engineered to use acetic acid as an electron acceptor. *Applied and Environmental Microbiology* 76:190-195, 2010), but with 20 g $L^{-1}$ galactose and a sparging gas consisting of 10% $CO_2$ and 90% $N_2$. Biomass and metabolite concentrations in batch and chemostat and batch cultures were determined as described by Guadalupe et al. (Guadalupe Medina, et al., Elimination of glycerol production in anaerobic cultures of a *Saccharomyces cerevisiae* strain engineered to use acetic acid as an electron acceptor. Appl. Environ. Microbiol. 76, 190-195, 2010). In calculations of ethanol fluxes and yields, ethanol evaporation was corrected for based on a first-order evaporation rate constant of 0.008 $h^{-1}$ in the bioreactor set-ups and under the conditions used in this study.

Example 4. Enzyme Assays for Phosphoribulokinase (PRK) and Rubisco

Cell extracts for analysis of phosphoribulokinase (PRK) activity were prepared as described previously (Abbott, et al., Catalase Overexpression reduces lactic acid-induced oxidative stress in *Saccharomyces cerevisiae, Applied and Environmental Microbiology* 75:2320-2325, 2009). PRK activity was measured at 30° C. by a coupled spectrophotometric assay (MacElroy, et al., Properties of Phosphoribulokinase from *Thiobacillus neapolitanus, Journal of Bacteriology* 112:532-538, 1972). Reaction rates were proportional to the amounts of cell extract added. Protein concentrations were determined by the Lowry method (Lowry, et al., Protein measurement with the Folin phenol reagent, *The Journal of Biological Chemistry* 193:265-275, 1951) using bovine serum albumin as a standard.

Cell extracts for Rubisco activity assays were prepared as described in Abbott, D. A. et al. Catalase overexpression reduces lactic acid-induced oxidative stress in *Saccharomyces cerevisiae*. Appl. Environ. Microbiol. 75:2320-2325, 2009, with two modifications: Tris-HCl (1 mM, pH 8.2) containing 20 mM $MgCl_2.6H_2O$, 5 mM of DTT 5 mM $NaHCO_3$ was used as sonication buffer and Tris-HCl (100 mM, pH 8.2), 20 mM $MgCl_2.6H_2O$ and 5 mM of DTT as freezing buffer. Rubisco activity was determined by measuring $^{14}CO_2$-fixation (PerkinElmer, Groningen, The Netherlands) as described (Beudeker, et al., Relations between d-ribulose-1,5-biphosphate carboxylase, carboxysomes and $CO_2$ fixing capacity in the obligate chemolithotroph *Thiobacillus neapolitanus* grown under different limitations in the chemostat, Archives of Microbiology 124:185-189, 1980) and measuring radioactive counts in a TRI-CARB® 2700TR Series liquid scintillation counter (PerkinElmer, Groningen, The Netherlands), using Ultima Gold™ scintillation cocktail (PerkinElmer, Groningen, The Netherlands). Protein concentrations were determined by the Lowry method (Lowry, O. H., Rosebrough, N. J., Farr, A. L., & Randall, R. J. Protein measurement with the Folin phenol reagent. J. Biol. Chem. 193:265-275, 1951) using standard solutions of bovine serum albumin dissolved in 50 mM Tris-HCl (pH 8.2).

Example 5. The Activity of Rubisco and the Activity of PRK in Cell Extracts

In order to study a possible requirement of heterologous chaperones of Rubisco in *S. cerevisiae*, the form-II Rubisco-encoding cbbM gene from *T. denitrificans* was codon-optimised and expressed from a centromeric vector, both alone and in combination with expression cassettes for the codon-optimised *E. coli* groEL/groES and/or *T. denitrificans* cbbO2/cbbQ2 genes. Analysis of ribulose-1,5-biphosphate-dependent $CO_2$ fixation by yeast cell extracts demonstrated that functional expression of *T. denitrificans* Rubisco in *S. cerevisiae* was observed upon co-expression of *E. coli* GroEL/GroES. Rubisco activity increased from <0.2 $nmol·min^{-1}·(mg\ protein)^{-1}$ to more than 6 $nmol·min^{-1}·(mg\ protein)^{-1}$. Results of these experiments are visualised in FIG. 1, showing specific ribulose-1,5-bisphosphate carboxylase (Rubisco) activity in cell extracts of *S. cerevisiae* expressing Rubisco form II CbbM from *T. denitrificans* either alone (IMC033) or in combination with the *E. coli* chaperones GroEL/GroES (IMC035), The *T. denitrificans* chaperones CbbO2/CbbQ2 [20] (IMC034) or all four chaperones (IMC014). Heterologously expressed genes were codon optimised for expression in yeast and expressed from a single centromeric vector. Biomass samples were taken from anaerobic batch cultures on synthetic media (pH 5.0, 30° C.), sparged with nitrogen and containing 20 g l-1 glucose as carbon source. Rubisco activities, measured as14CO2-fixation in cell extracts, in a wild-type reference strain and in *S. cerevisiae* strains expressing cbbM and cbbM-cbbQ2-cbbO2 were below the detection limit of the enzyme assay (0.2 nmol CO2 min–1 mg protein–1

Co-expression of CbbO2/cbbQ2 did not result in a significant further increase of Rubisco activity. The positive effect of GroEL/GroES on Rubisco expression in *S. cerevisiae* demonstrates the potential value of this approach for metabolic engineering, especially when prokaryotic enzymes need to be functionally expressed in the cytosol of eukaryotes.

The Spinach *oleracea* PRK gene was integrated together with *E. coli* groEL/groES and *T. denitrificans* cbbO2/cbbQ2 into the *S. cerevisiae* genome at the CAN1 locus, under control of the galactose-inducible GAL1 promoter. This induced in high PRK activities in cell extracts of *S. cerevisiae* strain IMU033, which additionally carried the centromeric expression cassette for *T. denitrificans* Rubisco. This engineered yeast strain was used to quantitatively analyze the physiological impacts of the expression of Rubisco and PRK.

TABLE 8

|  | IMU032 (reference strain) | | IMU033 (expressing PRK and Rubisco) | |
|---|---|---|---|---|
| $CO_2$ in inlet gas (%) | 0 | 10 | 0 | 10 |
| $CO_2$ in outlet gas (%) | 0.89 ± 0.03 | 10.8 ± 0.0 | 1.02 ± 0.00 | 10.8 ± 0.1 |
| Phosphoribulokinase ($\mu mol\ mg\ protein^{-1}\ min^{-1}$) | 0.58 ± 0.09 | 0.51 ± 0.12 | 14.4 ± 1.5 | 15.2 ± 1.0 |
| Rubisco (nmol mg $protein^{-1}\ min^{-1}$) | <0.2* | <0.2 | 4.59 ± 0.30 | 2.67 ± 0.28 |
| Biomass yield on sugar ($g\ g^{-1}$) | 0.083 ± $0.000^a$ | 0.084 ± $0.000^b$ | 0.093 ± $0.001^a$ | 0.095 ± $0.000^b$ |
| Ethanol yield on sugar ($mol\ mol^{-1}$) | 1.56 ± $0.03^c$ | 1.56 ± $0.02^d$ | 1.73 ± $0.02^c$ | 1.73 ± $0.01^d$ |
| Glycerol yield on sugar ($mol\ mol^{-1}$) | 0.14 ± $0.00^e$ | 0.12 ± $0.00^f$ | 0.04 ± $0.00^{e,\ g}$ | 0.01 ± $0.00^{f,\ g}$ |

Table 8 show increased ethanol yields on sugar of an *S. cerevisiae* strain expressing phosphoribulokinase (PRK) and Rubisco. Physiological analysis of *S. cerevisiae* IMU033 expressing PRK and Rubisco and the isogenic reference strain IMU032 in anaerobic chemostat cultures, grown at a dilution rate of 0.05 h–1 on a synthetic medium (pH 5) supplemented with 12.5 g 1-1 glucose and 12.5 g 1-1 galactose as carbon sources. To assess the impact of CO2 concentration, chemostat cultures were run sparged either with pure nitrogen gas or with a blend of 10% CO2 and 90% nitrogen. Results are represented as average ±mean deviations of data from independent duplicate chemostat experiments. Data pairs labelled with the same subscripts (a,a, b,b, etc.) are considered statistically different in a standard t-test (p<0.02).

Expression of Rubisco and the four chaperones without co-expression of PRK (strain IMC014) did not result in decreased glycerol yield (0.13 mol $mol^{-1}$) compared to the reference strain IMU032 (0.12 mol $mol^{-1}$) in carbon-limited chemostat cultures supplemented with $CO_2$, indicating that expression of a phosphoribulokinase (PRK) gene is required for the functional pathway in *S. cerevisiae* to decrease glycerol production. The physiological impact of expression of PRK and Rubisco on growth, substrate consumption and product formation in galactose-grown anaerobic batch cultures of *S. cerevisiae* was also investigated and compared with an isogenic reference strain. Growth conditions: T=30° C., pH 5.0, 10% $CO_2$ in inlet gas. Two independent replicate experiments were carried out, whose growth kinetic parameters differed by less than 5%. Ethanol yield on galactose was 8% higher and glycerol production was reduced by 60% in the yeast cell in which PRK and Rubisco were functionally expressed, compared to the yeast cell lacking these enzymes. The differences were statistically significant (standard t-test (p value <0.02). The activities of phosphoribulokinase and of Rubisco in cell extracts of the engineered strain IMU033 (table 7) enable the use of $CO_2$ as an electron acceptor. The ethanol yields and glycerol yields of strain IMU033 relative to the reference strain IMU032 (table 8) show that this is possible in an anaerobic fermentation with increased ethanol production.

```
SEQUENCES
Rubisco cbbM gene (synthetic; based on cbbM gene from
thiobacillus denitrificans-pBTWW002, codon optimized Source:
Hernandez et al 1996, GenBank ID: L37437.2)
                                                      SEQ ID NO: 1
ATGGATCAATCTGCAAGATATGCTGACTTGTCTTTAAAGGAAGAAGATTTGATTAAAGGTG

GTAGACATATTTTGGTTGCTTACAAAATGAAACCAAAATCTGGTTATGGTTATTTGGAAGC

TGCTGCTCATTTTGCTGCTGAATCTTCTACAGGTACAAATGTTGAAGTTTCTACTACAGATG

ATTTTACAAAAGGTGTTGATGCTTTAGTTTACTACATCGATGAAGCTTCAGAAGATATGAG

AATTGCTTATCCATTGGAATTATTCGACAGAAATGTTACTGACGGAAGATTCATGTTAGTTT

CTTTTTTGACTTTGGCTATTGGTAACAATCAAGGAATGGGAGATATAGAACATGCAAAAAT

GATAGATTTTTACGTTCCAGAAAGATGTATTCAAATGTTTGATGGTcCAGCTACAGATATTT

CTAATTTGTGGAGAATTTTGGGTAGACCAGTAGTTAATGGTGGTTATATTGCTGGTACTAT

TATTAAGCCAAAATTGGGTTTAAGACCAGAAcCATTTGCTAAAGCTGCTTATCAATTTTGG

TTGGGTGGAGATTTTATCAAGAATGACGAACCACAAGGTAATCAAGTTTTTTGTCCATTGA

AAAAGTTTTGCCATTGGTTTACGATGCTATGAAAAGAGCACAAGATGATACTGGTCAAGC

AAAATTGTTTTCTATGAATATTACTGCAGACGATCATTATGAAATGTGTGCAAGAGCTGAT

TATGCTTTGGAAGTTTTCGGTCCAGATGCAGATAAATTGGCTTTTTTGGTAGATGGTTACG

TTGGAGGTCCAGGAATGGTTACTACTGCTAGAAGGCAATATCCTGGTCAATATTTGCATTA

TCATAGAGCAGGTCACGGTGCTGTTACTTCTCCATCTGCTAAAAGAGGTTATACTGCTTTT

GTTTTGGCTAAAATGTCTAGATTGCAAGGCGCTTCAGGTATTCATGTTGGTACTATGGGTT

ATGGAAAAATGGAAGGAGAAGGCGACGATAAGATTATTGCTTATATGATAGAAAGGGACG

AATGTCAAGGTCCAGTTTATTTTCAAAAATGGTACGGTATGAAACCAACTACTCCAATTAT

CTCCGGAGGAATGAATGCTTTGAGATTGCCTGGTTTTTTCGAAAATTTGGGTCATGGTAAC

GTTATTAATACTGCAGGTGGTGGTTCTTACGGTCATATTGATTCTCCTGCTGCTGGTGCTA

TTTCTTTGAGACAATCTTACGAATGTTGGAAACAAGGTGCAGATCCAATTGAATTTGCTAA

GGAACATAAGGAATTTGCAAGAGCTTTTGAATCTTTTCCAAAAGATGCTGATAAGTTATTT

CCAGGATGGAGAGAAAAATTGGGAGTTCATTCTTAA

Translated protein sequence of cbbM gene from Thiobacillus
denitrificans
                                                      SEQ ID NO: 2
MDQSARYADLSLKEEDLIKGGRHILVAYKMKPKSGYGYLEAAAHFAAESSTGTNVEVSTTD

DFTKGVDALVYYIDEASEDMRIAYPLELFDRNVTDGRFMLVSFLTLAIGNNQGMGDIEHAK

MIDFYVPERCIQMFDGPATDISNLWRILGRPVVNGGYIAGTIIKPKLGLRPEPFAKAAYQFWL

GGDFIKNDEPQGNQVFCPLKKVLPLVYDAMKRAQDDTGQAKLFSMNITADDHYEMCARAD

YALEVFGPDADKLAFLVDGYVGGPGMVTTARRQYPGQYLHYHRAGHGAVTSPSAKRGYTA

FVLAKMSRLQGASGIHVGTMGYGKMEGEGDDKIIAYMIERDECQGPVYFQKWYGMKPTTP

IISGGMNALRLPGFFENLGHGNVINTAGGGSYGHIDSPAAGAISLRQSYECWKQGADPIEFA

KEHKEFARAFESFPKDADKLFPGWREKLGVHS
```

-continued prk gene from *Spinacea oleracea*-pBTWW001, plasmid constructed
using restriction and ligation. Source: Milanez and Mural
1988, GenBank ID: M21338.1

SEQ ID NO: 3
ATGTCACAACAACAAACAATTGTGATTGGTTTAGCAGCAGATTCAGGTTGTGGTAAGAGTA

CATTCATGAGGAGGTTAACAAGTGTTTTCGGTGGCGCGGCCGAGCCACCAAAGGGTGGTA

ACCCAGATTCAAACACATTGATTAGTGACACTACTACTGTTATCTGTTTGGATGATTTTCAT

TCCCTTGATAGAAATGGCAGGAAAGTGGAAAAAGTTACTGCTTTAGACCCAAAAGCTAATG

ATTTTGATCTTATGTATGAACAAGTTAAGGCTTTGAAAGAAGGTAAAGCTGTTGATAAACC

TATTTATAATCATGTTTCTGGTTTGTTGGACCCTCCTGAGCTTATTCAACCTCCTAAGATCT

TGGTCATTGAAGGGTTACACCCCATGTATGACGCACGTGTGAGGGAATTGCTAGACTTCAG

CATCTACTTGGACATTAGCAATGAAGTTAAATTTGCCTGGAAAATTCAGAGAGACATGAAA

GAAAGAGGACACAGTCTTGAAAGCATCAAAGCCAGTATTGAATCCAGAAAGCCAGATTTTG

ATGCTTACATTGACCCACAAAAGCAGCATGCTGATGTAGTGATTGAAGTATTGCCAACTGA

ACTCATTCCTGATGATGATGAAGGCAAAGTGTTGAGAGTAAGGATGATTCAGAAAGAAGG

AGTCAAGTTTTTCAACCCAGTTTACTTGTTTGATGAAGGATCTACCATTTCATGGATTCCAT

GTGGTAGAAAATTAACATGTTCTTACCCTGGTATCAAATTTTCCTATGGCCCAGACACCTT

CTATGGCAACGAGGTGACAGTAGTAGAGATGGATGGGATGTTTGACAGATTAGACGAACT

AATCTACGTCGAAAGCCATTTGAGCAATCTATCAACCAAGTTTTATGGTGAAGTCACTCAA

CAAATGTTGAAGCACCAAAATTTCCCAGGAAGCAACAATGGAACTGGTTTCTTCCAAACCA

TAATTGGATTGAAGATCAGAGACTTGTTCGAGCAGCTCGTTGCTAGCAGGTCTACAGCAAC

TGCAACAGCTGCTAAAGCCTAG

Translated protein sequence of prk gene from *Spinacea oleracea*
SEQ ID NO: 4
MSQQQTIVIGLAADSGCGKSTFMRRLTSVFGGAAEPPKGGNPDSNTLISDTTTVICLDDFHS

LDRNGRKVEKVTALDPKANDFDLMYEQVKALKEGKAVDKPIYNHVSGLLDPPELIQPPKIL

VIEGLHPMYDARVRELLDFSIYLDISNEVKFAWKIQRDMKERGHSLESIKASIESRKPDFDA

YIDPQKQHADVVIEVLPTELIPDDDEGKVLRVRMIQKEGVKFFNPVYLFDEGSTISWIPCGR

KLTCSYPGIKFSYGPDTFYGNEVTVVEMDGMFDRLDELIYVESHLSNLSTKFYGEVTQQML

KHQNFPGSNNGTGFFQTIIGLKIRDLFEQLVASRSTATATAAKA

SEQ ID NO: 5
cbbQ2 gene (synthetic, based on cbbQ2 gene from *Thiobacillus
denitrificans*-codon optimized, original sequence obtained
from Beller et al 2006, GenBank Gene ID: 3672366, Protein ID:
AAZ98590.1
ATGACTACTAACAAGGAACAATACAAGGTTCACCAAGAACCATACTACCAAGCTCAAGGTA

GAGAAGTTCAATTGTACGAAGCTGCTTACAGAAACAGATTGCCAGTTATGGTTAAGGGTCC

AACTGGTTGTGGTAAGTCTAGATTCGTTGAATACATGGCTTGGAAGTTGAACAAGCCATTG

ATCACTGTTGCTTGTAACGAAGACATGACTGCTTCTGACTTGGTTGGTAGATACTTGTTGG

AAGCTAACGGTACTAGATGGTTGGACGGTCCATTGACTACTGCTGCTAGAATCGGTGCTAT

CTGTTACTTGGACGAAGTTGTTGAAGCTAGACAAGACACTACTGTTGTTATCCACCCCATTG

ACTGACCACAGAAGAACTTTGCCATTGGACAAGAAGGGTGAATTGATCGAAGCTCACCCA

GACTTCCAATTGGTTATCTCTTACAACCCAGGTTACCAATCTTTGATGAAGGACTTGAAGC

AATCTACTAAGCAAAGATTCGCTGCTTTCGACTTCGACTACCCAGACGCTGCTTTGGAAAC

TACTATCTTGGCTAGAGAAACTGGTTTGGACGAAACTACTGCTGGTAGATTGGTTAAGATC

GGTGGTGTTGCTAGAAACTTGAAGGGTCACGGTTTGGACGAAGGTATCTCTACTAGATTGT

-continued

TGGTTTACGCTGCTACTTTGATGAAGGACGGTGTTGACGCTGGTGACGCTTGTAGAATGGC

TTTGGTTAGACCAATCACTGACGACGCTGACATCAGAGAAACTTTGGACCACGCTATCGAC

GCTACTTTCGCTTAA

Translated protein sequence of cbbQ2 gene from *Thiobacillus denitrificans*
SEQ ID NO: 6
MTTNKEQYKVHQEPYYQAQGREVQLYEAAYRNRLPVMVKGPTGCGKSRFVEYMAWKLNK

PLITVACNEDMTASDLVGRYLLEANGTRWLDGPLTTAARIGAICYLDEVVEARQDTTVVIHP

LTDHRRTLPLDKKGELIEAHPDFQLVISYNPGYQSLMKDLKQSTKQRFAAFDFDYPDAALE

TTILARETGLDETTAGRLVKIGGVARNLKGHGLDEGISTRLLVYAATLMKDGVDAGDACRM

ALVRPITDDADIRETLDHAIDATFA cbbO2 gene (Synthetic, based on cbbO2 gene from *Thiobacillus denitrificans*-codon optimized, original sequence obtained from Beller et al 2006, GenBank Gene ID: 3672365, Protein ID: YP_316394.1
SEQ ID NO: 7
ATGGCTGCTTACTGGAAGGCTTTGGACACTAGATTCGCTCAAGTTGAAGAAGTTTTCGACG

ACTGTATGGCTGAAGCTTTGACTGTTTTGTCTGCTGAAGGTGTTGCTGCTTACTTGGAAGC

TGGTAGAGTTATCGGTAAGTTGGGTAGAGGTGTTGAACCAATGTTGGCTTTCTTGGAAGAA

TGGCCATCTACTGCTCAAGCTGTTGGTGAAGCTGCTTTGCCAATGGTTATGGCTTTGATCC

AAAGAATGCAAAGTCTCCAAACGGTAAGGCTATCGCTCCATTCTTGCAAACTTTGGCTCC

AGTTGCTAGAAGATTGCAATCTGCTGAACAATTGCAACACTACGTTGACGTTACTTTGGAC

TTCATGACTAGAACTACTGGTTCTATCCACGGTCACCACACTACTTTCCCATCTCCAGGTTT

GCCAGAATTCTTCGCTCAAGCTCCAAACTTGTTGAACCAATTGACTTTGGCTGGTTTGAGA

AACTGGGTTGAATACGGTATCAGAAACTACGGTACTCACCCAGAAAGACAACAAGACTACT

TCTCTTTGCAATCTGCTGACGCTAGAGCTGTTTTGCAAAGAGAAAGACACGGTACTTTGTT

GGTTGACGTTGAAAGAAAGTTGGACTTGTACTTGAGAGGTTTGTGGCAAGACCACGACCA

CTTGGTTCCATACTCTACTGCTTTCGACGAAATCAGAAAGCCAGTTCCATACTACGACAAG

TTGGGTATGAGATTGCCAGACGTTTACGACGACTTGGTTTTGCCATGTCCAGCTGGTAGAG

GTGGTGCTGGTGGTGAAGACGTTTTGGTTTCTGGTTTGGACAGATACAGAGCTACTTTGGC

TCACATGGTTGGTCACAGAAGATGGTCTGAAGCTCAAATCGCTGACAACTGGTCTCCATTC

CAAAGAATGGCTGTTGAATTCTTCGAAGACTGTAGAGTTGAAACTTTGTTGATGAGAGAAT

ACCCAGGTTTGGCTAGAATCTTCAGAGCTTTGCACCCAAAGCCAGTTGAAGCTGCTTGTGA

CGGTGAAACTACTTCTTGTTTGAGACACAGATTGGCTATGTTGTCTAGAGCTTTCATCGAC

CCAGACCACGGTTACGCTGCTCCAGTTTTGAACGACTTCGTTGCTAGATTCCACGCTAGAT

TGGCTGACGGTACTTCTTCTACTTCTGAAATGGCTGACTTGGCTTTGTCTTACGTTGCTAA

GACTAGAAGACCATCTGACCAATTCGCTAAGGTTCACTTCGACGACACTGTTGTTGACTAC

AGAGACGACAACAGACAATTGTGGAAGTTCATCGAAGAAGGTGACGAAGAAGAAGCTTTC

GACGCTAAGAGAAAGATCGAACCAGGTGAAGAAATCCAAGGTTTGCCACCAAGACACTAC

CCAGAATGGGACTACACTTCTCAAACTTACAGACCAGACTGGGTTTCTGTTTACGAAGGTT

TGCACAGATCTGGTAACGCTGGTGACATCGACAGATTGTTGGCTAAGCACGCTGCTTTGGC

TAAGAGATTGAAGAAGATGTTGGACTTGTTGAAGCCACAAGACAAGGTTAGAGTTAGATAC

CAAGAAGAAGGTTCTGAATTGGACTTGGACGTTGCTATCAGATCTTTGATCGACTTCAAGG

GTGGTGCTACTCCAGACCCAAGAATCAACATGTCTCACAGATCTGACGGTAGAGACATCGC

-continued

```
TGTTATGTTGTTGTTGGACTTGTCTGAATCTTTGAACGAAAAGGCTGCTGGTGCTGGTCAA

ACTATCTTGGAATTGTCTCAAGAAGCTGTTTCTTTGTTGGCTTGGTCTATCGAAAAGTTGG

GTGACCCATTCGCTATCGCTGGTTTCCACTCTAACACTAGACACGACGTTAGATACTTCCA

CATCAAGGGTTACTCTGAAAGATGGAACGACGACGTTAAGGCTAGATTGGCTGCTATGGA

AGCTGGTTACTCTACTAGAATGGGTGCTGCTATGAGACACGCTGCTCACTACTTGTCTGCT

AGACCAGCTGACAAGAAGTTGATGTTGATCTTGACTGACGGTAGACCATCTGACGTTGACG

CTGCTGACGAAAGATTGTTGGTTGAAGACGCTAGACAAGCTGTTAAGGAATTGGACAGAC

AAGGTATCTTCGCTTACTGTATCTCTTTGGACGCTCAATTGAAGGCTGGTGCTGACGACTA

CGTTGCTGAAATCTTCGGTAGACAATACACTGTTATCGACAGAGTTGAAAGATTGCCAGAA

AGATTGCCAGAATTGTTCATGGCTTTGACTAAGTAA
```

Translated protein sequence of cbbO2 gene from *Thiobacillus denitrificans*

SEQ ID NO: 8

```
MAAYWKALDTRFAQVEEVFDDCMAEALTVLSAEGVAAYLEAGRVIGKLGRGVEPMLAFLE

EWPSTAQAVGEAALPMVMALIQRMQKSPNGKAIAPFLQTLAPVARRLQSAEQLQHYVDVTL

DFMTRTTGSIHGHHTTFPSPGLPEFFAQAPNLLNQLTLAGLRNWVEYGIRNYGTHPERQQD

YFSLQSADARAVLQRERHGTLLVDVERKLDLYLRGLWQDHDHLVPYSTAFDEIRKPVPYYD

KLGMRLPDVYDDLVLPCPAGRGGAGGEDVLVSGLDRYRATLAHMVGHRRWSEAQIADNW

SPFQRMAVEFFEDCRVETLLMREYPGLARIFRALHPKPVEAACDGETTSCLRHRLAMLSRA

FIDPDHGYAAPVLNDFVARFHARLADGTSSTSEMADLALSYVAKTRRPSDQFAKVHFDDTV

VDYRDDNRQLWKFIEEGDEEEAFDAKRKIEPGEEIQGLPPRHYPEWDYTSQTYRPDWVSVY

EGLHRSGNAGDIDRLLAKHAALAKRLKKMLDLLKPQDKVRVRYQEEGSELDLDVAIRSLID

FKGGATPDPRINMSHRSDGRDIAVMLLLDLSESLNEKAAGAGQTILELSQEAVSLLAWSIEK

LGDPFAIAGFHSNTRHDVRYFHIKGYSERWNDDVKARLAAMEAGYSTRMGAAMRHAAHYL

SARPADKKLMLILTDGRPSDVDAADERLLVEDARQAVKELDRQGIFAYCISLDAQLKAGAD

DYVAEIFGRQYTVIDRVERLPERLPELFMALTK
```

GroEL gene (synthetic, based on GroEL from *E. coli*-codon optimized, original sequence obtained from Durfee et al 2008, Gene ID: 6061450, Protein ID: YP_001732912.1

SEQ ID NO: 9

```
ATGGCTGCTAAGGACGTTAAGTTCGGTAACGACGCTAGAGTTAAGATGTTGAGAGGTGTT

AACGTTTTGGCTGACGCTGTTAAGGTTACTTTGGGTCCAAAGGGTAGAAACGTTGTTTGG

ACAAGTCTTTCGGTGCTCCAACTATCACTAAGGAGGGTGTTTCTGTTGCTAGAGAAATCGA

ATTGGAAGACAAGTTCGAAAACATGGGTGCTCAAATGGTTAAGGAAGTTGCTTCTAAGGCT

AACGACGCTGCTGGTGACGGTACTACTACTGCTACTGTTTTGGCTCAAGCTATCATCACTG

AACGACGCTGCTGGTGACGGTACTACTACTGCTACTGTTTTGGCTCAAGCTATCATCACTG

AAGGTTTGAAGGCTGTTGCTGCTGGTATGAACCCAATGGACTTGAAGAGAGGTATCGACA

AGGCTGTTACTGCTGCTGTTGAAGAATTGAAGGCTTTGTCTGTTCCATGTTCTGACTCTAA

GGCTATGGCTCAAGTTGGTACTATCTCTGCTAAGTCTGACGAAACTGTTGGTAAGTTGATC

GCTGAAGCTATGGACAAGGTTGGTAAGGAAGGTGTTATCACTGTTGAAGACGGTACTGGT

TTGCAAGACGAATTGGAGGTTGTTGAAGGTATGGAATTCGACAGAGGTTACTTGTGTCCAT

ACTTCATCAACAAGCCAGAAACTGGTGCTGTTGAATTGGAATCTCCATTCATCTTGTTGGC

TGACAAGAAGATCTCTAACATCAGAGAAATGTTGGCAGTTTTGGAAGCTGTTGCTAAGGCT

GGTAAGCCATTGTTGATCATCGCTGAAGACGTTGAAGGTGAAGCTTTGGCTACTTTGGTTG
```

-continued

```
TTAACACTATGAGAGGTATCGTTAAGGTTGCTGCTGTTAAGGGTCCAGGTTTCGGTGAGAG

AAGAAAGGCTATGTTGCAAGACATCGCTACTTTGACTGGTGGTACTGTTATCTCTGAAGAA

ATCGGTATGGAATTGGAAAAGGGTACTTTGGAAGACTTGGGTCAAGCTAAGAGAGTTGTTA

TCAACAAGGACACTACTACTATCATCGACGGTGTTGGTGAAGAAGCTGCTATCCAAGGTAG

AGTTGCTCAAATCAGACAACAAATCGAAGAAGCTACTTCTGACTACGACAGAGAAAAGTTG

CAAGAAAGAGTTGCTAAGTTGGCTGGTGGTGTTGGTGTTATGAAGGTTGGTGCTGCTACTG

AAGTTGAAATGAAGGAAAAGAAGGCTAGAGTTGAAGACGCTTTGCACGCTACTAGAGCTG

CTGTTGAAGAAGGTGTTGTTGCTGGTGGTGGTGTTGCTTTGATCAGAGTTGCTTCTAAGTT

GGCTGACTTGAGAGGTCAAAACGAAGACCAAAACGTTGGTATCAAGGTTGCTTTGAGAGC

TATGGAAGCTCGATTGAGACAAATCGTTTTGAACTGTGGTGAAGAACCATCTGTTGTTGCT

AACACTGTTAAGGGTGGTGACGGTAACTACGGTTACAACGCTGCTACTGAAGAATACGGT

AACATGATCGACATGGGTATCTTGGACCCAAGTAAGGTTACTAGATCTGCTTTGCAATAGG

CTGCTTCTGTTGCTGGTTTGATGATCACTACTGAATGTATGGTTACTGACTTGCCAAAGAA

CGACGCTGCTGACTTGGGTGCTGCTGGTGGTATGGGTGGTATGGGTGGTATGGGTGGTAT

GATGTAA
```

Translated protein sequence of GroEL gene from *E. coli*
SEQ ID NO: 10

MAAKDVKFGNDARVKMLRGVNVLADAVKVTLGPKGRNVVLDKSFGAPTITKDGVSVAREI
ELEDKFENMGAQMVKEVASKANDAAGDGTTTATVLAQAIITEGLKAVAAGMNPMDLKRGI
DKAVTAAVEELKALSVPCSDSKAIAQVGTISANSDETVGKLIAEAMDKVGKEGVITVEDGTG
LQDELDVVEGMQFDRGYLSPYFINKPETGAVELESPFILLADKKISNIREMLPVLEAVAKAG
KPLLIIAEDVEGEALATLVVNTMRGIVKVAAVKAPGFGDRRKAMLQDIATLTGGTVISEEIG
MELEKATLEDLGQAKRVVINKDTTTIIDGVGEEAAIQGRVAQIRQQIEEATSDYDREKLQER
VAKLAGGVAVIKVGAATEVEMKEKKARVEDALHATRAAVEEGVVAGGGVALIRVASKLADL
RGQNEDQNVGIKVALRAMEAPLRQIVLNCGEEPSVVANTVKGGDGNYGYNAATEEYGNMI
DMGILDPTKVTRSALQYAASVAGLMITTECMVTDLPKNDAADLGAAGGMGGMGGMGGMM

GroES gene (synthetic, based on GroES *E. coli*-codon optimized, original sequence obtained from Durfee et al 2008, Gene ID: 6061370, Protein ID: YP_001732911.1
SEQ ID NO: 11

```
ATGAACATCAGACCATTGCACGACAGAGTTATCGTTAAGAGAAAGGAAGTTGAAACTAAGT

CTGCTGGTGGTATCGTTTTGACTGGTTCTGCTGCTGCTAAGTCTACTAGAGGTGAAGTTTT

GGCTGTTGGTAACGGTAGAATCTTGGAAAACGGTGAAGTTAAGCCATTGGACGTTAAGGT

TGGTGACATCGTTATCTTCAACGACGGTTACGGTGTTAAGTCTGAAAAGATCGACAACGAA

GAAGTTTTGATCATGTCTGAATCTGACATCTTGGCTATCGTTGAAGCTTAA
```

Translated protein sequence of GroES gene from *E. coli*
SEQ ID NO: 12
MNIRPLHDRVIVKRKEVETKSAGGIVLTGSAAAKSTRGEVLAVGNGRILENGEVKPLDVKV
GDIVIFNDGYGVKSEKIDNEEVLIMSESDILAIVEA

---

What is claimed is:

1. A recombinant yeast cell comprising:
   one or more recombinant heterologous, nucleic acid sequences encoding Ribulose-1,5-bisphosphate carboxylase oxygenase (Rubisco) and phosphoribulokinase (PRK), wherein the amino acid sequence of the Rubisco has at least 80% sequence identity with the sequence of SEQ ID NO: 2, and
   the amino acid sequence of the PRK has at least 70% sequence identity with the sequence of SEO ID NO: 4; and
   nucleic acid sequences encoding a GroEL
or a functional homologue of GroEL, and a GroES or a functional homologue of GroES, wherein
the respective GroEL and GroES homologues are functional as molecular chaperones,
   wherein the amino acid sequence of the GroEL or the functional homologue of GroEL has at least 70% sequence identity with the sequence of SEO ID NO: 10; and
   wherein the amino acid sequence of the GroES or the functional homologue of GroES has at least 70% sequence identity with the sequence of SEO ID NO: 12.

2. The recombinant yeast cell of claim 1, wherein the Rubisco uses CO2 as an electron acceptor.

3. The recombinant yeast cell of claim 1, wherein the Rubisco is a single subunit Rubisco.

4. The recombinant yeast cell of claim 1, wherein the Rubisco is a prokaryotic form-II Rubisco.

5. The recombinant yeast cell of claim 1, wherein the PRK is a PRK originating from a eukaryote.

6. The recombinant yeast cell of claim 5, wherein the PRK originates from a Caryophyllales plant.

7. The recombinant yeast cell of claim 6, wherein the Caryophyllales plant is Amaranthaceae or *Spinacia*.

8. The recombinant yeast cell of claim 1, wherein the genus of said yeast cell is selected from the group consisting of Saccharomycesaceae, *Schizosaccharomyces, Torulaspora, Kluyveromyces, Pichia, Zygosaccharomyces, Brettanomyces, Metschnikowia, Issatchenkia, Kloeckera*, and *Aureobasidium*.

9. The recombinant yeast cell of claim 8, wherein the genus of yeast cell is Saccharomycesceae.

10. The recombinant yeast cell of claim 9, wherein the yeast cell is selected from the group consisting of *Saccharomyces cerevisiae, Saccharomyces pastorianus, Saccharomyces beticus, Saccharomyces fermentati, Saccharomyces paradoxus, Saccharomyces uvarum*, and *Saccharomyces bayanus*.

11. A method for preparing an alcohol under anaerobic conditions comprising fermenting a carbon source and the recombinant yeast cell of claim 1.

12. The recombinant yeast cell of claim 7, wherein the PRK is a *Spinacia* PRK.

13. The recombinant yeast cell of claim 9, wherein the yeast cell is a *Saccharomyces cerevisiae*.

14. The recombinant yeast cell of claim 1, wherein the amino acid sequence of the GroEL or the functional homologue of GroEL has at least 75% sequence identity with the sequence of SEQ ID NO: 10; and the amino acid sequence of the GroES or the functional homologue of GroES has at least 75% sequence identity with the sequence of SEQ ID NO: 12.

15. The recombinant yeast cell of claim 1, wherein the amino acid sequence of the GroEL or the functional homologue of GroEL has at least 80% sequence identity with the sequence of SEQ ID NO: 10; and the amino acid sequence of the GroES or the functional homologue of GroES has at least 80% sequence identity with the sequence of SEQ ID NO: 12.

16. The recombinant yeast cell of claim 1, further comprising a heterologous nucleic acid sequence encoding a dehydrogenase.

17. The recombinant yeast cell of claim 16, wherein the dehydrogenase is a xylitol dehydrogenase.

18. The recombinant yeast cell of claim 1, wherein the amino acid sequence of the GroEL or the functional homologue of GroEL has at least 85% sequence identity with the sequence of SEQ ID NO: 10; and the amino acid sequence of the GroES or the functional homologue of GroES has at least 85% sequence identity with the sequence of SEQ ID NO: 12.

19. The recombinant yeast cell of claim 1, wherein the amino acid sequence of the GroEL or the functional homologue of GroEL has at least 90% sequence identity with the sequence of SEQ ID NO: 10; and the amino acid sequence of the GroES or the functional homologue of GroES has at least 90% sequence identity with the sequence of SEQ ID NO: 12.

20. The recombinant yeast cell of claim 1, wherein the amino acid sequence of the GroEL or the functional homologue of GroEL has at least 95% sequence identity with the sequence of SEQ ID NO: 10; and the amino acid sequence of the GroES or the functional homologue of GroES has at least 95% sequence identity with the sequence of SEQ ID NO: 12.

21. The recombinant yeast cell of claim 1, wherein the amino acid sequence of the Rubisco has at least 85% sequence identity with the sequence of SEQ ID NO: 2.

22. The recombinant yeast cell of claim 1, wherein the amino acid sequence of the Rubisco has at least 90% sequence identity with the sequence of SEQ ID NO: 2.

23. The recombinant yeast cell of claim 1, wherein the amino acid sequence of the Rubisco has at least 95% sequence identity with the sequence of SEQ ID NO: 2.

24. The recombinant yeast cell of claim 1, wherein the amino acid sequence of the PRK has at least 75% sequence identity with the sequence of SEQ ID NO: 4.

25. The recombinant yeast cell of claim 1, wherein the amino acid sequence of the PRK has at least 80% sequence identity with the sequence of SEQ ID NO: 4.

26. The recombinant yeast cell of claim 1, wherein the amino acid sequence of the PRK has at least 85% sequence identity with the sequence of SEQ ID NO: 4.

27. The recombinant yeast cell of claim 1, wherein the amino acid sequence of the PRK has at least 90% sequence identity with the sequence of SEQ ID NO: 4.

28. The recombinant yeast cell of claim 1, wherein the amino acid sequence of the PRK has at least 95% sequence identity with the sequence of SEQ ID NO: 4.

* * * * *